(12) United States Patent
Stang et al.

(10) Patent No.: US 11,426,080 B2
(45) Date of Patent: Aug. 30, 2022

(54) REAL-TIME IMAGING SYSTEM FOR MONITORING AND CONTROL OF THERMAL THERAPY TREATMENTS

(71) Applicant: University of Southern California, Los Angeles, CA (US)

(72) Inventors: John P. Stang, South Pasadena, CA (US); Mark S. Haynes, Pasadena, CA (US); Mahta Moghaddam, Los Angeles, CA (US); Guanbo Chen, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 1304 days.

(21) Appl. No.: 15/658,305

(22) Filed: Jul. 24, 2017

(65) Prior Publication Data

US 2018/0020926 A1 Jan. 25, 2018

Related U.S. Application Data

(60) Provisional application No. 62/365,927, filed on Jul. 22, 2016.

(51) Int. Cl.
*A61B 5/01* (2006.01)
*A61B 5/055* (2006.01)
(Continued)

(52) U.S. Cl.
CPC ............ *A61B 5/015* (2013.01); *A61B 5/0036* (2018.08); *A61B 5/055* (2013.01); *A61B 5/4836* (2013.01); *A61B 8/463* (2013.01)

(58) Field of Classification Search
CPC ....... A61B 5/015; A61B 5/055; A61B 5/0033; A61B 8/463
See application file for complete search history.

(56) References Cited

U.S. PATENT DOCUMENTS

2005/0054914 A1 3/2005 Duerk et al.
2007/0083114 A1* 4/2007 Yang .................... G06T 3/4053
600/437
(Continued)

FOREIGN PATENT DOCUMENTS

WO 2017125397 A1 7/2017

OTHER PUBLICATIONS

Stang, "A 3D active microwave imaging system for breast cancer screening," Ph.D. dissertation, Dept. Elect. and Comp. Eng., Duke Univ., Durham NC, 2008.
(Continued)

*Primary Examiner* — Rochelle D Turchen
(74) *Attorney, Agent, or Firm* — Michael Best & Friedrich LLP

(57) ABSTRACT

Methods and systems of monitoring and controlling thermal therapy treatments. One method includes determining, with an electronic processor, a propagation constant for a plurality of waveports. The method also includes modeling an object within an imaging cavity using a sparse mesh model. The method also includes determining a simulated impedance of the object based on the model of the object. The method also includes calibrating the simulated impedance with a theoretical impedance numerically calculated for the object. The method also includes determining a distribution of an electric field and a distribution of a magnetic field for a mode in a conformal modeled waveport based on the calibrated impedance and the model of the object. The method also includes exciting the plurality of waveports to generate the determined distribution of the electric field and the distribution of the magnetic field.

10 Claims, 48 Drawing Sheets
(42 of 48 Drawing Sheet(s) Filed in Color)

(51) Int. Cl.
  A61B 5/00    (2006.01)
  A61B 8/00    (2006.01)

(56) References Cited

U.S. PATENT DOCUMENTS

2012/0019406 A1    1/2012   Sarkis
2013/0135136 A1*   5/2013   Haynes .................. G01S 7/412
                                                        342/22
2016/0317061 A1   11/2016   Ostadrahimi et al.

OTHER PUBLICATIONS

Stauffer, "Evolving technology for thermal therapy of cancer." International Journal of Hyperthermia, vol. 21, No. 8, pp. 731-744, 2005.
Taflove et al., "Detailed FD-TD analysis of electromagnetic fields penetrating narrow slots and lapped joints in thick conducting screens," IEEE Transactions on Antennas and Propagation, vol. 36, pp. 247-257, Feb. 1988.
Umashankar et al.; "A Novel Method to Analyze Electromagnetic Scattering of Complex Objects," IEEE Transactions on Electromagnetic Compatibility, vol. EMC-24, pp. 397-405, Nov. 1982.
Van Den Berg et al., "Blind shape reconstruction from experimental data," IEEE Transactions on Antennas and Propagation, vol. 43, pp. 1389-1396, Dec. 1995.
Vernon et al., "Radiotherapy with or without hyperthermia in the treatment of superficial localized breast cancer: Results from five randomized controlled trials," Int. J. Radiat. Oncol. Biol. Phys, vol. 35, pp. 731744, 1996.
Wickersheim et al., "Fiberoptic thermometry and its applications," J. Microwave Power, vol. 22, No. 2, pp. 85-94, 1987.
Xiao et al., "Enlarged cells for the conformal FDTD method to avoid the time step reduction," IEEE Microwave and Wireless Components Letters, vol. 14, pp. 551-553, Dec. 2004.
Yee, "Numerical Solution of Initial Boundary Value Problems In-volving Maxwell's Equations in Isotropic Media," IEEE Transactions on Antennas and Propagation, vol. 14, pp. 302-307, May 1966.
Yuan et al., "The Diagonal Tensor Approximation (DTA) for Objects in a Non-Canonical Inhomogeneous Background," Progress In Electromagnetics Research, vol. 112, pp. 1-21, 2011.
Zagorodnov et al., "A uniformly stable conformal FDTD-method in Cartesian grids," Int. J. Numer. Model., vol. 16, pp. 127-141, Mar. 2003.
Zastrow et al., "Database of 3D Grid-Based Numerical Breast Phantoms for use in Computational Electromagnetics Simulations," http://uwcem.ece.wisc.edu/MRIdatabase/.
Zastrow et al., "Development of anatomically realistic numerical breast phantoms with accurate dielectric properties for modeling microwave interactions with the human breast," IEEE Trans. Biomedical Engineering, vol. 55, No. 12, pp. 2792-2800, 2008.
Zhao et al., "A compact 2-D full-wave finite-difference frequency-domain method for general guided wave structures," IEEE Transactions on Microwave Theory and Techniques, vol. 50, pp. 1844-1848, Jul. 2002.
Dewhirst et al., "Hyperthermia," in L Gunderson, J. Tepper Clinical Radiation Oncology, 3rd ed. Philadelphia: Elsevier-Saunders, 2012, pp. 385-403.
Samulski et al., "Thermometry in therapeutic hyperthermia," Methods of hyperthermia control. Springer, Berlin, pp. 1-34, 1990.
Akinci, et al., "Qualitative Microwave Imaging With Scattering Parameters Measurements," IEEE Transactions on Microwave Theory and Techniques, vol. 63, pp. 2730-2740, Sep. 2015.
Ali et al., "3d Nonlinear Super-Resolution Microwave Inversion Technique Using Time-Domain Data," IEEE Transactions on Antennas and Propagation, vol. 58, pp. 2327-2336, Jul. 2010.
Al-Joumayly et al., "Dualband miniaturized patch antennas for microwave breast imaging." IEEE Antennas and Wireless Propagation Letters, vol. 9, pp. 268-271, 2012.
Arnal et al., "Monitoring of thermal therapy based on shear modulus changes: II. Shear wave imaging of thermal lesions." IEEE Trans. Ultrasonics, Ferroelectrics and Frequency Control, vol. 58, No. 8, pp. 1603-1611, 2011.
Arthur et al., "Noninvasive estimation of hyperthermia temperatures with ultrasound." International Journal of Hyperthermia, vol. 21, No. 6, pp. 589-600, 2005.
Behnia et al., "Closed loop feedback control of phased-array microwave heating using thermal measurements from magnetic resonance imaging." Concepts in Magnetic Resonance, vol. 15, No. 1, pp. 101-110, 2002.
Belkbir et al., "Validation of 2d iNverse Scattering Algorithms From Multi-Frequency Experimental Data," Journal of Electromagnetic Waves and Applications, vol. 14, pp. 1637-1667, Jan. 2000.
Benkler et al., "A new 3-D conformal PEC FDTD scheme with user-defined geometric precision and derived stability criterion," IEEE Transactions on Antennas and Propagation, vol. 54, pp. 1843-1849, Jun. 2006.
Benkler et al., "FDTD Subcell Models Powering Computational Antenna Optimization," in The Second European Conference on Antennas and Propagation, 2007. EuCAP 2007, pp. 1-4, Nov. 2007.
Bolomey et al., "On the possible use of microwave-active imaging for remote thermal sensing," IEEE Trans. On Microwave Theory and Techniques, vol. 31, No. 9, pp. 777-781, Sep. 1983.
Burfeindt et al., "Quantitative Microwave Imaging of Realistic Numerical Breast Phantoms Using an Enclosed Array of Multiband, Miniaturized Patch Antennas," IEEE Antennas and Wireless Propagation Letters, vol. 11, pp. 1626-1629, 2012.
Chen et al., "A Conformal FDTD Method with Accurate Waveport Excitation and S-Parameter Extraction," IEEE Trans. Antennas Propag., submitted Oct. 5, 2015, in review.
Chen et al.,, "http://mixil.usc.edu/cfdfd," Dec. 2015.
Cheng et al., "Online feedback focusing algorithm for hyperthermia cancer treatment.", International Journal of Hyperthermia, vol. 23, No. 7, pp. 539-554, 2007.
Chew et al., "Reconstruction of two-dimensional permittivity distribution using the distorted Born iterative method." IEEE. Trans. Medical Imaging, vol. 9, No. 2, pp. 218-225, 1990.
Cui et al., "Study of resolution and super resolution in electromagnetic imaging for half-space problems," IEEE Transactions on Antennas and Propagation, vol. 52, pp. 1398-1411, Jun. 2004.
Das et al., "A method of MRI-based thermal modelling for a RF phased array." International Journal of Hyperthermia, vol. 17, No. 6, pp. 465-482, 2001.
De Senneville et al., "Magnetic resonance temperature imaging." International Journal of Hyperthermia, vol. 21, No. 6, pp. 515-531, 2005.
Dey et al., "A locally conformal finite-difference time-domain (FDTD) algorithm for modeling three-dimensional perfectly conducting objects," IEEE Microwave and Guided Wave Letters, vol. 7, pp. 273-275, Sep. 1997.
Diederich, "Thermal ablation and high-temperature thermal therapy: overview of technology and clinical implementation." International journal of hyperthermia, vol. 21, No. 8, pp. 745-753, 2005.
Ferrero et al., "Two-port network analyzer calibration using an unknown "thru"," IEEE Microwave and Guided Wave Letters, vol. 2, No. 12, pp. 505-507, Dec. 1992.
Gellermann et al., "A practical approach to thermography in a hyperthermia/magnetic resonance hybrid system: Validation in a heterogeneous phantom." International Journal of Radiation Oncology, vol. 61, No. 1, pp. 267-277, 2005.
Gellermann et al., "Noninvasive magnetic resonance thermography of soft tissue sarcomas during regional hyperthermia.". Cancer, vol. 107, No. 6, pp. 1373-1382, 2006.
Gwarek et al., "A differential method of reflection coefficient extraction from FDTD simulations," IEEE Microwave and Guided Wave Letters, vol. 6, pp. 215-217, May 1996.
Gwarek et al., "Wide-band S-parameter extraction from FD-TD simulations for propagating and evanescent modes in inhomogeneous guides," IEEE Transactions on Microwave Theory and Techniques, vol. 51, pp. 1920-1928, Aug. 2003.

(56) References Cited

OTHER PUBLICATIONS

Haynes et al., "Microwave breast imaging system prototype with integrated numerical characterization." Journal of Biomedical Imaging, vol. 2012, Article ID 706365, 18 pages, 2012. doi:10.1155/2012/706365.

Haynes et al., "Real-time Microwave Imaging of Differential Temperature for Thermal Therapy Monitoring," IEEE Transactions on Biomedical Engineering, vol. 61, pp. 1787-1797, Jun. 2014.

Haynes et al., "Vector Green's function for S-parameter measurements of the electromagnetic volume integral equation," in 2011 IEEE International Symposium on Antennas and Propagation (APSURSI), pp. 1100-1103, Jul. 2011.

Haynes et al., "Vector Green's function for Sparameter measurements of the electromagnetic volume integral equation," IEEE Transactions on Antennas and Propagation, vol. 60, pp. 1400-1413, Mar. 2012.

Hildebrandt et al., "The cellular and molecular basis of hyperthermia," Critical Rev. Oncology/Hematology, vol. 43, No. 1, pp. 33-56, 2002.

Hynynen et al., "MRI guided and monitored focused ultrasound thermal ablation methods: a review of progress." International Journal of Hyperthermia, vol. 20, No. 7, pp. 725-737, 2004.

Katzir et al., "Infrared fibers for radiometer thermometry in hypothermia and hyperthermia treatment." IEEE Trans. Biomedical Engineering, vol. 36, No. 6, pp. 634-637, 1989.

Kennedy, "High-intensity focused ultrasound in the treatment of solid tumours," Nature Rev. Cancer, vol. 5, pp. 321-327, 2005.

Komarov et al., "Dielectric permittivity and loss factor of tap water at 915 MHz," Microwave and Optical Technology Letters, vol. 42, No. 5, pp. 419-420, Sep. 2004.

Komarov et al., "Permittivity and measurements." Encyclopaedia of RF and Microwave Engineering, No. 308, pp. 1-20, 2005.

Larina et al., "Real-time optoacoustic monitoring of temperature in tissues." Journal of Physics D, vol. 38, No. 15, pp. 2633-2639, 2003.

Lazebnik et al., "A large-scale study of the ultrawideband microwave dielectric properties of normal breast tissue obtained from reduction surgeries," Physics in Medicine and Biology, vol. 52, pp. pp. 2637-2656, 2007.

Lazebnik et al., "Ultrawideband temperature-dependent dielectric properties of animal liver tissue in the microwave frequency range," Phys. Med. Biol., vol. 51, pp. 1941-1955, 2006.

Meaney et al., "A clinical prototype for active microwave imaging of the breast," IEEE Trans. Microwave Theory and Techniques, vol. 48, No. 11, pp. 1841-1853, Nov. 2000.

Meaney et al., "Microwave thermal imaging of scanned focused ultrasound heating: Phantom results." International Journal of Hyperthermia, vol. 24, No. 7, pp. 523-536, 2008.

Meaney et al., "Microwave thermal imaging: Initial in vivo experience with a single heating zone." International Journal of Hyperthermia, vol. 19, No. 6, pp. 617-641, 2003.

Nagata et al., "Clinical results of radiofrequency hyperthermia for malignant liver tumors." International Journal of Radiation Oncology, vol. 38, No. 2, pp. 359-365, 1997.

Nasoni et al., "In vivo temperature dependence of ultrasound speed in tissue and its application to noninvasive temperature monitoring," Ultrasonic Imaging, vol. 1, No. 1, pp. 34-43, 1979.

Navarro et al., "FDTD characterization of evanescent modes-multimode analysis of waveguide discontinuities," IEEE Transactions on Microwave Theory and Techniques, vol. 48, pp. 606-610, Apr. 2000.

Ni et al., "A review of the general aspects of radiofrequency ablation." Abdominal imaging, vol. 30, No. 4, pp. 381-400, 2005.

Railton et al., "The Treatment of Thin Wire and Coaxial Structures in Lossless and Lossy Media in FDTD by the Modification of Assigned Material Parameters," IEEE Transactions on Electromagnetic Compatibility, vol. 48, pp. 654-660, Nov. 2006.

Rehnmark, "On the calibration process of automatic network analyzer systems," IEEE Trans. on Microwave Theory and Techniques, pp. 457-458, Apr. 1974.

Sneed et al., "Hyperthermia," in R. Hoppe, T. L. Phillips, and M. Roach III Textbook of Radiation Oncology: Expert Consult, 3rd ed. Elsevier Health Sciences, 2010, ch. 74, pp. 1564-1593.

Stang et al., "Advances in real-time non-contact monitoring of medical thermal treatment through multistatic array microwave imaging," 2015, 1-4. 10.1109/CAMA.2015.7428114.

Stang et al., , "Tapered microstrip patch antenna array for use in breast cancer screening via 3D active microwave imaging," Proc. IEEE APS/URSI, 2009.

Chen et al., "Real-time tracking of metallic treatment probe in interstitial thermal therapy," 2017, 32nd URSI GASS, 3 pages.

Chen et al., "Numerical vector green's function for s-parameter measurement with waveport excitation," 2017, IEEE Transactions on Antennas and Propagation, 65(7):3645-3653.

International Preliminary Report on Patentability for Application No. PCT/US2018/047229 dated Mar. 5, 2017 (7 pages).

International Search Report and Written Opinion for Application No. PCT/US2018/047229 dated Oct. 22, 2018 (13 pages).

Kleinman et al., "Two-dimensional location and shape reconstruction," Radio Science, vol. 29, No. 4, pp. 1157-1169, 1994.

Luyen et al., "Microwave ablation at 10.0 GHz achieves comparable ablation zones to 1.9 GHz in ex vivo bovine liver," IEEE Transactions on Biomedical Engineering, vol. 61, No. 6, pp. 1702-1710, Jun. 2014.

NIH, "The national library of medicines visible human project." [Online]. Available: <https://www.nlm.nih.gov/research/visible/visible_human.html> publicly available at least as early as Apr. 1999.

Tibshirani, "Regression shrinkage and selection via the lasso", Journal of Royal Statistical Society: Series B, vol. 58, pp. 267-288, 1996.

Van Den Berg et al., "Probing the pareto frontier for basis pursuit solutions", SIAM Journal on Scientific computing, vol. 31, pp. 890-912, 2008.

Wright et al., "Sparse reconstruction by separable approximation", IEEE Transactions on Signal Processing, vol. 57, No. 7, pp. 2479-2493, Jul. 2009.

\* cited by examiner

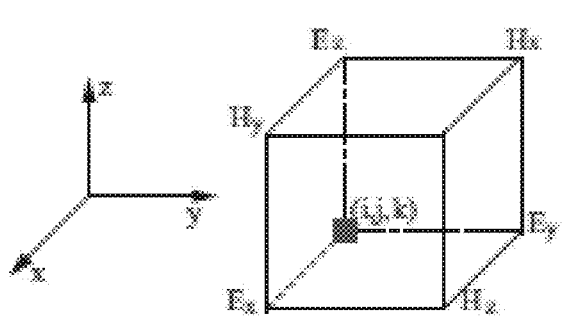 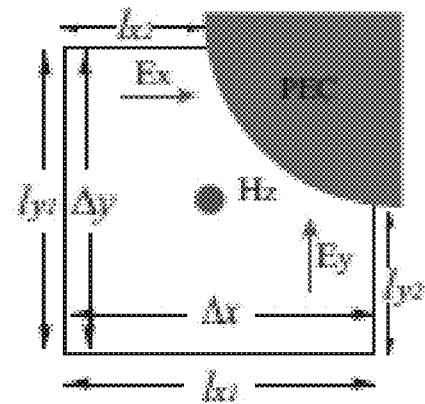
FIG. 29A    FIG. 29B
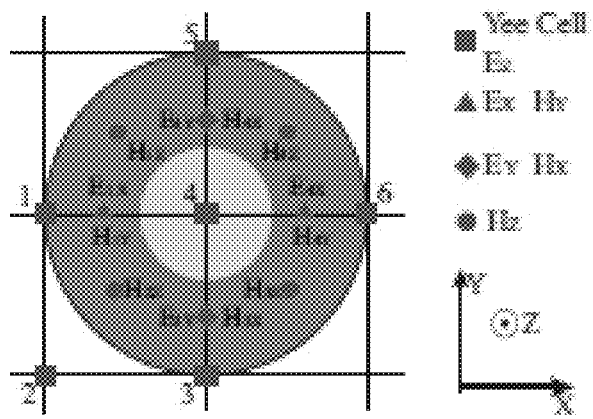 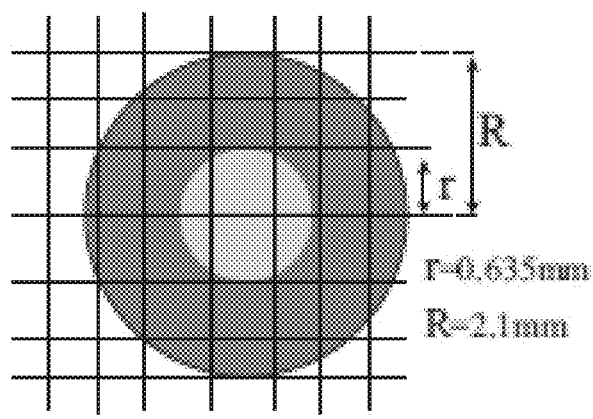
FIG. 30A    FIG. 30B

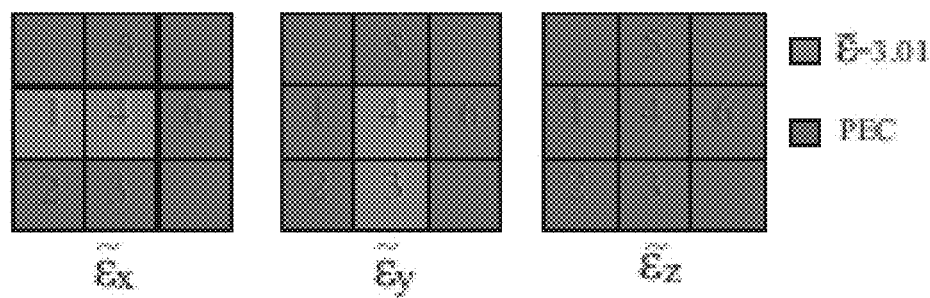
*FIG. 31A*     *FIG. 31B*     *FIG. 31C*
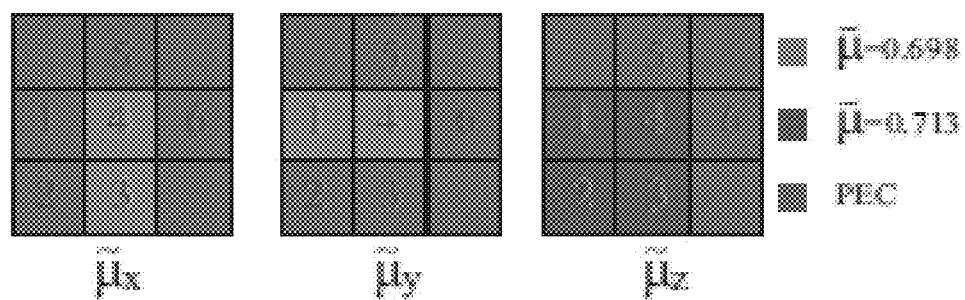
*FIG. 31D*     *FIG. 31E*     *FIG. 31F*

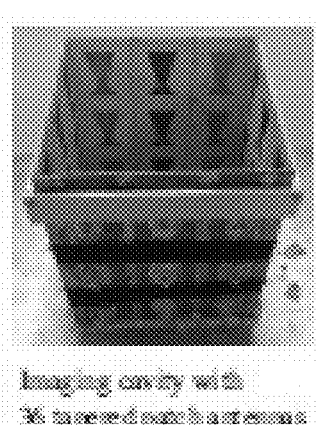 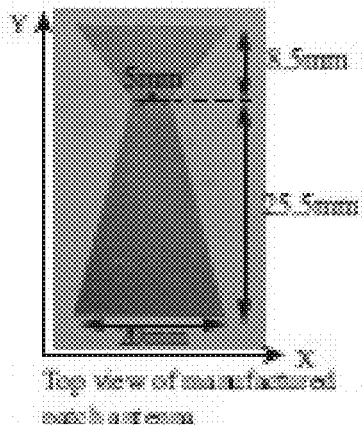 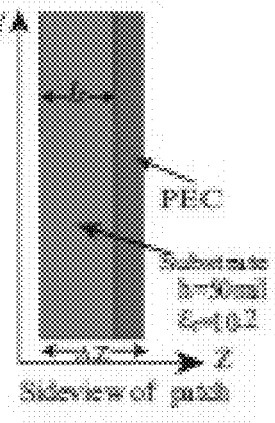
FIG. 32A  FIG. 32B  FIG. 32C
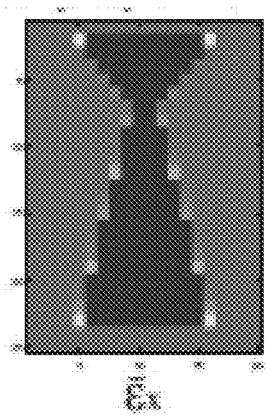 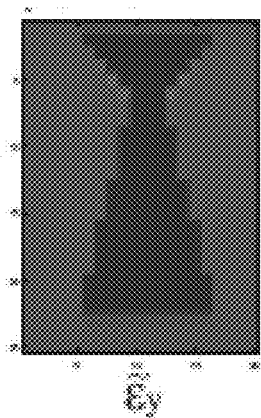 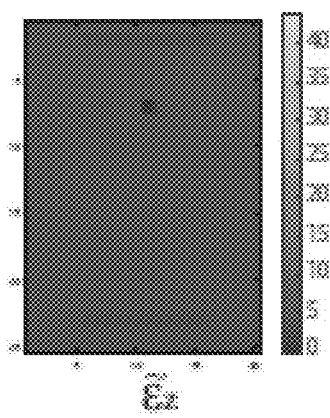
FIG. 32D  FIG. 32E  FIG. 32F

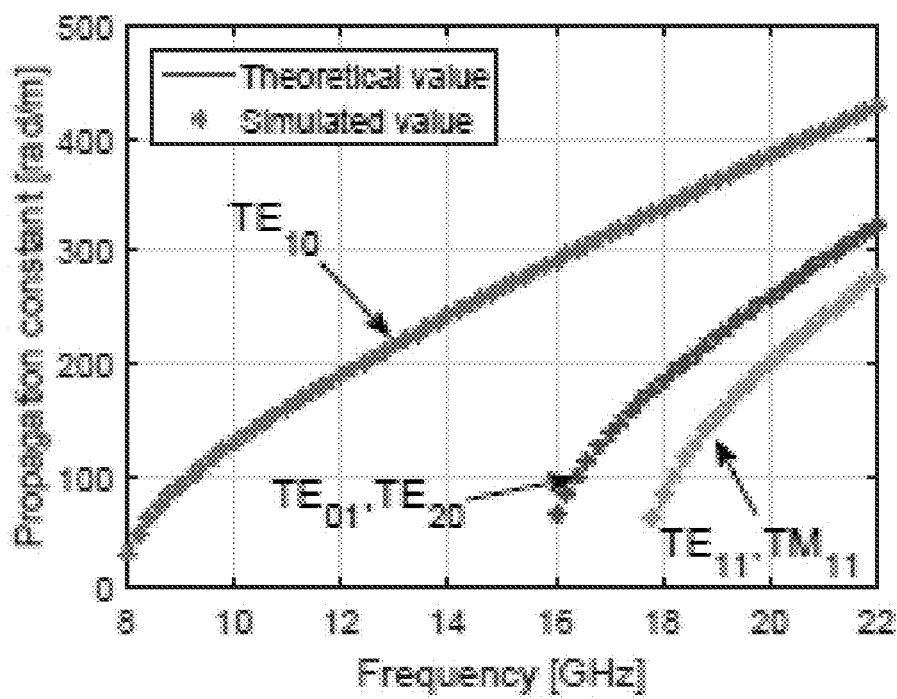
FIG. 35
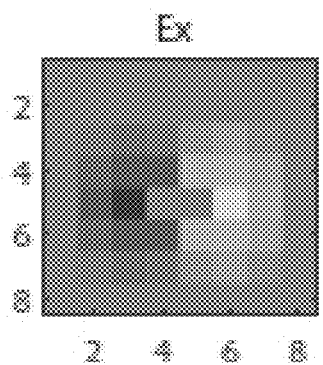 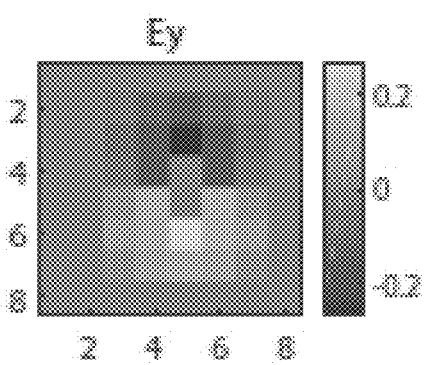
FIG. 36A      FIG. 36B
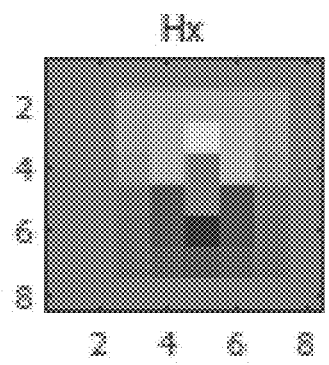 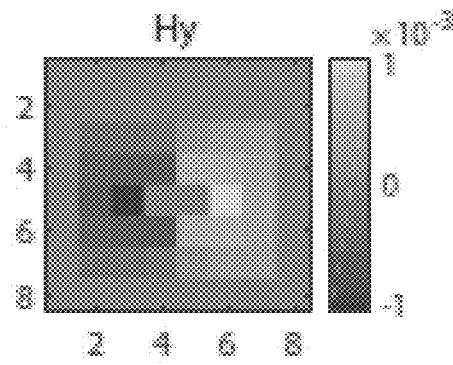
FIG. 36C      FIG. 36D

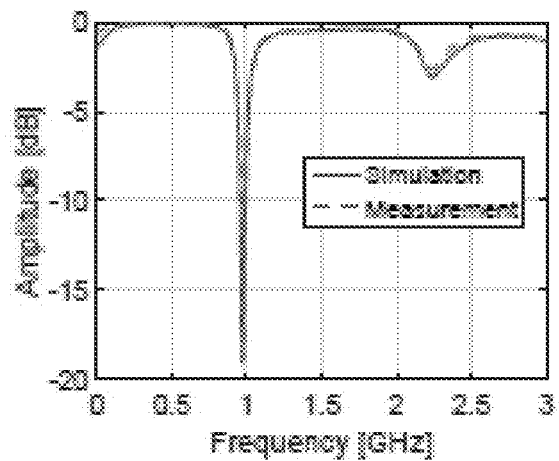 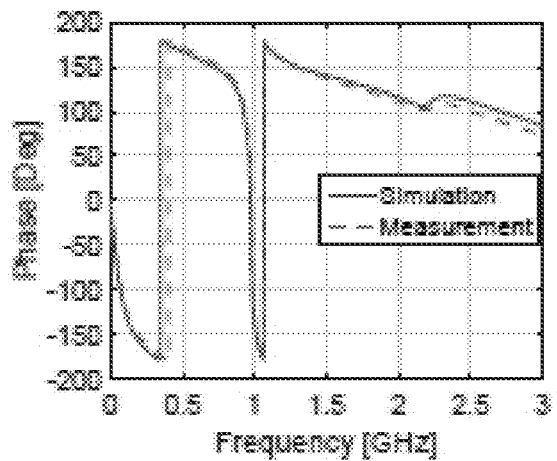
FIG. 37A        FIG. 37B
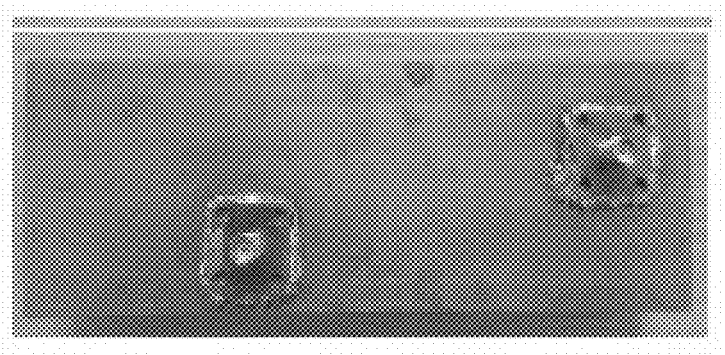 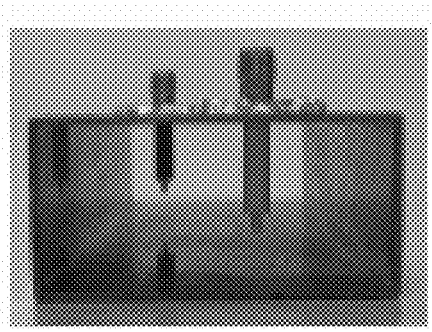
FIG. 38A        FIG. 38B

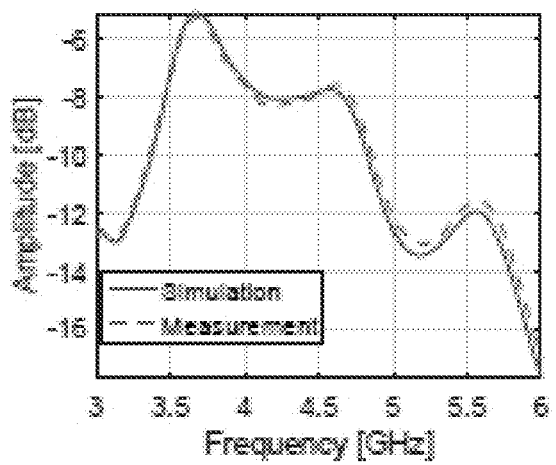 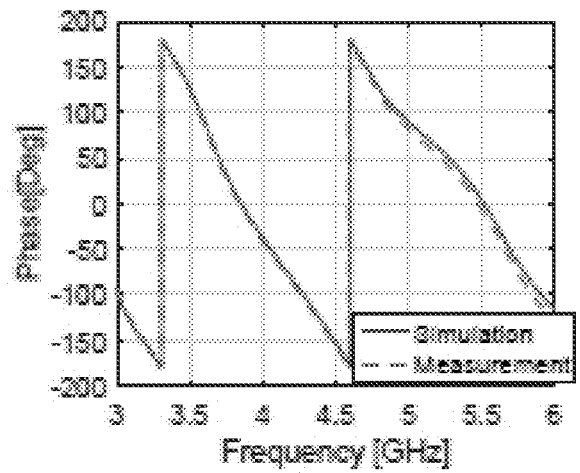
FIG. 39A  FIG. 39B
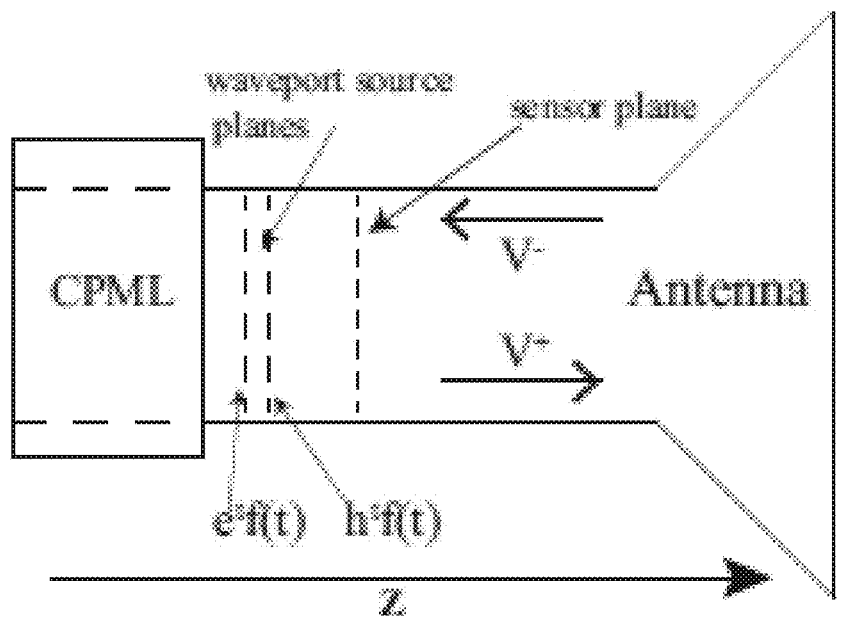
FIG. 40

REAL-TIME IMAGING SYSTEM FOR MONITORING AND CONTROL OF THERMAL THERAPY TREATMENTS

CROSS-REFERENCE TO RELATED APPLICATION(S)

This application is a non-provisional of and claims priority to U.S. Provisional Patent Application No. 62/365,927, filed on Jul. 22, 2016, the entire contents of which is hereby incorporated by reference.

STATEMENT REGARDING FEDERALLY SPONSORED RESEARCH OR DEVELOPMENT

This invention was made with government support under No. 53-4502-6382 awarded by the U.S. Department of Defense and under No. W81XWH-10-1-0514 awarded by the Army Medical Research and Materiel Command. The government has certain rights in the invention.

BACKGROUND OF THE INVENTION

Thermal therapy is a fast-growing and increasingly versatile category of treatments in the fight against cancer. Researchers have developed a number of methods (both invasive and noninvasive) to deliver thermal energy in a variety of forms (including ultrasound, radiofrequency, microwave, and laser). Common to all of these thermal therapies, however, is the necessity for real-time thermal monitoring and guidance. The current standard of MRI-based thermal monitoring is cumbersome, expensive, and requires the therapy system design to be MR-compatible.

SUMMARY OF THE INVENTION

A real-time noninvasive thermal monitoring system based on multi-static microwave imaging is a potential alternative to MR-based thermal monitoring. This system uses microwaves to detect the small changes in the complex permittivity of water that occur due to changes in temperature, and build upon methods and hardware developed previously for the application of breast cancer screening.

Embodiments described herein relate to methods and systems for real-time imaging of differential temperature in a sample using microwaves, and, in particular, to real-time microwave imaging systems for monitoring and control of thermal therapy treatments.

Commercial applications for some embodiments described herein include, for example, thermal dose monitoring and treatment guidance for tumor ablation systems (for example, cryoablation, High Intensity Focused Ultrasound (HIFU), laser induced thermal therapy, radio frequency (RF) ablation, and microwave ablation) and hyperthermia systems. In addition, potential commercial applications exist in the emerging fields of image guided, thermal drug delivery, and thermally controlled regulation of transgene expression using heat-sensitive promoters.

The embodiments described herein address a number of issues with current state of the art MRI-based monitoring systems, which are limited by expense, access, size, and the requirement that the therapy system be MRI compatible.

RF and HIFU thermal ablations are performed without spatial temperature control, currently under computed tomography (CT) or ultrasound (US) monitoring. With US monitoring, the estimation of the actual size of the ablated region is not precise because the extent of the hyperechogenic zone does not strictly correspond to the necrotic area. Using CT monitoring, there is no density change related to acute necrosis. Therefore, for both US and CT monitoring, accurate prediction of the treatment zone requires intravenous injection of contrast material (for example, microbubbles or an iodine compound, respectively). Due to the impracticality of repeated injections, the extent of the ablative zone may only be assessed at the end of the procedure.

Thus far, real-time thermal monitoring has been limited to thermal probes or MR thermometry. Thermal probes are fast and accurate. However, the coverage of thermal probes is limited to the sensor tip and is inherently invasive. MRI has been employed for thermal monitoring, especially in ultrasound ablation and microwave hyperthermia. MRI provides full coverage of a treatment region. However, MRI is limited by expense, access, and the requirement that the thermal delivery system be MRI compatible.

Ultrasonic thermal monitoring has received attention in shear-wave, speed of sound, backscatter variation, and optoacoustic thermal imaging. However, ultrasonic thermal monitoring has not been clinically proven.

A closed-loop, noninvasive focused microwave thermal therapy system has been developed. The system is capable of safe, rapid, and precise adjuvant hyperthermia, neoadjuvant hyperthermia, and thermal ablation. Innovations in thermal monitoring and focusing enable improved outcomes in the fastest growing segment of the nonvascular interventional radiology device market.

Thermal therapy has primarily been used to increase the effectiveness of other treatment methods (for example, hyperthermia to enhance chemotherapy). However, recently thermal therapy has also been used to deliver localized therapeutic agents to a target region as well as for thermal ablation. Hyperthermia employs a thermal dose that is generally safe for normal cells (for example, ~43° C.). However, hyperthermia has the potential for the following therapeutic effects: (1) thermal damage or weakening of cancer cells; (2) increased blood flow through weakened tumor (enhanced delivery of therapeutic agents); (3) increased oxygen levels in tumors; (4) stimulated immune response; and (5) thermal release of therapeutic agents encapsulated in temperature sensitive liposomes. Thermal ablation employs more extreme temperature levels (for example, >60° C. for RF, microwave and <0° C. for cryoablation) to destroy tissue. Localization of the damage is achieved using an invasive probe (radiofrequency ablation) or catheter (cryoablation), or through focusing (HIFU, microwave).

Existing thermal therapy systems are invasive, have poor focusing and control, and require mixed modalities for temperature monitoring. Currently, no wave-based thermal therapy system, or combination of systems, can yet deliver highly controlled non-invasive heat localization with real-time non-invasive temperature monitoring in the same system. These limitations have so far prevented wide scale adoption of microwave thermal therapy despite growing interest in microwave thermal therapy.

At this time, the main application for thermal therapy systems is to improve local control while limiting radiation doses using concurrent hyperthermia with re-irradiation therapy. Hyperthermia has been demonstrated to enhance radiation-induced cell killing. Additionally, several randomized trials have shown an improvement in local control when combined with re-irradiation therapy. By potentiating the effect of radiation, hyperthermia may potentially result in similar tumor control rates with lower overall doses, thereby decreasing the risks associated with re-irradiation therapy. There has also been interest in using neoadjuvant hyperthermia to reduce tumor size prior to surgery. Beyond hyperthermia applications, ablative treatments have been gaining increasing attention as an alternative to standard surgical therapies, as thermal ablation has the potential to reduce morbidity and mortality in comparison with standard surgical resection and has the ability to treat patients with contraindication or those who refuse open surgery. Lastly, thermal therapy has the potential for use in locally targeted drug delivery, in the cosmetic market, and there is emerging interest in the role of thermal devices in triggering an immune-response to cancer.

Current Microwave and Radio Frequency (RF) Thermal Treatment Technology

The technologies of thermal treatment with radio and microwave radiation fall under four categories: (1) invasive treatment; (2) non-invasive treatment; (3) invasive temperature monitoring; and (4) non-invasive temperature monitoring. Radio frequency ablation (RFA) uses large gauge needles that double as coaxial probes. High intensity radio frequency waves propagate down the probe and excite strong electric fields at the probe tip. The localized fields are absorbed by the immediately surrounding tissue and heat to ablation. While conceptually simple, the procedure is invasive and cannot reliably treat tumor margins or large tissue regions. There is no active temperature monitoring. Rather, imaging is used to guide the needle. Also, tissue charring may limit the therapeutic range as treatment progresses. Current microwave ablation systems generally use the same approach, only at a higher frequency and some with the use of additional probes, but all are invasive. Non-invasive hyperthermia systems based on array focusing exist for clinical use. Multiple antennas are used to focus microwave radiation subcutaneously. These systems, however, use very few antennas, and thus have large or undefined focal regions with limited steering ability. Lack of control and modeling may lead to side effects of skin burning and unwanted hot spots.

To monitor heat deposition, invasive 15-gauge catheter fiber optic sensors have been used. While temperature measurement at the probe location is accurate, coverage is limited to the sensor tip. Invasive temperature probes are generally not considered a reasonable long-term solution. Finally, a non-invasive real-time heat monitoring technique based on Proton Resonance Frequency Shift (PRFS) Magnetic Resonance Thermal Imaging (MRTI) has been used in conjunction with microwave focused therapy. MRI provides full coverage of a heated region, but the expense and need for two modalities limits the use of the therapy system to institutions with MRI.

Accordingly, embodiments described herein provide methods and systems that integrate electromagnetic modeling with hardware design to achieve both focused microwave thermal therapy with real-time monitoring in the same system. Focusing is achieved with numerous independently sourced antennas (for example, 36 or 48 antennas) that surround the treatment area and radiate into an enclosure of known construction. The enclosure allows precise electric field modeling of each antenna. The models are used to determine the exact antenna sourcing in order to position, shape, and steer the focal spot as desired. By this method, 3 cm focal spot sizes with better than 1 cm position accuracy may be guaranteed while eliminating unwanted hot spots. The system may focus microwave radiation at one point or many points in a single session. The fine control of the spot location also makes faster scanning possible in order to achieve uniform hyperthermia over large tissue regions, which is not achievable by current systems. The use of many antennas increases the power output, reducing treatment time.

The same antennas and numerical models are also used to implement real-time microwave imaging for temperature monitoring. During treatment, signal paths are periodically re-routed in order to record scattered fields taken off of the tissue being heated. Images are formed of the changes in dielectric properties due to heat. The integration of the therapy and monitoring are possible because (1) many more sources surround the treatment area than in existing systems and (2) the embodiments described herein use the numeric models for microwave focusing and image formation in the same hardware paradigm. This enables implementation of a two-tier monitoring system for improved safety and thermal control. The first is internal monitoring of the microwave circuit outputs. The outputs are sampled at millisecond refresh rates and compared to the model-predicted values for the prescribed focusing. Second, real-time imaging of subcutaneous heat deposition at a one frame per second refresh rate. When either method indicates deviations from desired behavior, the system is shut down. As part of this closed-loop feedback, the images are used to adjust the focal spots in real-time. This is the first known implementation of a non-invasive, single-modality treatment/monitoring system with closed-loop real-time feedback and control.

Embodiments described herein relate to a focused microwave thermal therapy system that utilizes a novel method of integrated real-time microwave thermal monitoring to precisely adjust the amplitude and phase output of custom high power microwave modules. This integrated solution enables on-the-fly optimization of focal spot localization, uniformity of heating, and hotspot minimization based on continuous feedback from (1) microwave thermal mapping and (2) output power monitoring.

In recent years, thermal therapies have seen increased use in cases of subcutaneous cancers of soft tissue. In general, thermal treatments may be classified into two types: (1) thermal ablation, which employs extreme temperatures to induce rapid and localized tissue destruction and (2) hyperthermia, which employs moderately elevated temperatures (typically between 40-45° C.) to sensitize tumor cells to the effects of radiation or chemotherapy. The embodiments described herein may be used for either treatment method and offers improvements upon existing systems in each.

Therapy

Current ablative methods include, for example, cryoablation, high intensity focused ultrasound, radio frequency ablation, and microwave ablation.

Hyperthermia is currently induced using radio frequencies, non-focused ultrasound, and focused microwaves, which have been used as an adjuvant to radiation therapy or chemotherapy.

Monitoring

Existing systems rely on either invasive probes or MR thermometry for thermal monitoring and guidance. The use of fiber optic catheter temperature sensors dates back decades across a range of treatment methods. Invasive probes are fast and accurate. However, the coverage of invasive probes is limited to the sensor tip and the invasive probes are inherently invasive. MRI has been extensively studied for thermal monitoring, especially in ultrasound ablation and microwave hyperthermia. MRI provides full coverage of a treatment region. However, MRI is limited by expense, access, and the requirement that a thermal delivery system be MRI compatible. Ultrasonic thermal monitoring has received attention in shear-wave, speed of sound, backscatter variation, and optoacoustic thermal imaging.

Features of the embodiments described herein include: (1) integrated thermal monitoring, which eliminates the need for additional hardware to monitor thermal therapy delivered by focused microwave heating; (2) custom microwave hardware with full per channel control of magnitude and phase, which allows for real-time monitoring and control of focused microwave therapy array; and (3) the coupling of (i) integrated real-time thermal monitoring with (ii) real-time monitoring and control of the microwave therapy array, which enables real-time, automated enhancement of focused microwave therapy for optimum delivery of thermal dose with minimal operator intervention, all in a noninvasive manner.

Advantages of the embodiments described herein include the fact that: (1) existing methodologies require either invasive probes or an additional imaging system present during the procedure, both of which complicate the procedure, may impede treatment, and require operator intervention to adjust the treatment accordingly; (2) existing methodologies either use invasive probes to deliver treatment (RFA) or suffer from long treatment times (HIFU); and (3) none of the existing methodologies integrate real time thermal monitoring into adaptive treatment planning in the quantitative manner that the embodiments described herein offer. A main consequence is that existing systems are dependent upon operator intervention to adjust treatments in a qualitative way, whereas embodiments described herein use algorithms based on the quantitative data (for example, thermal mapping and per-channel microwave power and phase) to automatically adapt in real-time to achieve the optimal treatment dose.

Commercial applications that may be suitable for the embodiments described herein include (1) thermal ablation, which employs extreme temperatures to induce rapid and localized tissue destruction; (2) hyperthermia, which employs moderately elevated temperatures (for example, typically between 40-45° C.) to sensitize tumor cells to the effects of radiation or chemotherapy; and (3) thermally targeted drug release.

Accordingly, one embodiment provides a system for real-time microwave imaging of differential temperature. The system includes a plurality of antennas arranged in a three-dimensional array adjacent a cavity into which is placed a sample to be analyzed, the plurality of antennas including at least one transmit antenna and at least one receive antenna. The system also includes a vector network analyzer, wherein each of the plurality of antennas is operatively connected to the vector network analyzer. The system also includes a controller operatively connected to the plurality of antennas and the vector network analyzer. The controller is configured to collect a plurality of pairwise measurements from the plurality of antennas to determine a plurality of S-parameters, wherein each pairwise measurement includes a transmit antenna and a receive antenna. The controller is also configured to combine the plurality of S-parameters with a precomputed inverse scattering solution to form an image.

Another embodiment provides a method of monitoring in real-time a microwave thermal therapy. The method includes imaging a treatment region to obtain dielectric properties, mapping the dielectric properties to the treatment region, and conducting the microwave thermal therapy on the treatment region. The method further includes creating a thermal image of the treatment region in real-time and controlling the microwave thermal therapy on the treatment region in response to the created thermal image. Creating the thermal image of the treatment region relies upon the temperature dependency of the dielectric properties in the treatment region. Prior to conducting the microwave thermal therapy, the treatment region is positioning within a low-loss dielectric material. The microwave thermal therapy does not have to be MRI compatible for creating a thermal image of the treatment region in real-time. Creating the thermal image of the treatment region in real-time also does not require intravenous injection of contrast material and does not require an invasive thermal probe. The microwave thermal imaging data is acquired with a through channel connection to signal a discrete measurement within a continuous data stream (for example, hardware) and real-time magnitude thresholding to parse the continuous data stream into discrete measurement groups and real-time median filtering within each discrete measurement group (for example, software). A portion of the treatment region of which the thermal image is created may be user-selectable.

Another embodiment provides a system of monitoring in real-time a thermal therapy. The system includes an imaging cavity including a plurality of antennas arranged in a three-dimensional array around the imaging cavity. The system also includes a controller operatively connected to the imaging cavity. The system is configured to collect, with an electronic processor, a plurality of pairwise measurements from the plurality of antennas to determine a plurality of S-parameters. The system is also configured to apply in real-time a combination of direct-path triggering signals and magnitude thresholding, along with real-time median filtering and per-channel magnitude and phase calibration within each discrete measurement group, to determine a series of discrete S-parameter measurements from a continuous data stream. The controller is also configured to determine an incident electric field inside the imaging cavity for each of the plurality of antennas. The controller is also configured to generate a numerical function directly linking an unknown material property of an object of interest to a measured voltage when the object of interest is positioned within the imaging cavity. The controller is also configured to update a material property of the object of interest. The controller is also configured to determine a total electric field inside the imaging cavity based on the updated material property. The controller is also configured to output an estimated map of complex permittivity for the object of interest based on the total electric field.

Another embodiment provides a method of monitoring in real-time a thermal therapy. The method includes imaging a treatment region to obtain dielectric properties. The method also includes mapping the dielectric properties to the treatment region. The method also includes conducting the thermal therapy on the treatment region. The method also includes creating a thermal image of the treatment region in real-time and controlling the thermal therapy on the treatment region in response to the thermal image.

Another embodiment provides a method of monitoring in real-time a thermal therapy. The method includes determining, with an electronic processor, a propagation constant for a plurality of waveports. The method also includes modeling an object within an imaging cavity using a sparse mesh model. The method also includes determining a simulated impedance of the object based on the model of the object. The method also includes calibrating the simulated impedance with a theoretical impedance numerically calculated for the object. The method also includes determining a distribution of an electric field and a distribution of a magnetic field for a mode in a conformal modeled waveport based on the calibrated impedance and the model of the object. The method also includes exciting the plurality of waveports to generate the determined distribution of the electric field and the distribution of the magnetic field.

Other aspects of the invention will become apparent by consideration of the detailed description and accompanying drawings.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 29A and 29B illustrate a Yee cell and conformal modeling of curvilinear objects where the red square represents the origin of the Yee cell.

FIG. 30A illustrates a sparse mesh to model the Teflon filled coaxial feed.

FIG. 30B illustrates a dense mesh to model the Teflon filled coaxial feed.

FIGS. 31A-31F illustrate effective material values computed using Equation (36) for maximally sparse mesh modeling of coaxial feed and indices indicate the number of Yee cell.

FIGS. 32A-32F illustrate conformal meshing of a tapered patch antenna.

FIG. 35 illustrates propagation constant of the first five modes of the rectangular waveguide.

FIGS. 36A-36D illustrate a cross-sectional field distribution of coaxial feed TEM mode and dense mesh model results are shown for illustration purposes, but sparse mesh results are equally accurate.

FIGS. 37A-37B illustrate tapered patch antenna modeling; magnitude results agrees with a mean absolute difference of 0.17 dB and a maximum difference of 0.52 dB and phase results agree with a mean absolute difference of 2.1 degrees and a maximum difference of 9.8 degrees.

FIGS. 38A and 38B illustrate coaxial probes in a rectangular waveguide.

FIGS. 39A and 39B illustrate the S21 of empty waveguide with coaxial probes; magnitude results agree with a mean absolute difference of 0.31 dB and a maximum difference of 0.72 dB and phase results agrees with mean absolute difference of 5.7 degrees and a maximum difference of 10.4 degrees.

FIG. 40 illustrates a waveport source.

DETAILED DESCRIPTION

Figure 1:
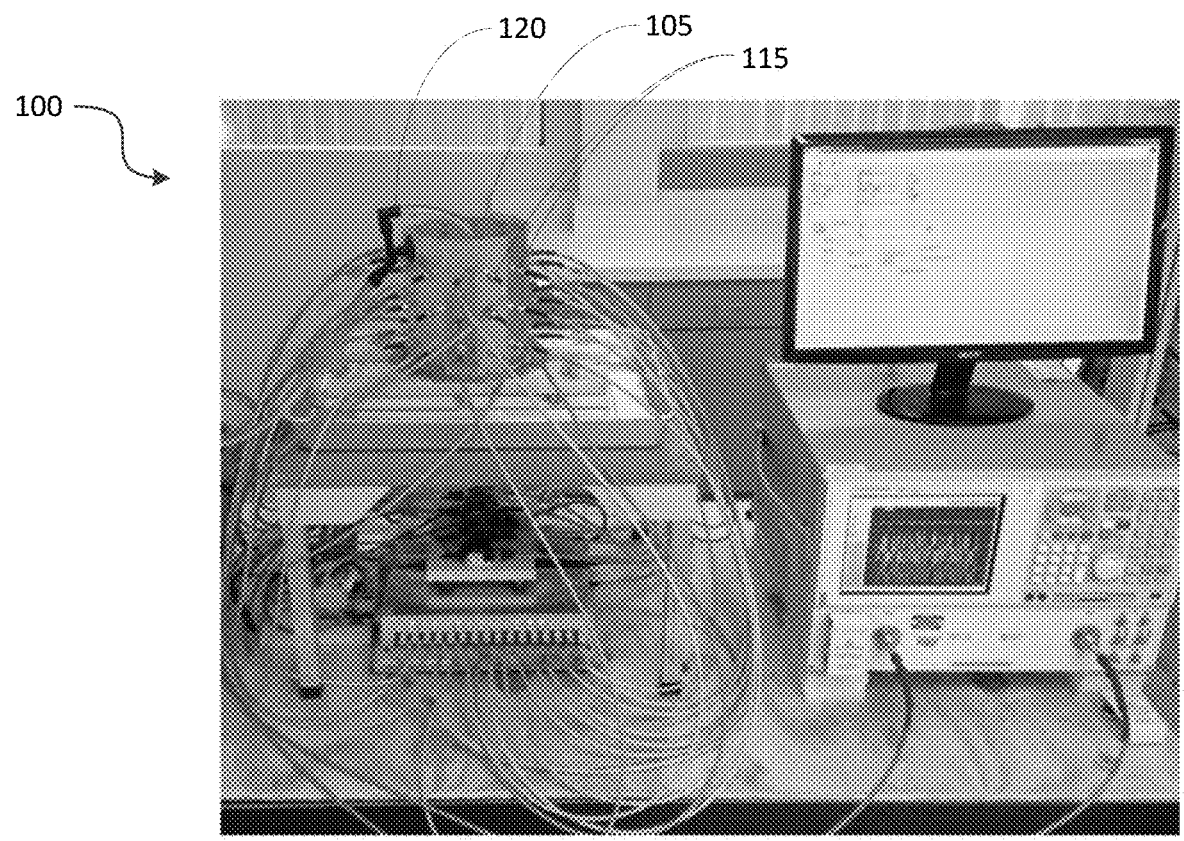
FIG. 1 illustrates a cavity-imaging system for differential temperature imaging with switching matrix, Vector Network Analyzer, Labview control, and fluid circulation.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Section I: Microwave Imaging System for Real-time Monitoring and Feedback of Thermal Therapy Systems Embodiments described herein relate to a microwave imaging system for real-time 3D imaging of differential temperature for the monitoring and feedback of thermal therapy systems. Design parameters are constrained by features of a prototype focused microwave thermal therapy system for the breast, operating at 915 MHz. Real-time imaging is accomplished with a precomputed linear inverse scattering solution combined with continuous Vector Network Analyzer (VNA) measurements of a 36-antenna, HFSS modeled, cylindrical cavity. Volumetric images of differential change of dielectric constant due to temperature are formed with a refresh rate as fast as 1 frame per second and 1° C. resolution. Procedures for data segmentation and postprocessed S-parameter error-correction are developed. Antenna pair VNA calibration is accelerated by using the cavity as the unknown thru standard. The device is tested on water targets and a simple breast phantom. Differentially heated targets are successfully imaged in cluttered environments. The rate of change of scattering contrast magnitude correlates 1:1 with target temperature.

In recent years, thermal therapies have seen increased use in the treatment of a variety of diseases, particularly in cases of subcutaneous cancers of soft tissue. In general, these treatments may be classified into two types: (1) thermal ablation, which employs extreme temperatures to induce rapid and localized tissue destruction and (2) hyperthermia, which employs moderately elevated temperatures (for example, typically between 40-45° C.) to sensitize tumor cells to the effects of radiation or chemotherapy. Ablative methods include cryoablation, high intensity focused ultrasound, radio frequency ablation, and microwave ablation. Hyperthermia is typically induced using radio frequencies, non-focused ultrasound, and focused microwaves which have been used as an adjuvant to radiation therapy or chemotherapy.

As thermal treatment systems evolve, the need for thermal monitoring has motivated research in several modalities. The use of fiber optic catheter temperature sensors dates back decades across a range of treatment methods. Probes are fast and accurate. However, the coverage of probes is limited to the sensor tip and probes are inherently invasive. MRI has been extensively studied for thermal monitoring, especially in ultrasound ablation and microwave hyperthermia. MRI provides full coverage of a treatment region, but is limited by expense, access, and the requirement that a thermal delivery system be MRI compatible. Ultrasonic thermal monitoring has received attention in shear-wave, speed of sound, backscatter variation, and optoacoustic thermal imaging. Also, microwave thermal imaging in a medical setting has been reported for two-dimensional (2D) antenna geometries with inverse scattering techniques. The same system was used to monitor HIFU with 35 second refresh rates. Finally, monitoring provides a mechanism for controlled feedback, which has been reported using real-time MRI guided microwave hyperthermia.

Embodiments described herein relate to microwave-based real-time thermal monitoring within the constraints of focused microwave thermal therapy system parameters in order to avoid the cost and complexities of dual modality implementations. This is done within the design parameters of a previously developed pre-clinical focused microwave prototype for breast cancer therapy. As illustrated in FIG. 1, the imaging system 100 is composed of a cavity-like antenna array at 915 MHz with coupling fluid, vector network analyzer (VNA), and solid-state switching matrix. Using a VNA in this context, with experimental features developed to do so, obviates the need for custom radar hardware in order to accomplish real-time thermal monitoring. Note that this system, as presented, is designed to image changes in dielectric constant due to the application of microwave heating, rather than image the structure of the breast for diagnostic purposes.

Figure 2:
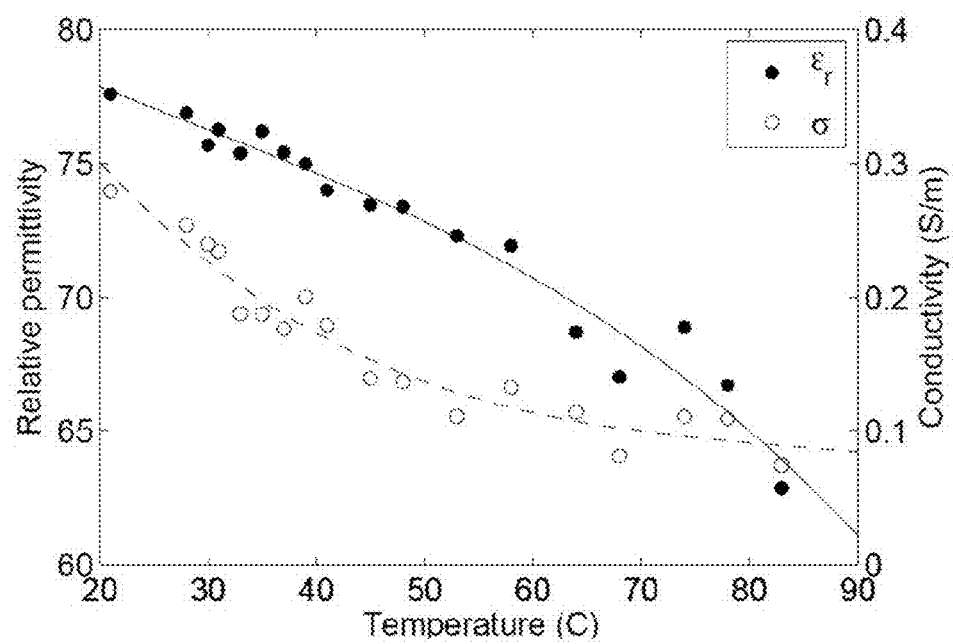
FIG. 2 is a graph of relative permittivity and conductivity of distilled water as a function of temperature at 915 MHz, measured with the Agilent 85070E dielectric probe.

Microwave imaging of differential temperature is predicated on the change in dielectric properties of water with temperature. It is well known that the dielectric properties of water change as a function of temperature. The relative permittivity and conductivity of distilled water as a function of temperature at 915 MHz are plotted in FIG. 2. Within the range of thermal therapy temperatures (for example, 35° C.-60° C.), the relative permittivity of water changes by as much as a few units, and the conductivity up to a factor of 2. The dielectric change of animal liver tissue has been reported to be approximately 1% per ° C. between 28° C. and 53° C. at 915 MHz. Studies of excised breast tissue show that soft-tissue dielectric properties are dominated by water fraction, and are expected to change proportionally with temperature. Thus, even though the dielectric change is small, the ability to detect the dielectric change has been reported in both medical and non-medical settings.

Methods

A. Imaging System

Figure 4:
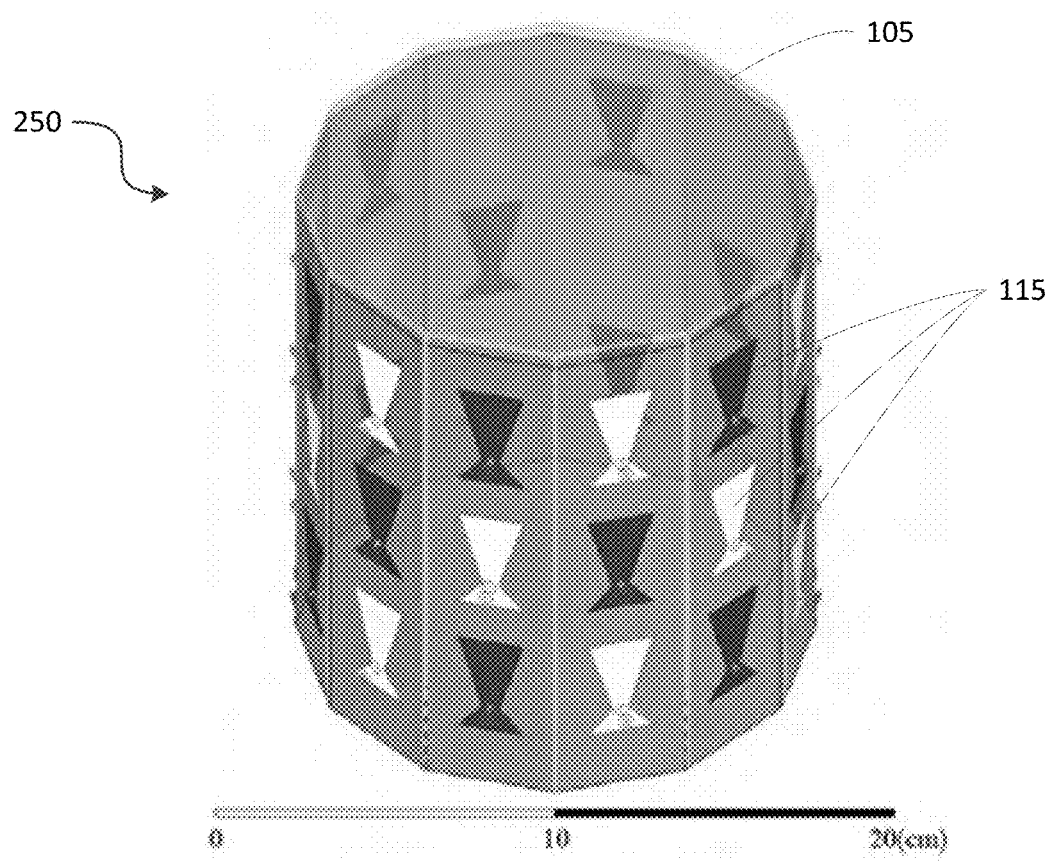
FIG. 4 illustrates a HFSS CAD model of the cavity, the antenna shading designates transmitter and receiver, and the fluid is filled to 0.5 cm below the top.

As illustrated in FIG. 1, the imaging system 100 includes an imaging enclosure 105. The imaging enclosure 105 is a cavity. As illustrated in FIG. 1, the imagining enclosure 105 includes twelve vertical panels of microwave substrate soldered to each other and to a conducting base. Opposing panels are separated by 15 cm, and the cavity is 17 cm tall. There are three antennas per panel for a total of 36 antennas, designed to operate at 915 MHz in a coupling fluid. 2-port S-parameter measurements are taken with an Agilent PNA-5230A Vector Network Analyzer (VNA) between antenna pairs. Pair-wise measurements are routed through 18 transmit (T) antennas and 18 receive (R) antennas using two SP18T solid state switching matrices that connect to Ports 1 and 2, respectively, of the VNA, providing 18²=324 pairwise measurements. T/R antennas alternate around the rows of the cavity and between the rows, as shown in FIG. 4.

The coupling medium is a mixture of isopropyl alcohol and water designed to couple microwave energy into breast tissue. Other fluids have been investigated in literature, such as safflower oil, oil/water emulsion, glycerin, and acetone. The medium is usually chosen to balance conductive loss, relative permittivity, toxicity, antenna match, and ease of use. An alcohol/water mixture is inexpensive, clean, controllable, and not prohibitively lossy at 915 MHz. A 20:7 alcohol:water ratio is used. The dielectric properties of the fluid are measured with the Agilent 85070E dielectric probe kit, at 915 MHz the relative permittivity and conductivity are $(\epsilon_y, \sigma)=(24.5, 0.460$ S/m$)$.

Because the medium is a mixture, the medium must be circulated to prevent separation. An external aquarium pump recirculates the fluid through a drain in the bottom of the cavity to a nozzle at the top. The drain consists of seven 3 mm holes, mimicking a wire mesh, and thus a continuous boundary at 915 MHz. The fluid exchanges once per minute.

The antennas are bow-tie patch antennas designed originally to operate at 915 MHz in an oil/water emulsion with $(\epsilon_y, \sigma)=(23, 0.05$ S/m$)$. In the current coupling medium, the resonance remains, but the impedance match is degraded to about −6 dB.

The SP18T switches each consist of one SP16T switch with two Minicircuits ZYSWA-2-50DR SPDT switches connected to two of the paths. The ensemble is controlled via a computer parallel port. Path isolation is better than 60 dB, except for the Minicircuits switch paths, which are isolated to 40 dB. Differences in attenuation between individual paths are not critical, because each path is individually calibrated.

To maximize the signal to noise ratio (SNR), +13 dBm output power is used, which is the maximum leveled output power of the VNA. In addition, the VNA's 2-port test set is configured to bypass the Port 2 receiver (RCVR) coupler. This increases the Port 2 receiver sensitivity, and thus $S_{21}$ measurements, by +15 dB, while degrading $S_{12}$ by −15 dB. However, only $S_{21}$ is used for imaging.

B. Imaging Cavity used as Unknown 'Thru'

Figure 3A:
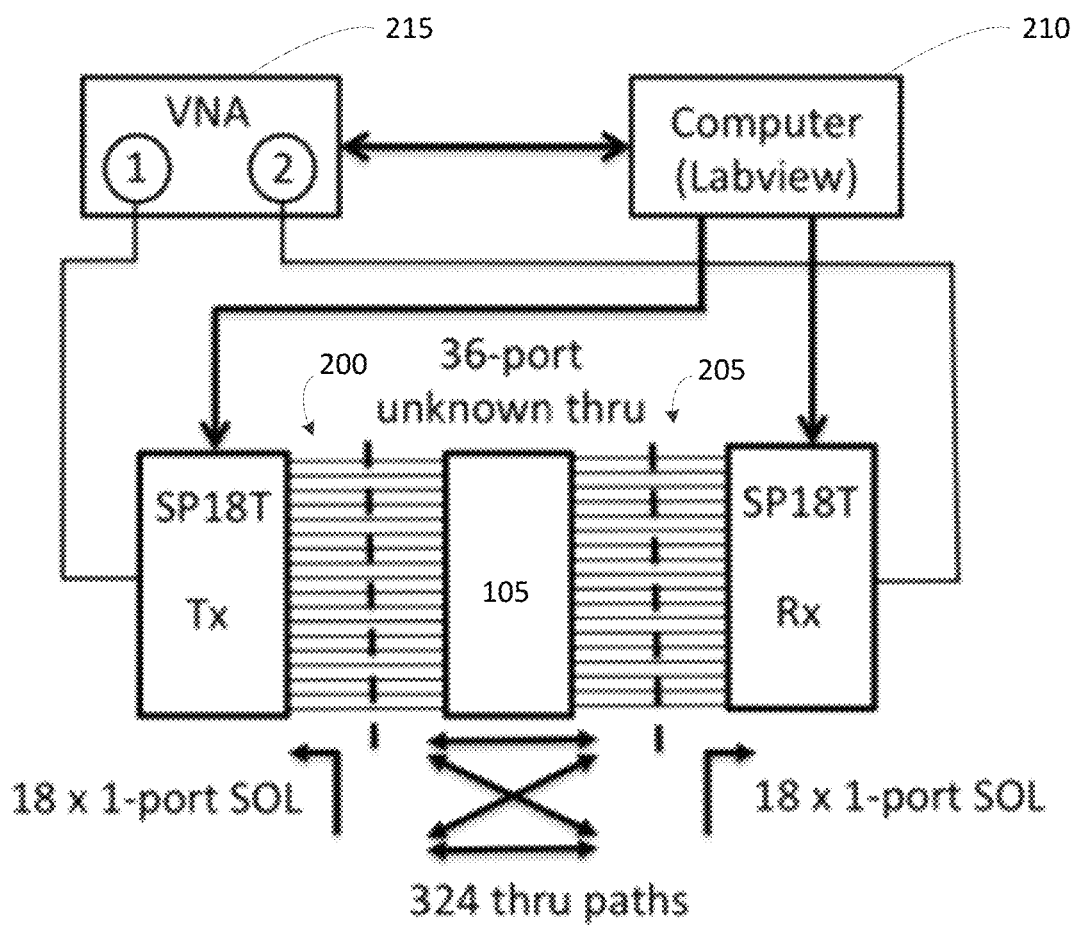
FIG. 3A illustrates a calibration diagram and instrumentation setup that includes a 36-port unknown thru.

In order to compare cavity S-parameter measurements to HFSS and forward scattering predictions (below), a unique 2-port calibration is required between every T/R combination, 324 in total. To accelerate the process, the 2-port unknown 'thru' calibration is used, wherein the cavity itself provides 'thru' paths for every T/R pair. Thru measurements are spliced with individual 1-port calibrations to complete the calibration sets (calsets), diagrammed in FIGS. 3A-3C.

The calibration procedure follows:

1) 1-port Short-Open-Load (SOL) calibrations are saved for each of the 18 transmit and 18 receive paths.
2) The paths are connected to the fluid-filled cavity.
3) A Labview routine selects and switches to a T/R combination.
4) The VNA loads the 1-port SOL calibrations for that combination, completes the unknown thru measurement, computes the error terms, and saves the calset.
5) Process repeats at 3).

Excluding time taken for 1-port SOL calibrations, all 324 2-port calsets are completed in 5 minutes.

Unknown thru calibration is accurate to within the sign of $S_{12}$ and $S_{21}$. The sign ambiguity is resolved by having rough knowledge of the corrected thru measurement phase by, for example, comparing the phase of corrected $S_{12}$ and $S_{21}$ to that predicted by the HFSS cavity model.

Figure 3B:
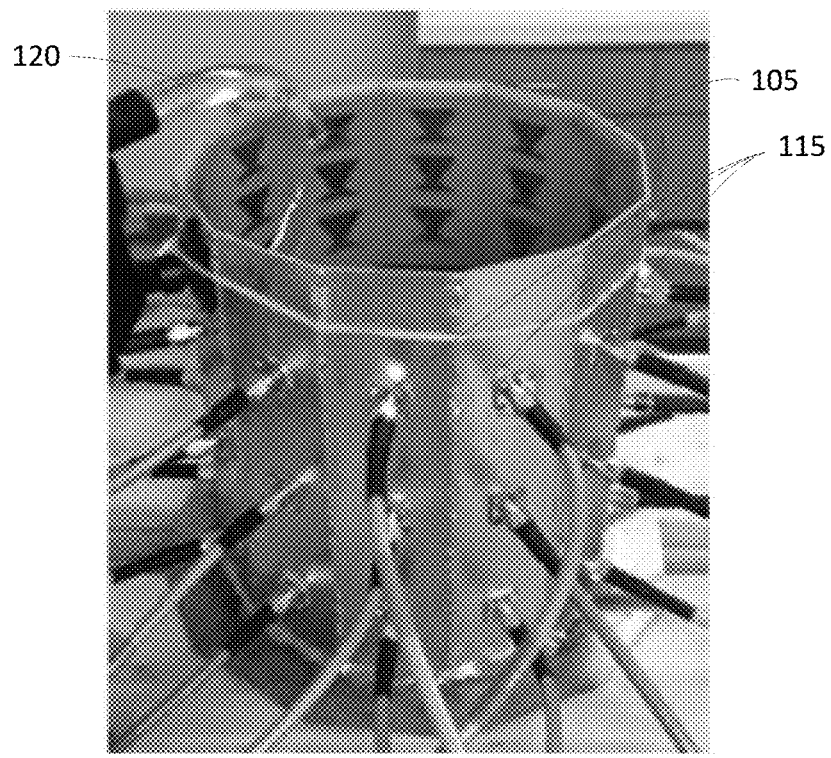
FIG. 3B illustrates a fluid filled cavity used as the known thru standard.
Figure 3C:
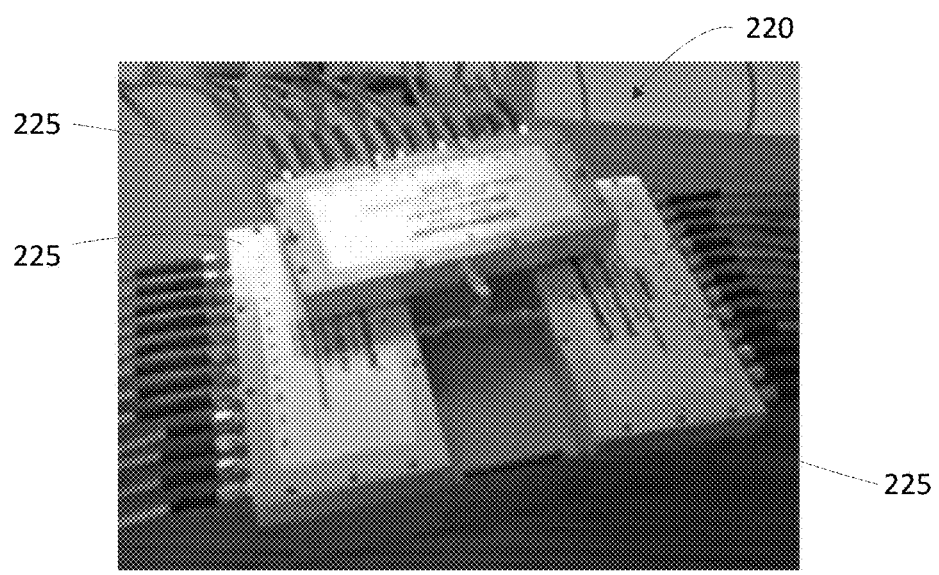
FIG. 3C illustrates a 3×1:12 power divider network tested as an unknown thru.

The method is validated by comparing cavity measurements collected with two calibration sets. The first set uses the fluid-filled cavity as the thru, the second set uses a 36-port power-divider network, as shown in FIGS. 3B and 3C, respectively. The divider network is created by connecting three Minicircuits ZN12PD-252-S+ 1:12 power dividers with a tee. The power divider thru provides nearly equal transmission between all ports, which is not the case for the cavity. Data collection, switching, and calset loading are all automated with Labview. Cavity measurements of the incident field S-parameters using either calibration set are identical to within a sign of $S_{12}$ and $S_{21}$, confirming that either the cavity or power divider may be used as a multi-way unknown thru standard.

In general, any 36-port device with reasonable transmission characteristics may be used as the thru. The advantage of using the cavity itself is that the thru measurements may be repeated without disassembling the setup. However, recalibration is only necessary when the system configuration changes. Overall, this addresses for the first time the unsolved problem in microwave medical imaging of how to efficiently and repeatedly calibrate multi-sensor systems for VNA measurements.

C. HFSS Numerical Model

Figure 5:
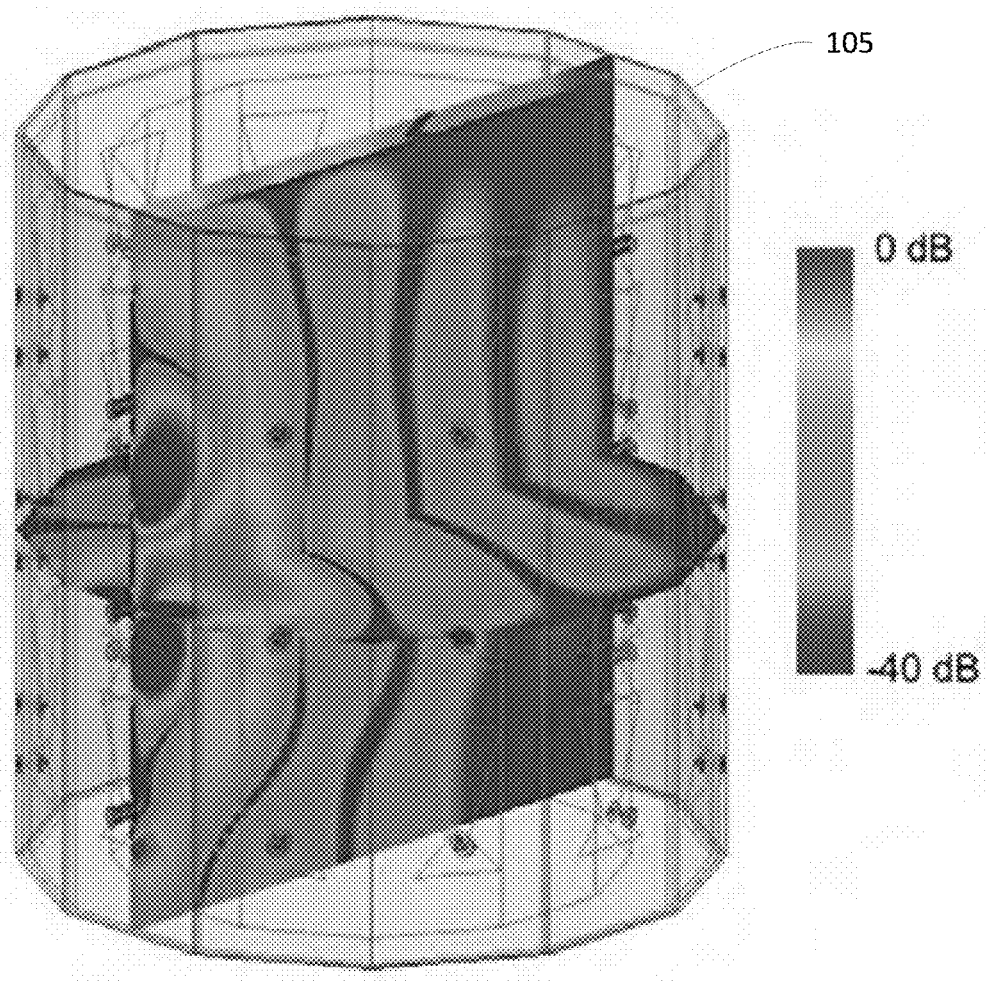
FIG. 5 illustrates cross cuts of $\log(|\Re_e(E_z)|)$ of the normalized incident field for an antenna in the middle row, the walls are PEC, and the top surface radiates to the air.

Ansys HFSS may be used to numerically model the cavity, which requires matching the S-parameter reference planes between simulation and experiment. HFSS may be used to estimate the incident fields throughout the cavity, which include all background multiple scattering not present between the object and the cavity, and are used in the forward scattering model described below. FIG. 4 shows the HFSS CAD model; antennas are shaded as transmitters and receivers. FIG. 5 shows the incident field of one antenna. The drain is assumed to be a continuous copper sheet.

Figure 6A:
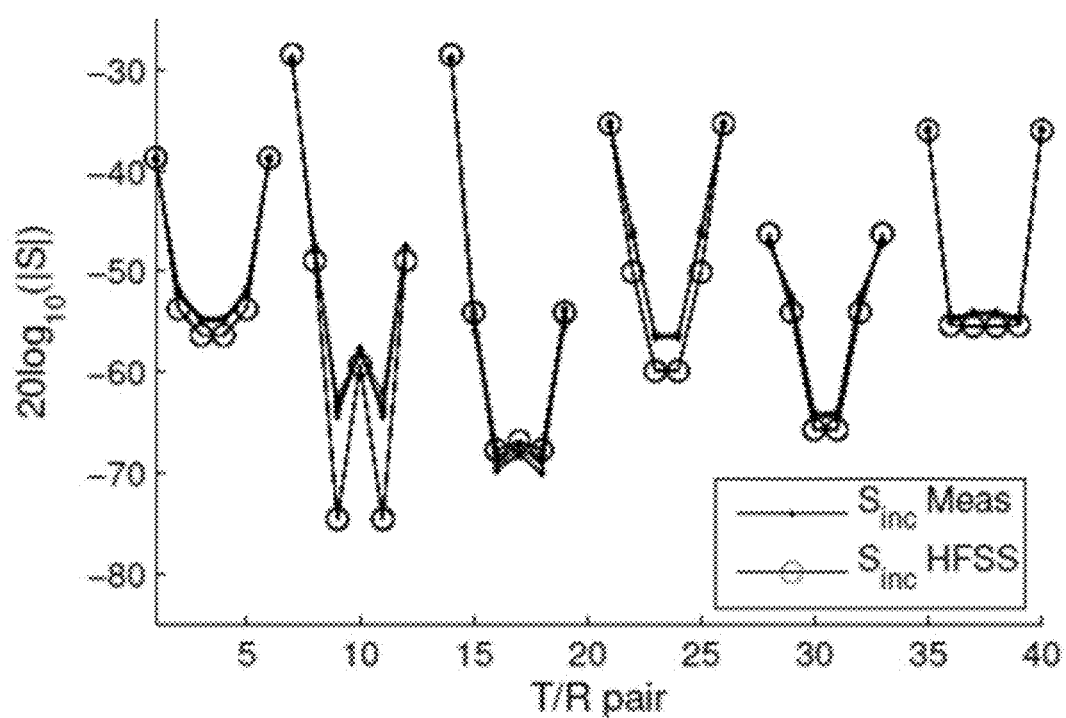
FIG. 6A is a graph of measured and HFSS incident S-parameters including magnitude, where symmetric combinations are overlaid and grouped by row-row interaction.
Figure 6B:
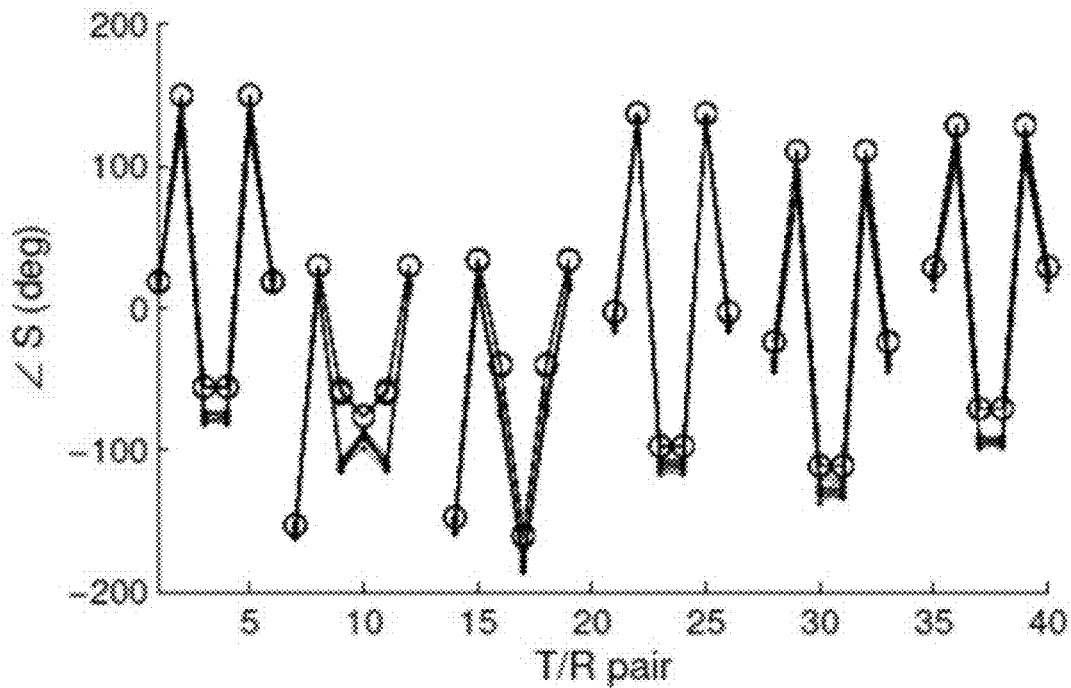
FIG. 6B is a graph of measured and HFSS incident S-parameters including phase, where symmetric combinations are overlaid and grouped by row-row interaction.

Measured and simulated incident S-parameters may be used to assess the accuracy of the HFSS model. FIGS. 6A and 6B show the magnitude and phase, respectively, of the measured and simulated incident S21 S-parameters. The plots overlay circular-symmetric T/R paths, grouped according to the 6 row-row interaction combinations. The groupings from left to right are: middle-middle, middle-top, middle-bottom, top-top, top-bottom, bottom-bottom. The data is plotted this way to assess the symmetry of both the cavity measurements and HFSS simulation, as well as to compare the cavity measurements and HFSS simulation. In general, the magnitude agrees to within 2 dB, and the phase agrees as well as 5 degrees but no worse than 30 degrees. Agreement is best between antennas in the same row.

D. Forward Scattering Model

The forward scattering model predicting the scattered field S-parameter between a transmitter i and receiver j in the presence of an object is given by:

$$S_{ji,sca} = C\int E_{inc,j}(r') \cdot O(r') E_i(r') dV' \quad \text{Equation (1)}$$

where $E_i$ is the total object field produced by the transmitter and $E_{inc,j}$ is the incident field of the receiver.

The object function is defined as:

$$O(r) = \delta\epsilon(r) + i\frac{\delta\sigma(r)}{\epsilon_b \omega} \quad \text{Equation (2)}$$

where $\omega$ is the operating frequency in radians and the background permittivity is $\epsilon_b = \epsilon_o \epsilon_{yb}$ with relative permittivity $\epsilon_{yb}$.

The contrasts are given by:

$$\delta\epsilon(r) = \frac{\epsilon(r)}{\epsilon_b} - 1 \qquad \text{Equation (3)}$$

$$\delta\sigma(r) = \sigma(r) - \sigma_b \qquad \text{Equation (4)}$$

where $\sigma_b$ is the background conductivity, $\delta\epsilon(r)$ is unit-less and $\delta\sigma(r)$ is an absolute measure of conductivity with units of S/m.

The constant is given by:

$$C = -\frac{k_0^2 Z_0^j}{2i\omega\mu a_0^i a_0^j} \qquad \text{Equation (5)}$$

where $k_0$ is the lossless background wavenumber, $k_0^2 = \omega^2 \mu_0 \epsilon_b$, $Z_o^j$ is the characteristic impedance of the receiver transmission line, and $a_0^i$ and $a_0^j$ are the excitations at the S-parameter reference planes of the transmit and receive antennas, respectively.

When estimating the cavity fields with HFSS, the constant simplifies. In simulation, the average transmit power is set to 1 Watt, thus the line voltage is $$a_0 = \sqrt{2P_{ave}Z_0} = \sqrt{2Z_0} \qquad \text{Equation (6)}$$

where the phase of $a_0$ is zero because the S-parameter reference planes of the HFSS model and the cavity are the same. Equation (5) reduces to $$C = -\frac{k_0^2}{4i\omega\mu} \qquad \text{Equation (7)}$$

Finally, in measurement, the scattered field S-parameters are obtained by subtracting the S-parameters for the total and incident fields $$S_{ji,sca} = S_{ji,tot} - S_{ji,inc} \qquad \text{Equation (8)}$$

To increase the accuracy of Equation (1) when comparing Equation (1) with measurement, both sides may be normalized by the incident field S-parameters, while carefully distinguishing simulation from measurement:

$$\frac{S_{ji,sca}^{meas}}{S_{ji,inc}^{meas}} \cong \frac{C}{S_{ji,inc}^{HFSS}} \int E_{ing,j}^{HFSS}(r') \cdot O(r') E_i^{HFSS}(r') dV' \qquad \text{Equation (9)}$$

This helps eliminate multiplicative systematic errors, such as a phase shifts.

E. Differential Scattering

Because the change in the dielectric constant of water due to temperature is small, the inverse scattering problem may be formulated as a perturbation about a background object, where a distorted-type volume integral equation (VIE) is most natural. Formulating the inverse scattering problem this way permits the use of differential total field measurements between heated and unheated objects, which helps eliminate additive systematic errors. The distorted VIE may be augmented with the normalizations and multiplying constant of Equation (9). Also, real-time imaging relies on precomputing the inverse scattering solution, as described in the next section. This may only been done with a constant field estimate: two such estimates are provided in this section.

Let the unheated background object be designated $O_b(r)$, with total field $E^b$, and scattered fields $S_{ji,sca}^b$, and let the heated objected be $O_h(r)$, with total field $E^h$, and scattered fields $S_{ji,sca}^h$. For the case of a differential object measured against a background inhomogeneity, Equation (1) becomes:

$$\Delta S_{ji,sca} = C \int E_j^b(r') \cdot \Delta O(r') E_i^h(r') dV' \qquad \text{Equation (10)}$$

where the volumetric differential scattering contrast between the heated and unheated objects is given by:

$$\Delta O(r) = O_h(r) - O_b(r) \qquad \text{Equation (11)}$$

and the differential scattered field is given by:

$$\Delta S_{ji,sca} = S_{ji,sca}^h - S_{ji,sca}^b = S_{ji,tot}^h - S_{ji,tot}^b \qquad \text{Equation (12)}$$

The right side of Equation (12) results from cancellation of the incident S-parameters, where $S_{ji,tot}^b$ is the baseline object measurement and $S_{ji,tot}^h$ changes with temperature. Note that $S_{ji,tot}^b$ and $S_{ji,tot}^h$ are direct measurements.

Two approximations of Equation (10) are possible. The first is the traditional Born Approximation (BA), in which the total fields are equal to the incident field. The second is the Distorted Born Approximation (DBA), where $E^h = E^b$. Both are conceptually similar. In the BA, the incident fields are those of the empty cavity. In the DBA, the incident fields are those in the background object. Differential scattered fields for the two cases are given by:

$$\Delta S_{ji,sca}^{BA} \approx C \int E_{inc,j}(r') \cdot \Delta O(r') E_{inc,i}(r') dV' \qquad \text{Equation (13)}$$

$$\Delta S_{ji,sca}^{DBA} = C \int E_j^b(r') \cdot \Delta O(r') E_i^b(r') dV' \qquad \text{Equation (14)}$$

The choice of approximation depends largely on the information available. The BA requires simulation of only the empty cavity. The DBA requires knowledge of the total fields in the background object, and, thus, the dielectric properties of the unheated object. These properties may be estimated through a full inverse scattering treatment (for example, BIM, DBIM, and the like), that simultaneously estimates the total fields. Alternatively, the object properties may be inferred (for example, from an MRI study) after which the total fields are computed with one pass of a full-wave solver that captures object cavity scattering interactions. In general, the DBA is preferred because DBA is the appropriate approximation for differential scattered field measurements. For simplicity, the BA is used in the experiments described below, which show that the BA yields reasonable results.

F. Precomputed Linear Inverse Scattering Solution

The crux of real-time quantitative imaging is precomputing the inverse scattering solution. This may be done with a fixed field approximation, such as before. Linearization consists of discretizing the integral equation, after which the object is estimated by comparing forward model predictions to differential scattered field measurements. The cost function used to measure the difference between forward model predictions and data is:

$$F(M) = \|Gm - d\|_D^2 + \|m\|_M^2 \qquad \text{Equation (15)}$$

The vector norms $\|\cdot\|_D^2$ and $\|\cdot\|_M^2$ are defined by the inverse data and model covariance operators, $C_D^{-1}$ and $C_M^{-1}$, respectively. G is the discretized linear forward operator, the vector d contains S-parameter measurements, and m is a complex vector of pixels of the differential object.

The least squares solution of Equation (15) in matrix form is:

$$\tilde{m}=(G^*C_D^{-1}G+C_M^{-1})^{-1}G^*C_D^{-1}d \quad \text{Equation (16)}$$

where $\tilde{m}$ is the object estimate. When the data and image pixels are separately independent, and the noise and pixel uncertainties are constant, the inverse covariance matrices are scalars equal to $1/\sigma_d^2$ and $1/\sigma_m^2$, respectively. Equation (16) reduces to:

$$\tilde{m}=(G^*G+\lambda^2I)^{-1}G^*d \quad \text{Equation (17)}$$

which is the familiar regularized normal equations solution with Tikhonov parameter $\lambda=\sigma_d/\sigma_m$. Given an SVD decomposition G=USV*, Equation (17) may be written:

$$\tilde{m}=Md \quad \text{Equation (18)}$$

where:

$$M=V(S^2+\lambda^2I)^{-1}SU^* \quad \text{Equation (19)}$$

The matrix M, once computed and stored, is applied in real-time to d to obtain a new object estimate.

G. Real-time Data Processing

Labview and Matlab may be used in tandem to collect the scattered field measurements and process and display images in real-time. Labview controls the VNA and the switches and Matlab processes the data and computes the image. The VNA is triggered to save a single data stream as the switches cycle through every T/R pair. Matlab actively checks for new data files and then segments the data stream and produces the image.

1) VNA data stream: All pair-wise scattering parameters are collected by the VNA in a single measurement. The VNA triggers a 4000 point, 2.1 second CW measurement at 915 MHz with an IF bandwidth of 2 kHz. The switches are cycled through all 324 T/R combinations throughout the duration of the measurement to produce a data stream of S-parameters for all T/R combinations. 6 milliseconds per path yields approximately 10 points per T/R pair. In actuality, the VNA triggers twice: the first trigger sources Port 1 to record $S_{11}$ and $S_{21}$, the second trigger sources Port 2 to record $S_{22}$ and $S_{12}$. As a result, the switches are cycled twice, and an entire data set is collected every 4 seconds. Because the data stream is a single measurement and captures the response of all T/R paths, S-parameter error correction must be turned off and applied in post-processing.

Figure 7A:
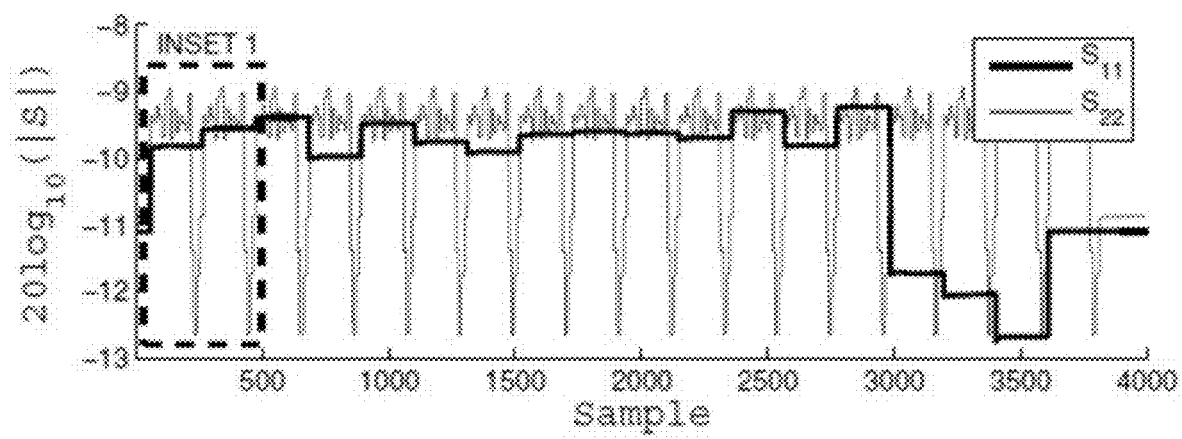
FIG. 7A is a graph of VNA data stream of a single 2-port S-parameter measurement while the switching matrix cycles over all 324 T/R combination, sweep is 4000 points, 2.1 seconds, at 915 MHz including $S_{11}$ (transmitters) and $S_{22}$ (receivers).
Figure 7B:
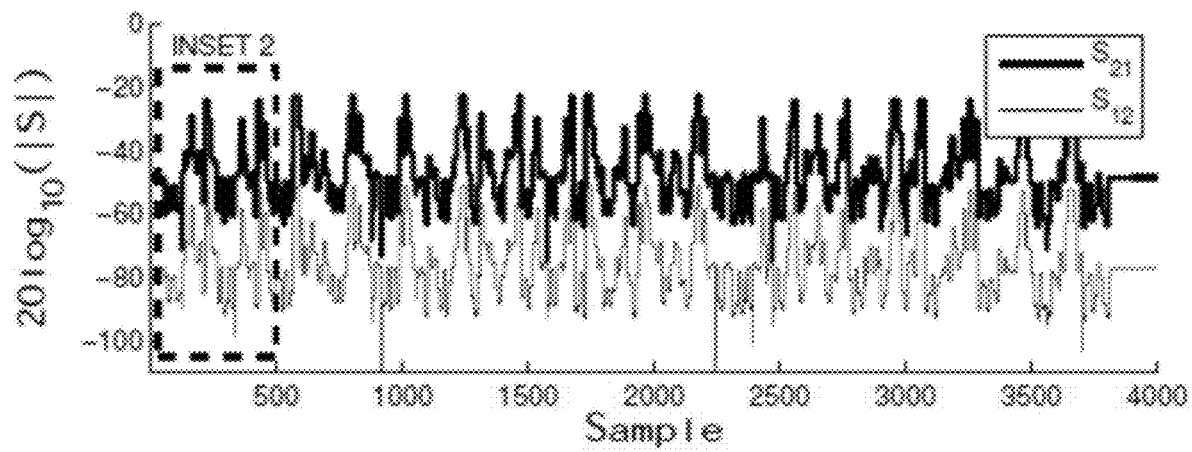
FIG. 7B is a graph of VNA data stream of a single 2-port S-parameter measurement while the switching matrix cycles over all 324 T/R combination, sweep is 4000 points, 2.1 seconds, at 915 MHz including $S_{21}$ and $S_{12}$ (30 dB differential from RCVR bypass).
Figure 7C:
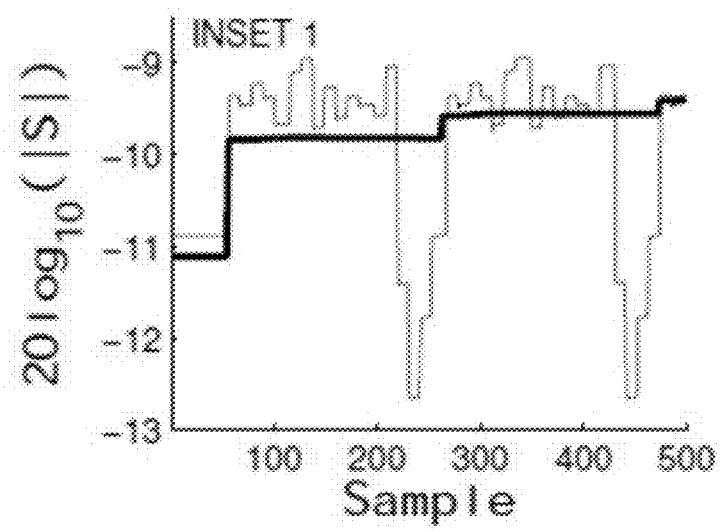
FIG. 7C illustrates an inset of FIG. 7A.
Figure 7D:
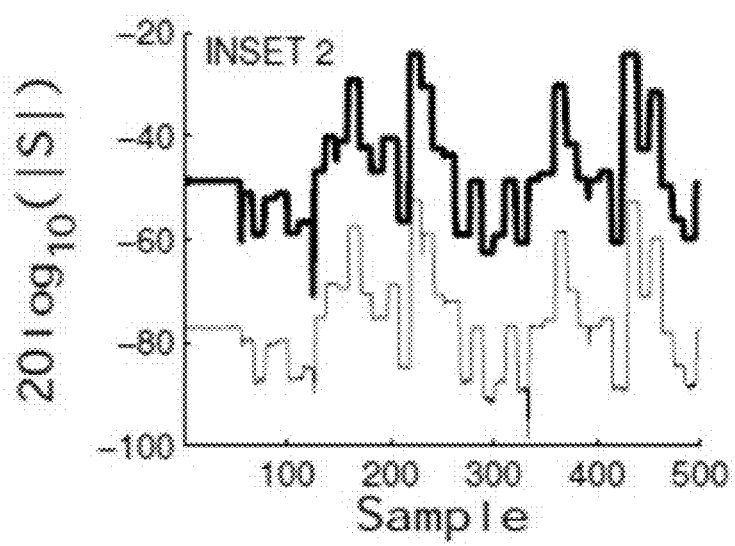
FIG. 7D illustrates an inset of FIG. 7B.

FIGS. 7A-7D show the magnitude of a raw incident field data stream of all four S-parameters. $S_{22}$ and $S_{12}$ are retrospectively aligned with $S_{11}$ and $S_{21}$. $S_{11}$ is measuring the reflection coefficients of the transmit antennas, while $S_{22}$ measures the reflection coefficients of the receive antennas. Receivers are cycled per transmitter, hence the 18×18 nested pattern in FIG. 7A. Lower reflection coefficient magnitudes are due to longer uncorrected paths through the SPDT Minicircuits switches. FIG. 7B shows $S_{21}$ and $S_{12}$. $S_{21}$ is approximately 30 dB higher than $S_{12}$, due to the power level asymmetry created by the Port 2 RCVR coupler bypass and the fact that error correction is off. FIG. 7C shows the inset of FIG. 7A and FIG. 7D shows the inset of FIG. 7B.

2) S-parameter error correction: As mentioned, error correction is turned off during the sweep and applied after segmentation (below). The 12-term error model is shown below. Given uncorrected 2-port measurements $S_{11m}$, $S_{21m}$, $S_{12m}$, and $S_{22m}$, the corrected S-parameters computed with the standard 12-term error model are:

$$S_{11} = \frac{A[1+e'_{22}D]-e_{22}BC}{E} \quad \text{Equation (20)}$$

$$S_{21} = \frac{B}{E}[1+(e'_{22}-e_{22})D] \quad \text{Equation (21)}$$

$$S_{12} = \frac{C}{E}[1+(e'_{11}-e_{11})A] \quad \text{Equation (22)}$$

$$S_{22} = \frac{D[1+e_{11}A]-e'_{11}BC}{E} \quad \text{Equation (23)}$$

where:

$$A = \frac{S_{11m}-e_{00}}{e_{10}e_{01}} \quad \text{Equation (24)}$$

$$B = \frac{S_{21m}-e_{30}}{e_{10}e_{32}} \quad \text{Equation (25)}$$

$$C = \frac{S_{12m}-e_{03}}{e_{23}e_{01}} \quad \text{Equation (26)}$$

$$D = \frac{S_{22m}-e_{33}}{e_{23}e_{32}} \quad \text{Equation (27)}$$

$$E = [1+e_{11}A][1+e'_{22}D]-e_{22}e'_{11}BC \quad \text{Equation (28)}$$

For convenience, Table I lists the error terms and their corresponding SCPI designations in Agilent PNA-type network analyzers at the time of publication.

TABLE 1

| Error Term | Description | VNA SCPI Name |
|---|---|---|
| $e_{00}$ | Directivity(1,1) | EDIR,1,1 |
| $e_{33}$ | Directivity(2,2) | EDIR,2,2 |
| $e_{11}$ | SorceMatch(1,1) | ESRM,1,1 |
| $e'_{22}$ | SourceMatch(2,2) | ESRM,2,2 |
| $e'_{11}$ | LoadMatch(1,2) | ELDM,1,2 |
| $e_{22}$ | LoadMatch(2,1) | ELDM,2,1 |
| $e_{10}e_{01}$ | ReflectionTracking(1,1) | ERFT,1,1 |
| $e_{23}e_{32}$ | ReflectionTracking(2,2) | ERFT,2,2 |
| $e_{10}e_{32}$ | TransmissionTracking(2,1) | ETRT,2,1 |
| $e_{23}e_{01}$ | TransmissionTracking(1,2) | ETRT,1,2 |
| $e_{30}$ | CrossTalk(1,2) | EXTLK,1,2 |
| $e_{03}$ | CrossTalk(2,1) | EXTLK,2,1 |

The error terms for all T/R 2-port calibrations are downloaded with Labview using Agilent VNA-SCPI commands. The 12-term model was cross checked against VNA-calibrated data sets, including those from the unknown thru tests, with identical results.

Technically, all four S-parameters are required in the 12-term error model, but for imaging only $S_{21}$ was used. In the equation for corrected $S_{21}$, the contribution of $S_{12}$ is third order, so it is safely set to zero since it is already 30 dB lower. In future work, the possibility of treating $S_{11}$ and $S_{22}$ as constant in differential scattering scenarios to reduce data collection time may be investigated. In initial tests not described herein, the data collection has been refined to less than one second.

3) Data stream segmentation: After a new data set is detected and loaded by Matlab, the data streams for $S_{11}$, $S_{21}$, and $S_{22}$ are segmented to extract individual T/R measurements as follows:

1) Separate real and imaginary parts.
2) Apply a fast 1D Total Variation (TV) filter. This preserves the block-like pattern of the data stream while smoothing the steps.
3) Compute the next-neighbor discrete difference. Take the absolute value. Spikes denote segment transitions. The TV filter is necessary to prevent noise from corrupting this step.

4) Threshold the combined discrete differences of the real and imaginary parts.

5) Check for 324 segments; discard the data set if fewer are detected.

6) Average the points within a segment, excluding transitions.

7) Apply error correction to the segmented T/R data (e.g., the 12-term model).

8) Correct the $S_{21}$ phase ambiguity with the HFSS model (correction is predetermined).

Figure 8A:
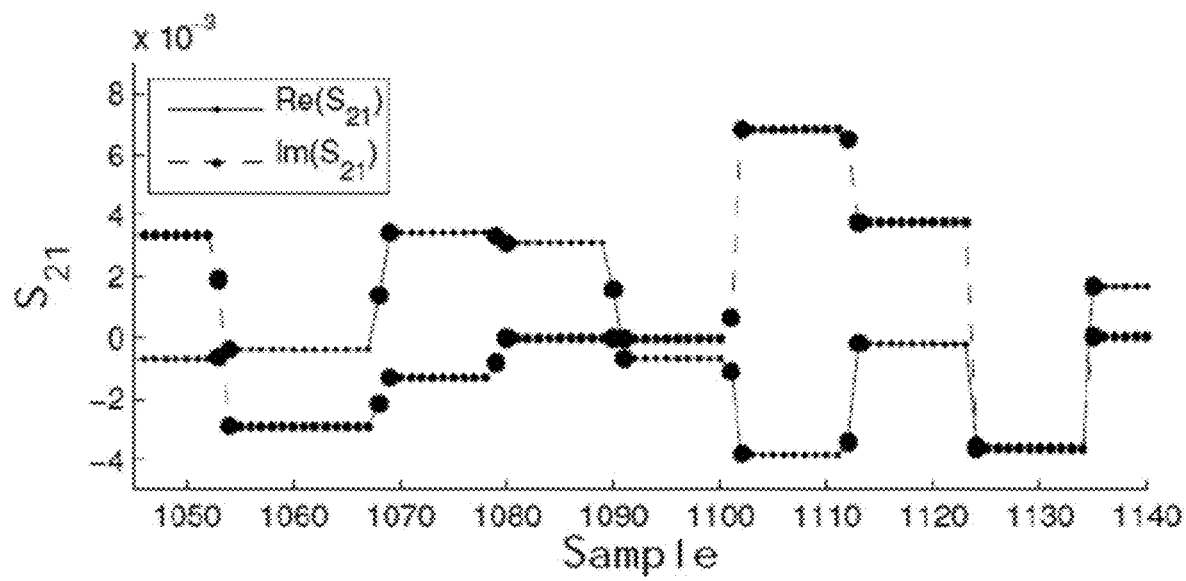
FIG. 8A illustrates an example of segmentation including real and imaginary parts of $S_{21}$, large circles are transition samples.
Figure 8B:
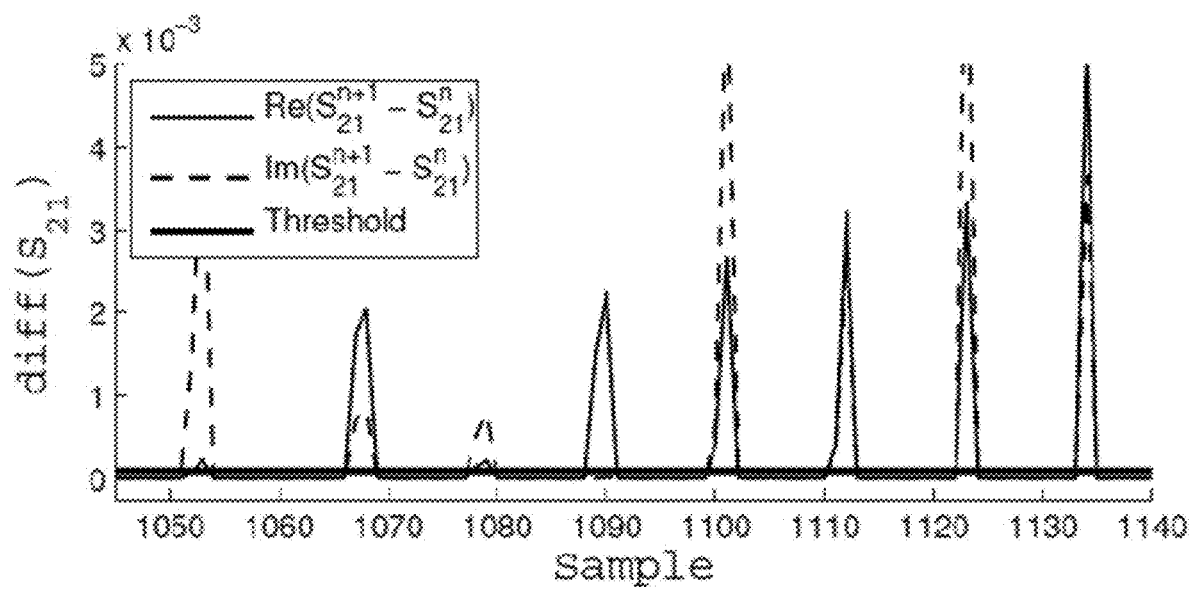
FIG. 8B illustrates an example of segmentation including threshold of absolute value of next-neighbor discrete difference.

FIG. 8A illustrates the segmentation of the real and imaginary parts of a portion of the S21 data stream. Transition points are highlighted and excluded. FIG. 8B shows the absolute value of the next-neighbor discrete differences with the threshold. The threshold was chosen by trial and error.

Because segmentation is based on a discrete-difference, segmentation is robust to timing inconsistencies. This is important because the exact number of points per segment may vary due to VNA triggering, CPU allocation, or parallel port signaling. However, segmentation is now sensitive to noise, hence the need for the TV filter. Also, counting errors may occur when two adjacent data are exactly the same. Practically speaking, this is rare and usually due to bit errors, and may be handled in future versions of this system.

After segmentation and error correction, data are mapped to the vector d in Equation (18) and a new image is formed by multiplying the data with the precomputed inverse scattering solution. The entire post-processing and image formation sequence takes a fraction of a second.

Figure 23:
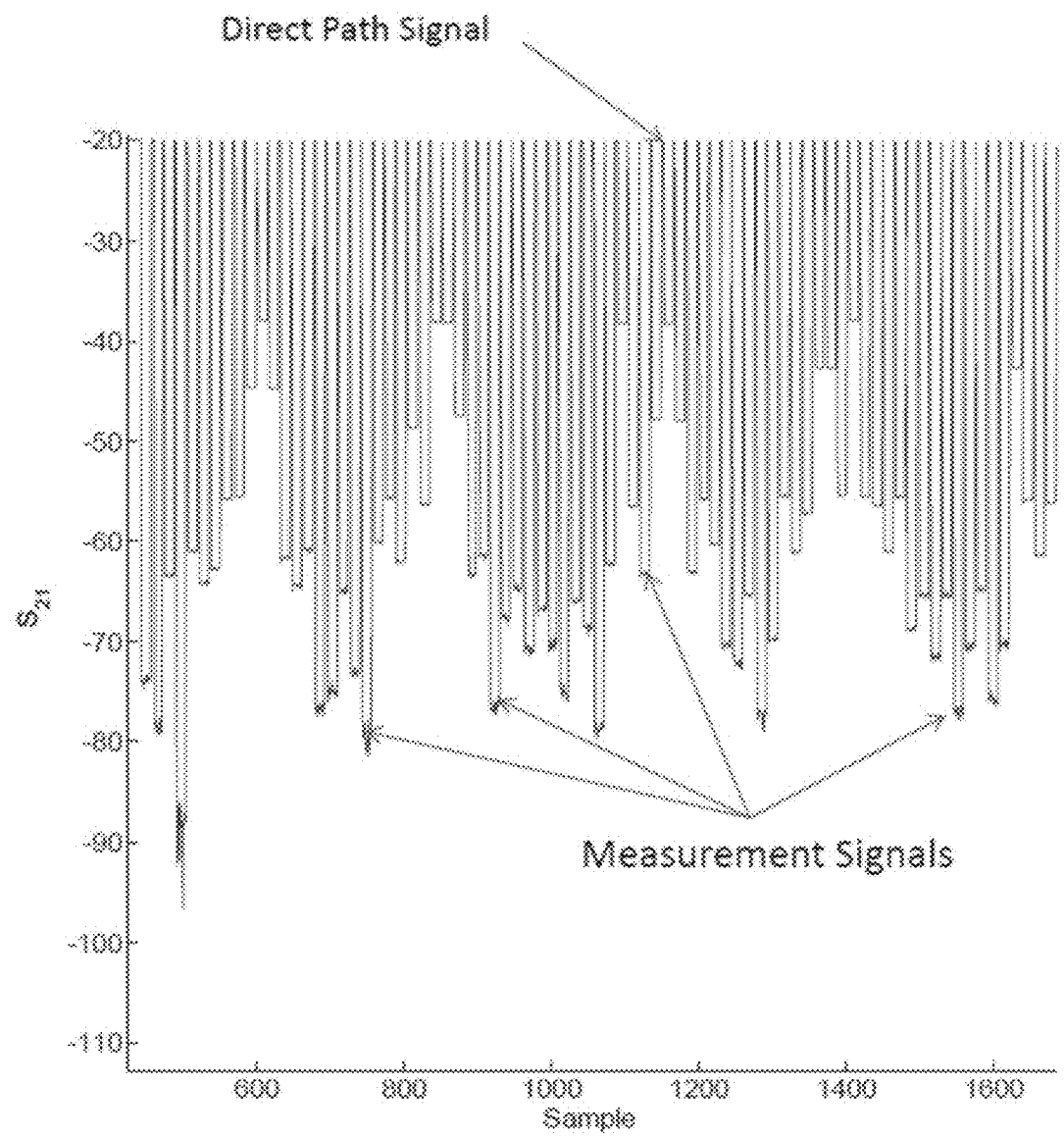
FIG. 23 graphically illustrates samples taken with a hybrid data stream segmentation method.

A new data stream segmentation method has also been developed that provides improved reliability and increased speed. This method employs a hybrid hardware/software solution that allows for simple magnitude thresholding to accurately determine each transition between individual antenna pair measurements within the data stream. The hardware component involves employing an additional switching channel that is a direct connection between the transmit switching system and the receiving switching system (bypassing the imaging cavity). This direct connection results in a much higher magnitude received signal (>20 dB) than any of the antenna pair measurements (see FIG. 23). By switching to this direct hardware path between each successive antenna pair measurement, it is possible to implement a very robust and fast parsing scheme using straight magnitude thresholding (for example, whenever the received signal exceeds a certain magnitude threshold, a switch is known to occur).

Results and Discussion

The target used to create a differential change in dielectric properties due to a change in temperature is a 4 cm diameter ping-pong ball that is filled with water and sealed. This is meant to emulate the size and shape of a thermal therapy focal spot in this cavity at 915 MHz, which is approximately 3 cm in diameter. The target is heated to approximately 55° C. in a water bath and then placed in the cavity and imaged while the target cools.

Figure 9A:
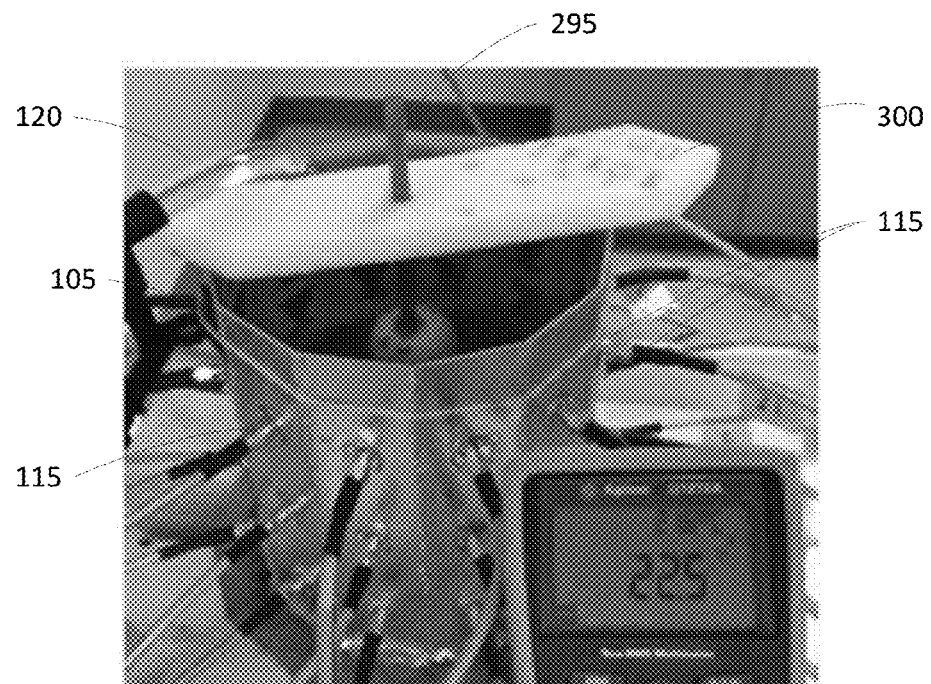
FIG. 9A illustrates a control target: water-filled ping-pong ball with embedded thermistor, shown here cooling in the cavity from approximately 55° C. to 22.5° C.

The target is held with a thin plastic straw and suspended from a piece of rigid, low-dielectric ROHACELL foam as shown in FIG. 9A. As a control, the change in temperature may be measured with an embedded thermistor as the target cools to the ambient cavity temperature of about 22.5° C., the plot is shown FIG. 9B. In reality, the time-dependent temperature profile of the target is more complicated than may be represented by a single thermistor measurement. Improvements to this method are listed in the conclusion section.

In the examples that follow, the thermistor is removed and it is assumed that the target cools at the same rate as the control. Also, the heated object at time zero is taken as the background object. Thus, a differential change in dielectric properties as the target goes from a higher temperature to lower temperature may be tracked. This is the reverse of what occurs in most thermal therapy systems. This may be done for experimental convenience since the temperature dependence of dielectric constant of water remains the same whether the water heats up or cools down, which may be detected as an overall change in scattering contrast.

In addition, although the inversion estimates complex $\Delta O(r)$, images of $|\Delta O(r)|$. This is because $|\Delta O(r)|$ is a measure of the overall change in scattering contrast relative to the background. It avoids ambiguity in simultaneous inversion of both relative permittivity and conductivity, without the need to assert stringent a priori relations between them. In its current form, the inversion obtains the correct sign of the complex contrast for non-differential images of simple targets. For differential imaging and the BA, the inversion may split the scattering contribution differently between the two properties for different objects. This issue may be improved upon in future versions. Despite this, the relation between $|\Delta O(r)|$ and the total scattered field power is conserved through the L2 norm of the cost function. Thus, it is theoretically sufficient to correlate $|\Delta O(r)|$ with temperature to accomplish differential thermal monitoring provided that the contrast changes. This is verified empirically in the following examples.

In all the examples that follow, 3D images of $|\Delta O(r)|$ are computed every 4 seconds, pixelated at 2 mm. The imaging regions are cylindrical, and the images are not interpolated.

Figure 10:
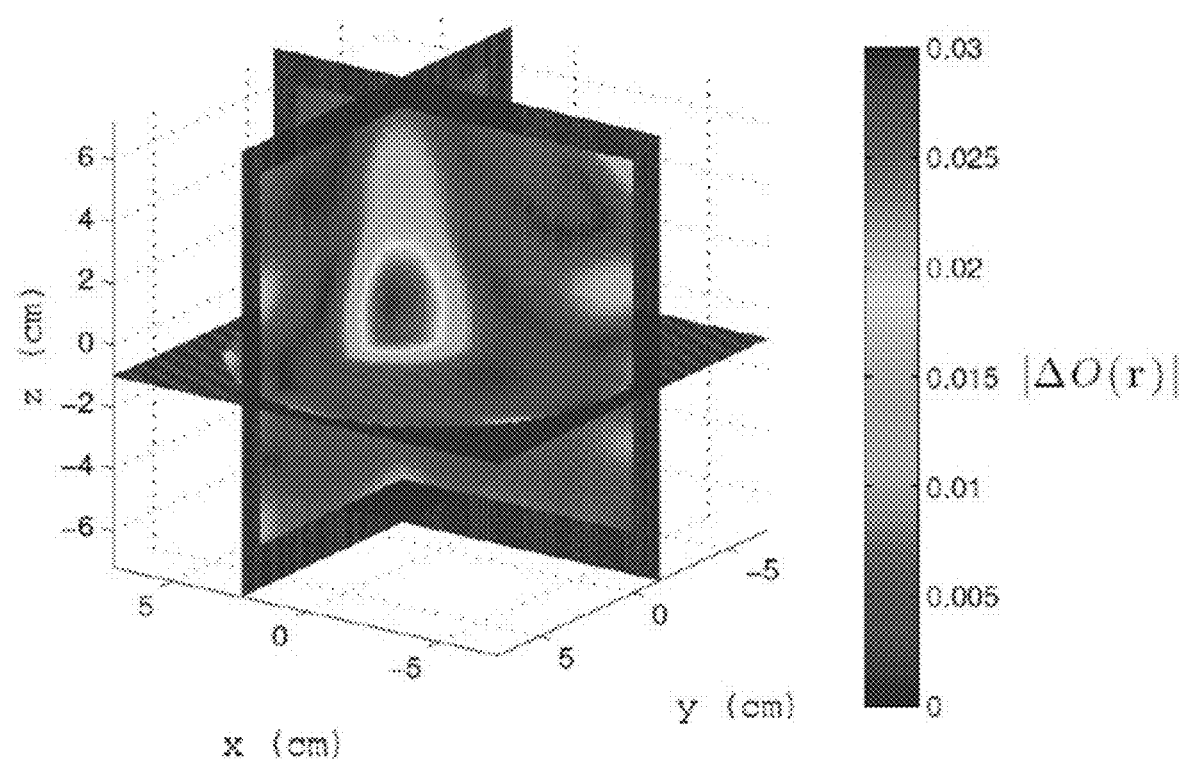
FIG. 10 illustrates an image of $|\Delta O(r)|$ after the target has cooled from 55° C. to 22.5° C., the initial heated object is taken as the background object at time zero.
Figure 11:
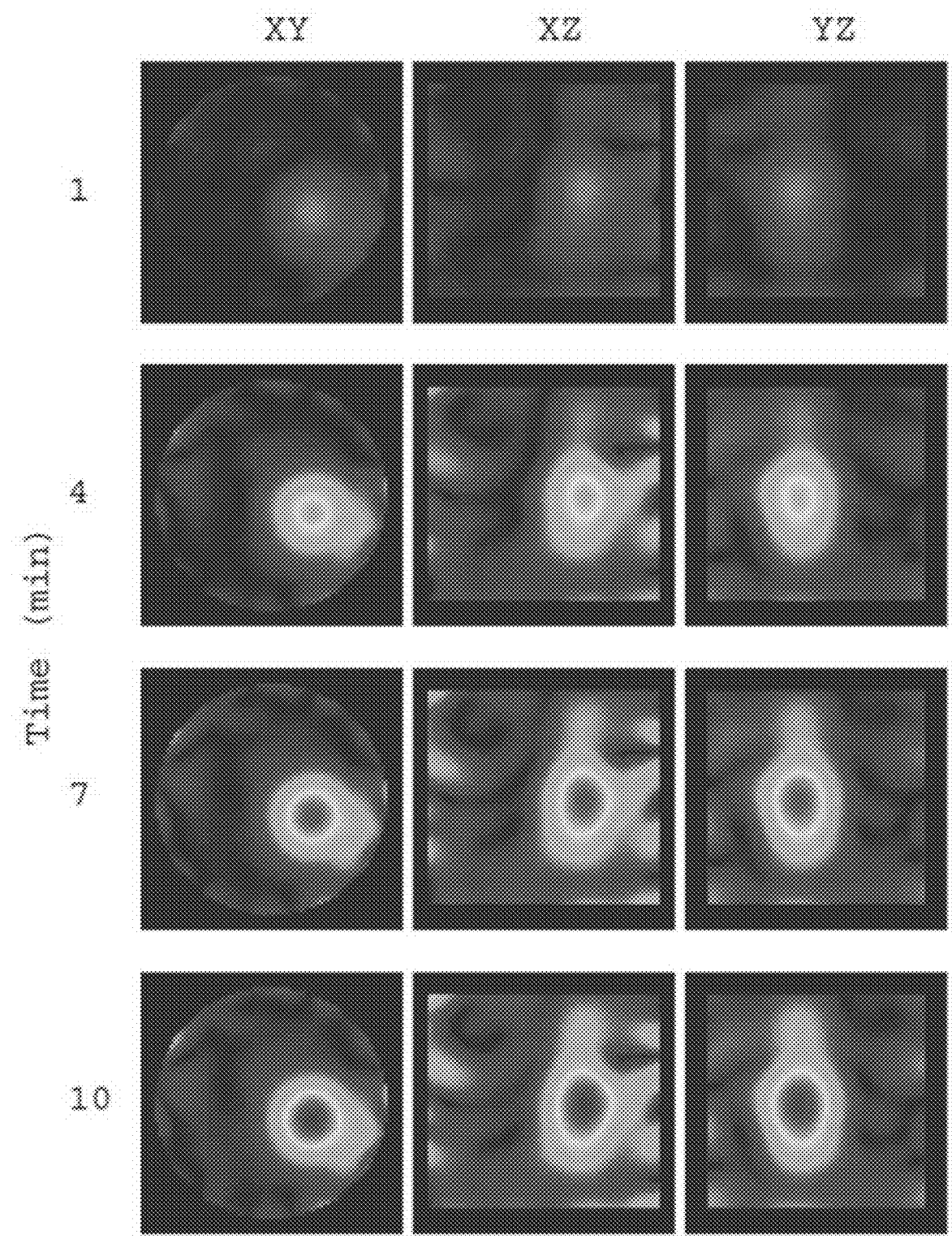
FIG. 11 illustrates the time series of $|\Delta O(r)|$ for the water target of FIG. 10 as it cools from 55° C. to 22.5° C. over 10 minutes, the images are formed every 4 seconds, the heated sphere at time zero is taken as the background object, and cuts are through the peak contrast.

Example 1: One 4 cm isolated water-filled ping-pong ball is imaged as the ball cools from 55° C. to about 22.5° C. This is the same ball as shown in FIG. 9A without the thermistor. The heated ball is taken as the background object and the BA is appropriate for the field estimate. A 3D slice view of the final image in the sequence, after the ball has reached the ambient cavity temperature, is shown in FIG. 10. This represents the maximum differential change in the scattering contrast. A time series at {1,4,7,10} minutes is shown in FIG. 11. The magnitude of the contrast clearly increases and settles after 10 minutes. The sphere is well resolved, demonstrating a resolution of 3-4 centimeters, which is on the order of the thermal therapy focal spot size in this cavity.

Figure 12A:
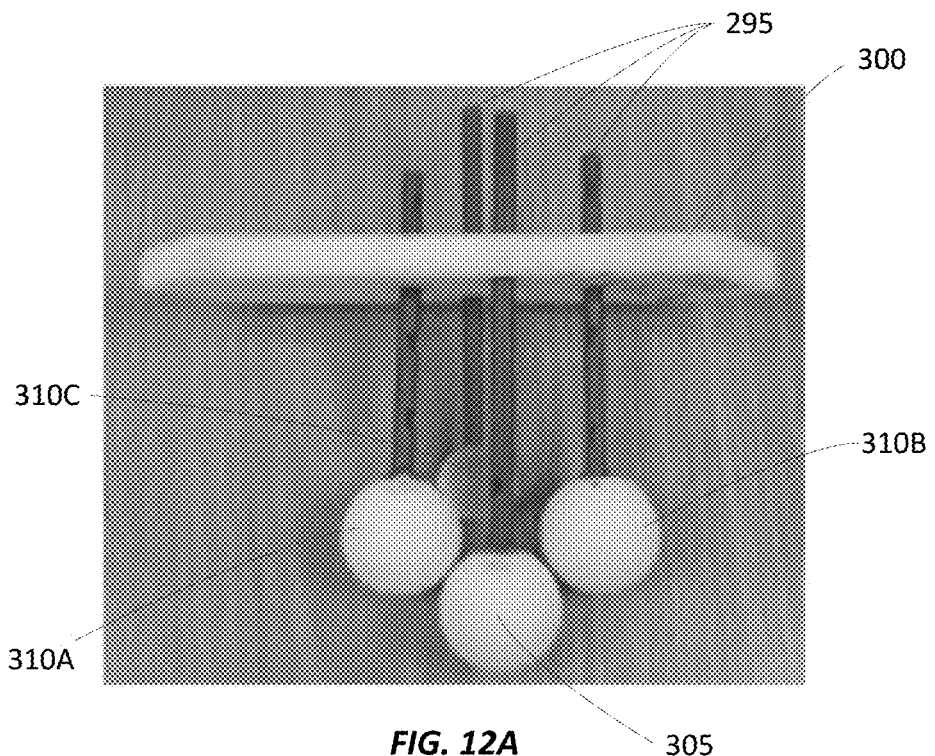
FIG. 12A illustrates cluster of four targets where only the left target is heated.
Figure 12B:
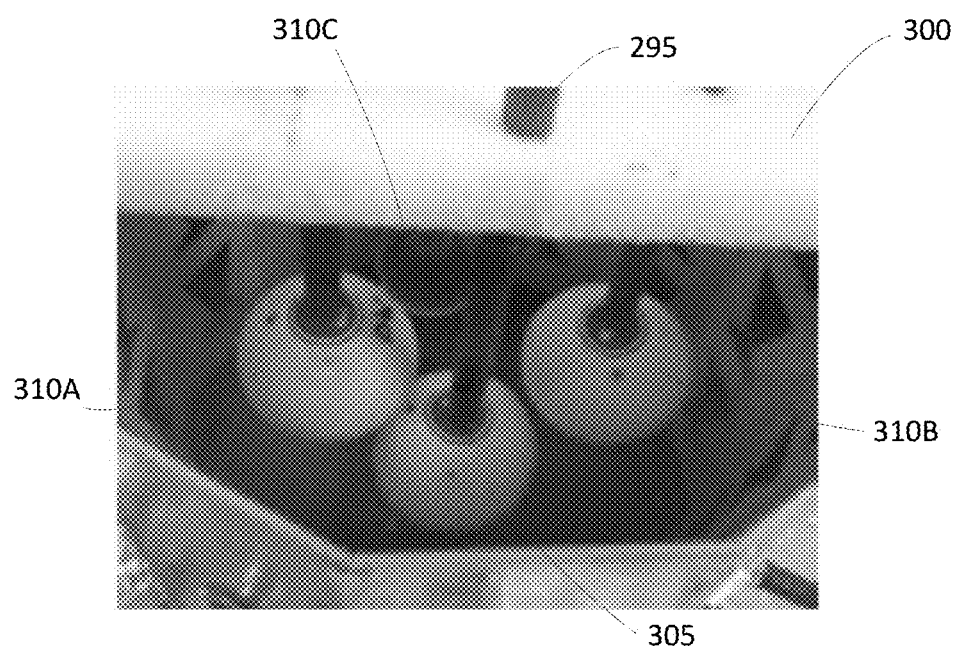
FIG. 12B illustrates targets in the cavity.
Figure 12C:
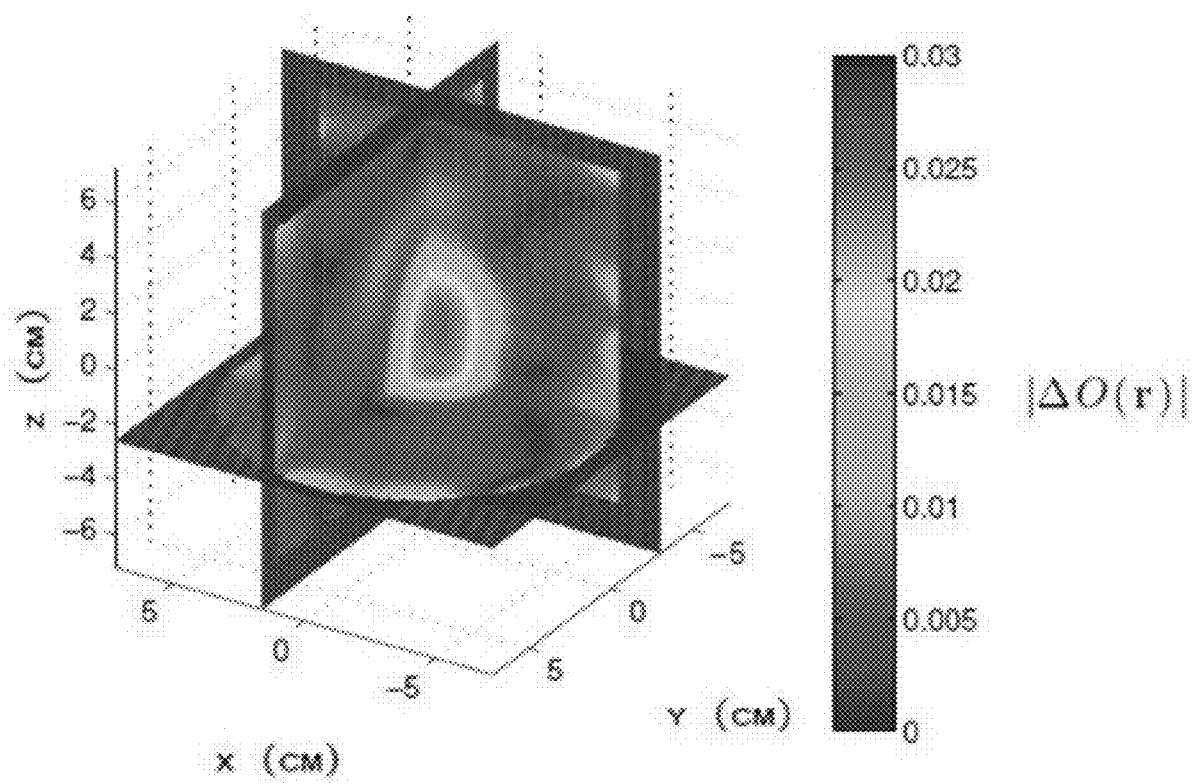
FIG. 12C illustrates $|\Delta O(r)|$ after the water target in the clutter has cooled from 55° C. to 22.5° C., the cluster with heated target is taken as the background object at time zero.
Figure 13:
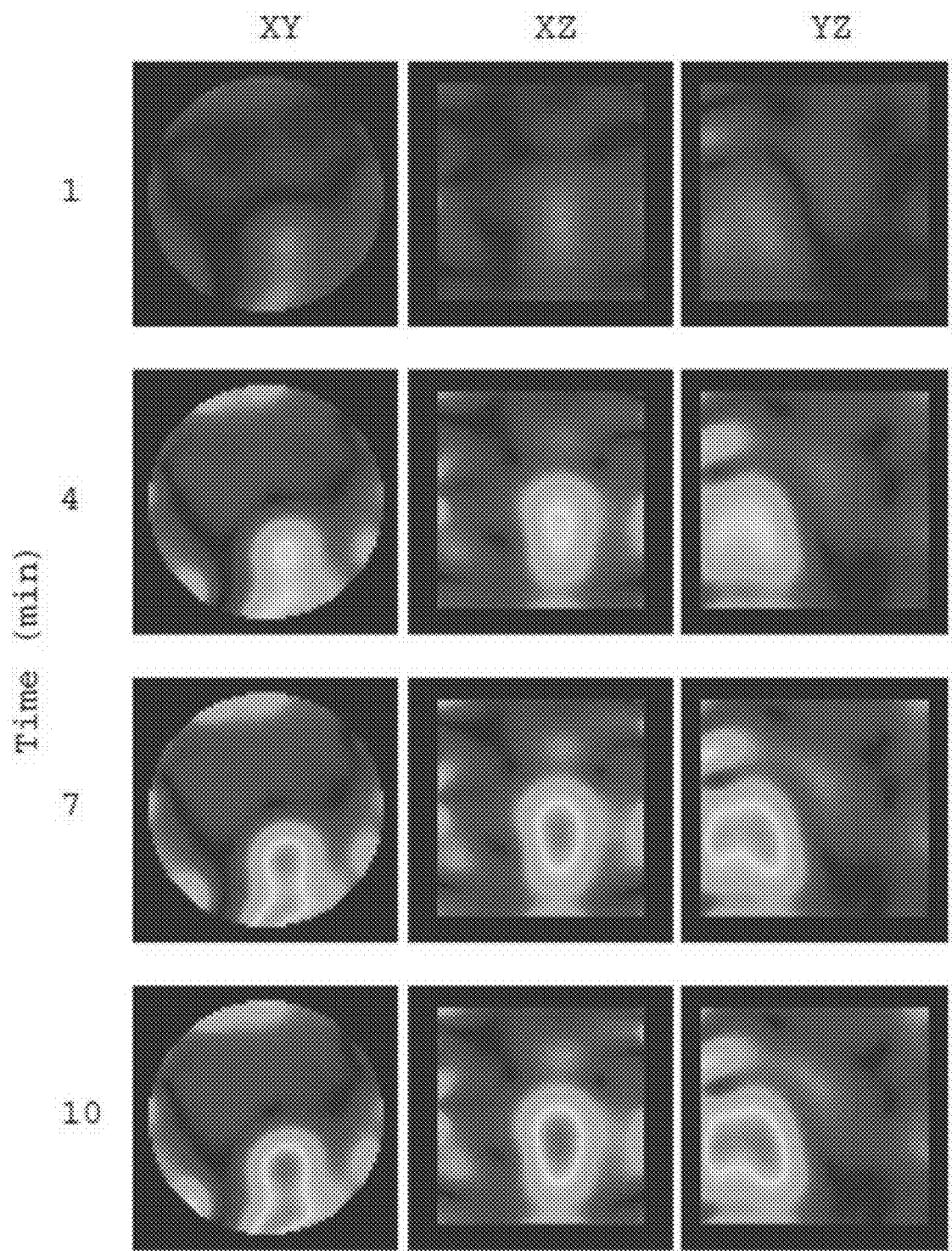
FIG. 13 illustrates the time series of $|\Delta O(r)|$ for the water target in clutter of FIG. 12C as it cools from 55° C. to 22.5° C. over 10 minutes, cuts are through the peak contrast.

Example 2: The same 4 cm water-filled ping-pong ball is heated and imaged as it cools while in the presence of three other objects. These objects consist of two water filled ping-pong balls and a 1 inch diameter acrylic sphere that act as clutter shown in FIG. 12A. Again the BA is used for the fields. This example is meant to test how well the differential contrast can be detected under the BA in the presence of clutter. A 3D slice of the final image and its time series are shown in FIGS. 12C and 13, respectively. The change in contrast with temperature is clearly visible. The peak contrast is slightly lower than Example 1 and more artifacts are present. The artifacts are likely due to decreased accuracy of the BA as well as the fact that the imaging domain encroaches on the near-field of the antennas, where fields have high spatial gradients. The latter effect may be reduced with a larger diameter cavity. Overall, this shows that a change in temperature may be imaged in the presence of clutter and that the differential measurement successfully subtracted most of the unwanted object scattering.

Figure 14A:
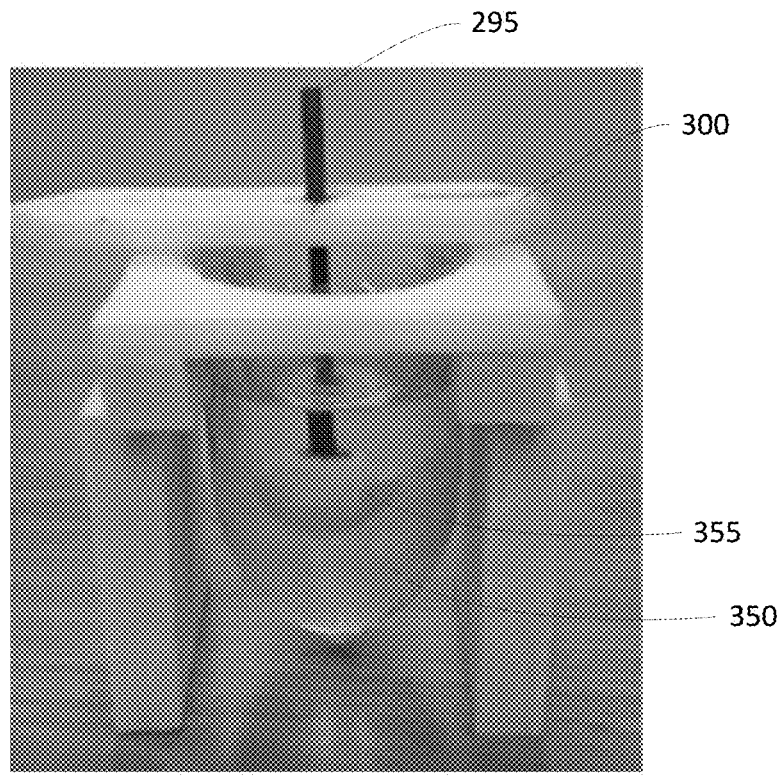
FIG. 14A illustrates a double chambered breast phantom with vegetable oil and coupling fluid, the heated target placed in inner chamber.
Figure 14B:
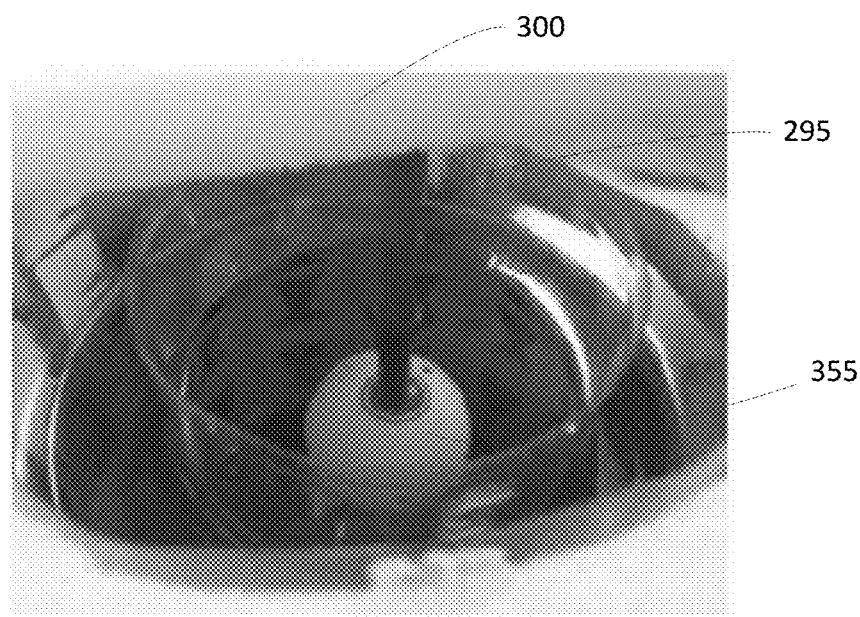
FIG. 14B illustrates the breast phantom of FIG. 14A in the cavity.
Figure 14C:
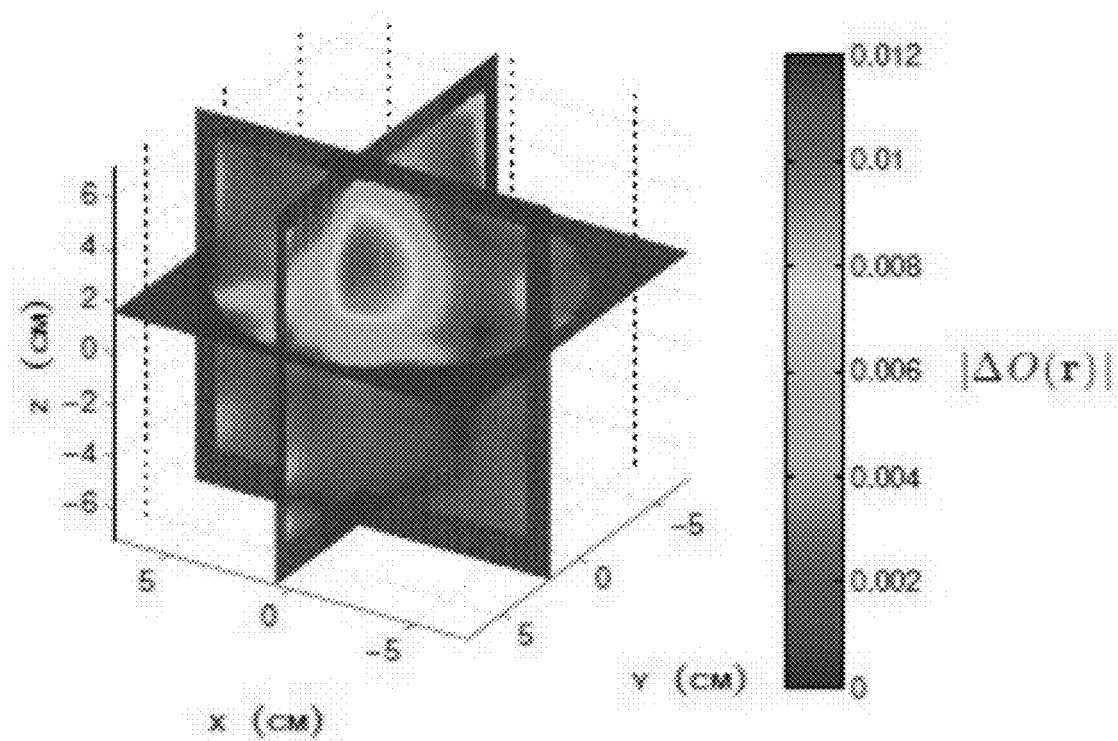
FIG. 14C illustrates $|\Delta O(r)|$ after the water sphere has cooled, only differential temperature is detected.
Figure 15:
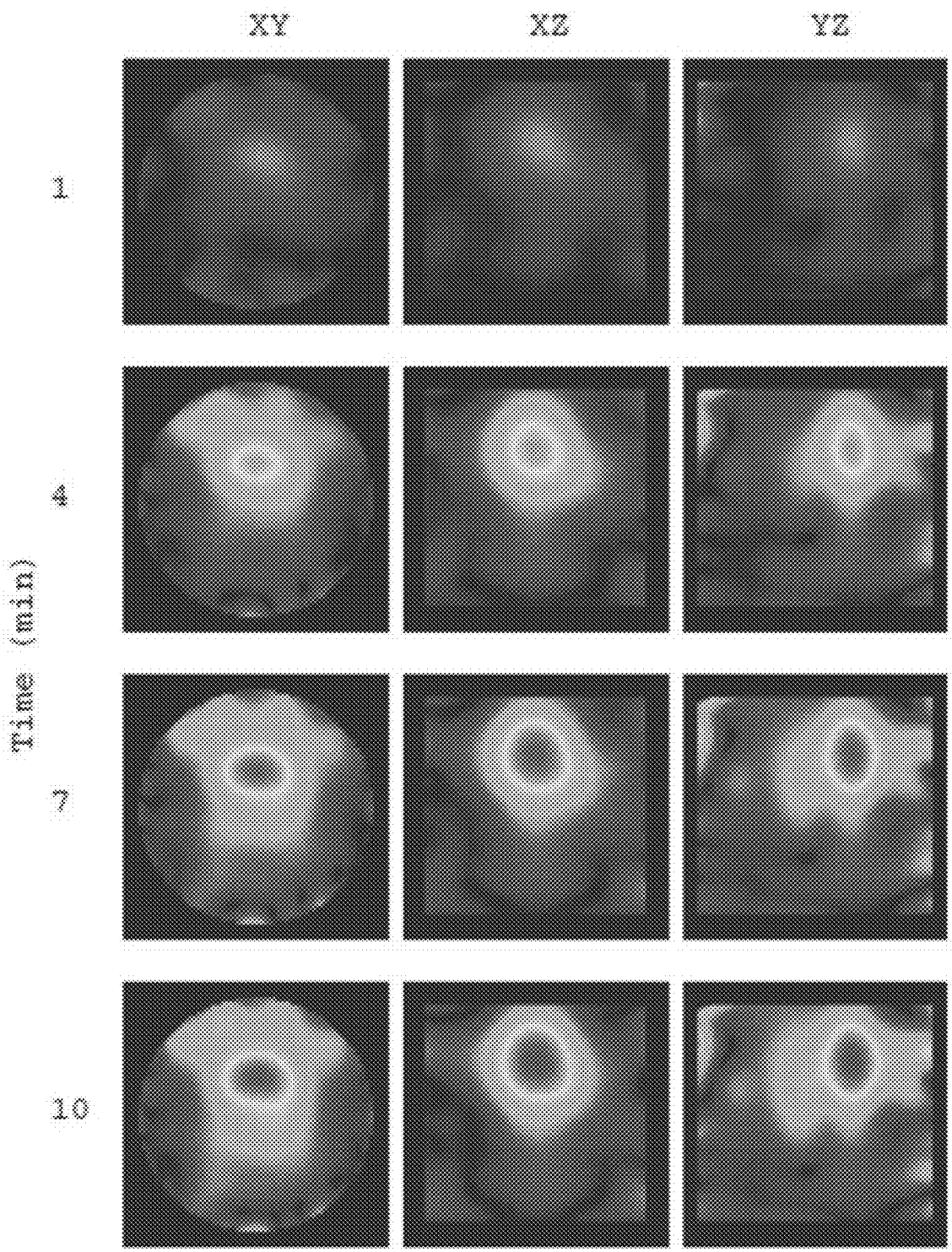
FIG. 15 illustrates the time series of $|\Delta O(r)|$ for the phantom of FIG. 14C, phantom and heated target are taken as the background object at time zero, cuts are through the peak contrast.

Example 3: The final example is a simple breast phantom with heated target, as shown in FIGS. 14A-14B. The phantom consists of two plastic bottles creating inner and outer chambers. The inner chamber is filled with the cavity fluid, meant to mimic the dielectric properties of glandular breast tissue. The outer chamber is filled with vegetable oil to mimic the lower dielectric properties of fatty breast tissue. A 3D slice view of the final image and the time series are shown in FIGS. 14C and 15. The target and time-varying contrast are clearly distinguishable. The peak magnitude is slightly lower than that in Examples 1 and 2. Similar to Example 2, the decrease in contrast magnitude and target blurring is attributed to decreased accuracy of the BA, with the additional possibility that the heat from the object is not convected from the immediate surroundings of the target as the target was in the other examples. Still, the ability of the differential formulation to successfully subtract the background scattering of the phantom is apparent. It also demonstrates that the BA is actually sufficient for an object where the BA is otherwise expected to fail. Thus, it is reasonable to conclude that the system, as described herein, has met the requirements for practical thermal monitoring.

Figure 9B:
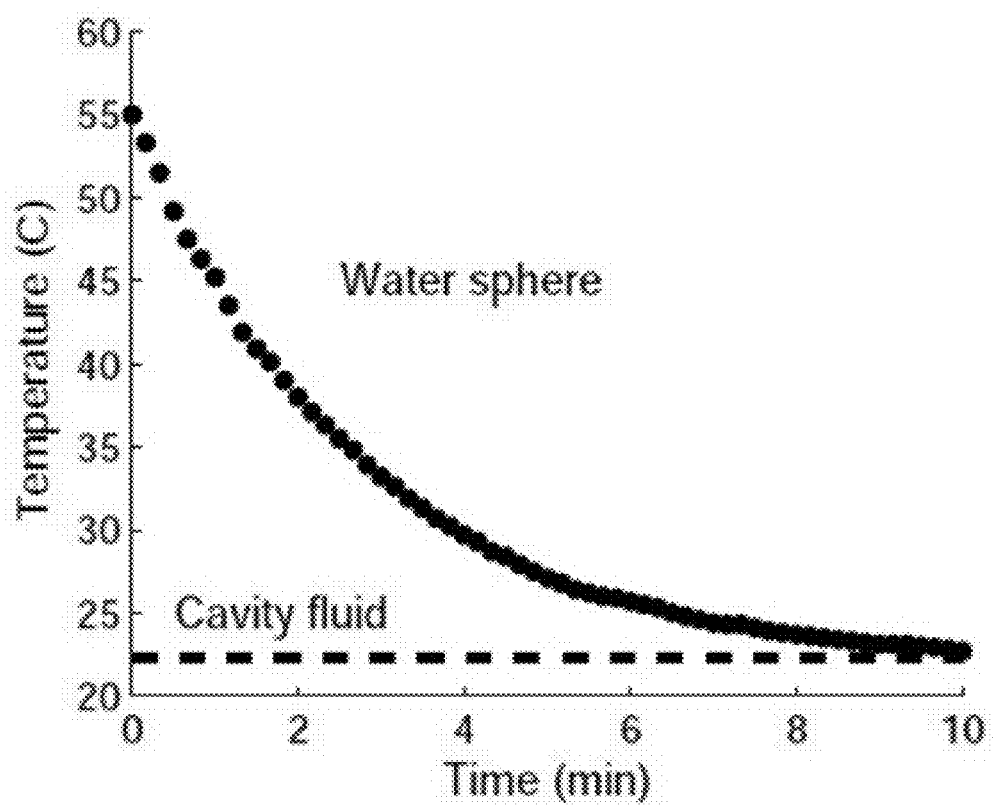
FIG. 9B illustrates a plot of ping-pong ball control target temperature vs. time in the cavity, the dotted line is the ambient temperature of the cavity fluid of 22.5° C.
Figure 16:
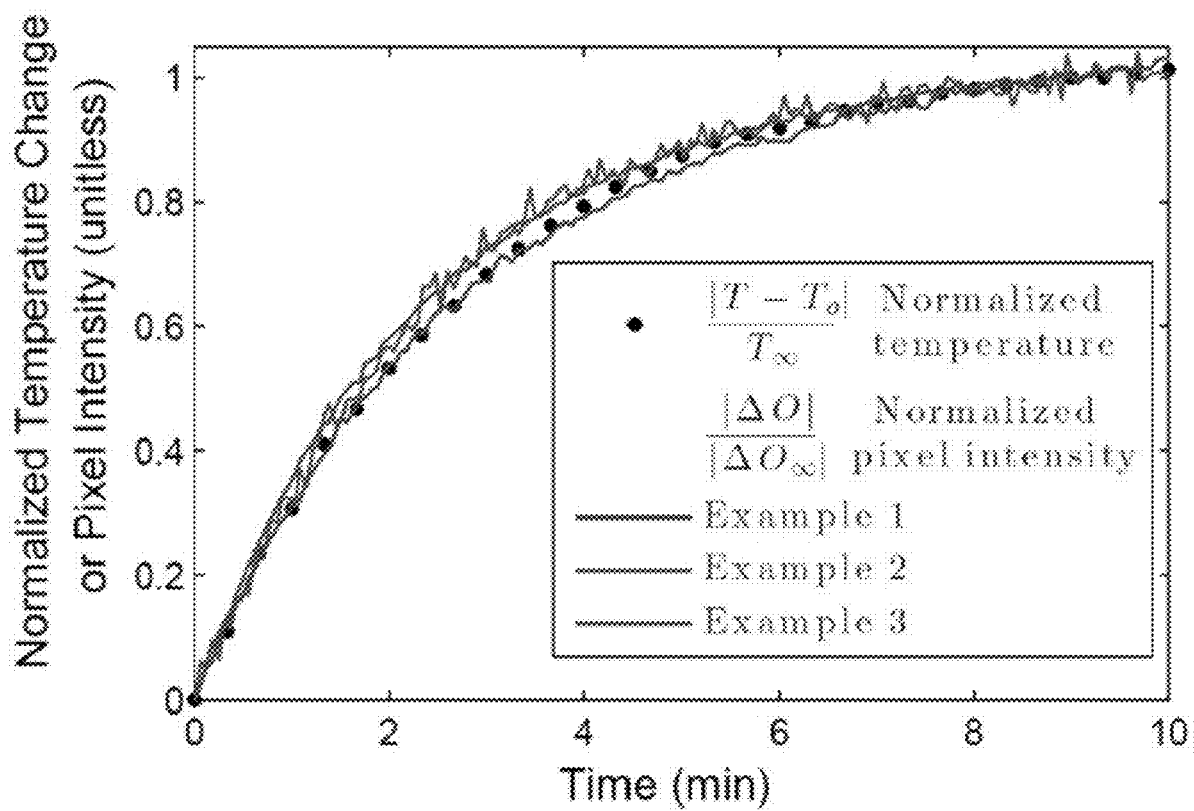
FIG. 16 is a graph of normalized pixel intensity at the center of the detected target in FIGS. 11, 13, and 15 at every time step plotted against the normalized temperature of the control target in FIG. 9B, pixel intensity rate of change tracks 1:1 with temperature.

To correlate the image with temperature, the pixel intensity at the center of the detected target in each example over time may be compared against the temperature curve of the control target in FIG. 9B. The curves may be normalized in order to compare the rates of change with time. Again, complete images are formed every 4 seconds, from which the pixel of peak contrast may be taken. As shown in FIG. 16, the scattering contrast of all three targets correlates nearly 1:1 with temperature as function of time. It may be infer from these plots that the change in scattering contrast of water is nearly linear with temperature in the range of hyperthermia temperatures. Furthermore, this relation is observed across all of the imaged scenarios (for example, sphere, clutter, phantom, and the like), despite using the BA for the field estimate.

To determine the temperature resolution, a fourth-order polynomial may be fit to each of the three pixel intensity curves of FIG. 16, and the standard deviations of the residuals may be computed. For Examples 1, 2, and 3, respectively, the standard deviations are $\sigma=0.0062$, 0.0045, and 0.0163. The temperature resolution is taken as $\Delta T=2\sigma|T_\infty-T_0|$. The temperature of the target ranges from approximately 55° C. to 22° C., thus it may be concluded that a temperature change in each case may be resolved to $\Delta T=0.41$, 0.30, and 1.1° C., respectively.

Monitoring and Control

Microwave imaging relies on temperature dependency of the dielectric properties of tissue rather than on temperature dependency of the proton resonance frequency of water molecules, replacing the need for MRI in thermal therapy monitoring and guidance. The embodiments described herein include hardware and software features for the successful implementation of real-time microwave thermal imaging. Alternatively or in addition, the embodiments described herein may be used to control a thermal treatment (for example, a microwave thermal treatment. The thermal treatment may be controlled automatically or manually by a user (for example, a medical professional).

Whereas prior implementations used the background electric field only, the embodiments described herein include full wave modeling of a thermal probe in the presence of a segmented anatomy. A robust parser uses a hybrid method (for example, a hybrid of hardware and software) to rapidly acquire microwave thermal imaging data. The hardware includes a through channel connection used as an embedded trigger signaling each discrete measurement within the continuous data stream. The software includes real-time magnitude thresholding to parse a continuous data stream into discrete measurement groups plus real-time median filtering within each measurement group to enhance signal-to-noise ratio (SNR).

A custom low-loss coupling medium is implemented to achieve the necessary SNR to accurately detect small changes in dielectric due to temperature. In some embodiments, the coupling medium is a low loss material with a controlled dielectric constant (for example, ECCOSTOCK® HiK), which has been custom machined to couple microwaves from the imaging cavity to a specific patient anatomy.

An adaptive imaging domain is used to improve accuracy and suppress artifacts. A user-selectable (or machine adaptive) region of interest for thermal imaging is based on prior knowledge of the treatment scenario.

Some advantages of the embodiments described herein include: (1) a higher frame rate possible than MRI monitoring for improved treatment guidance; (2) a lower cost; (3) a lower system complexity and material requirements; (4) a lower space requirement; and (5) a greater flexibility (for example, no MR compatibility requirement for treatment system).

Real-time microwave thermal monitoring requires knowledge of the tissue properties in the treatment region as well as any intervening tissues. Currently, this knowledge would need to be obtained using one of the standard clinical imaging methods (for example, MR, CT, and US). Imperfect knowledge of the tissue properties throughout the imaging volume may result in artifacts in the thermal image. Sources of error may include inaccuracies in mapping dielectric tissue data from prior imaging studies, as well as inaccuracies in image segmentation and image registration (including those due to patient motion during the procedure).

Figure 17A:
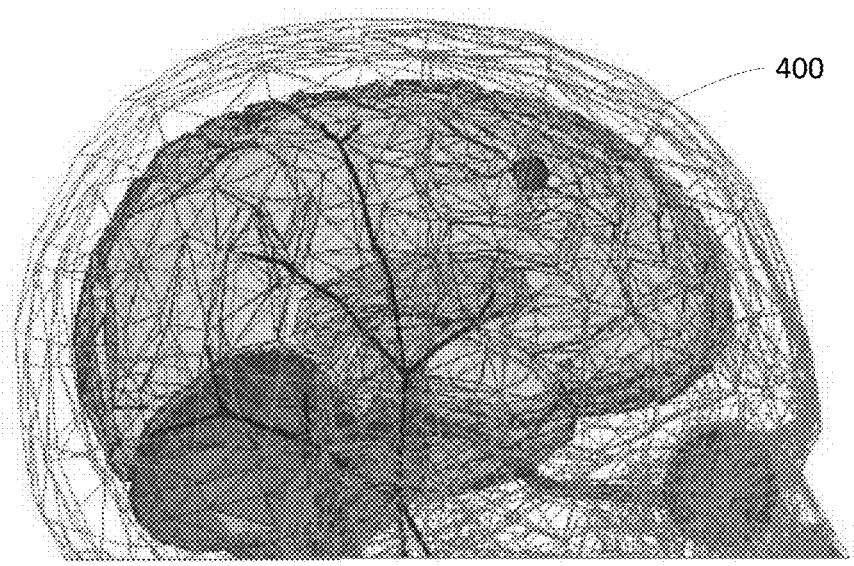
FIG. 17A illustrates a forward model of a 1 cm heated region at a top view of subject's brain and a table of permittivity and conductivity values for several different temperatures.
Figure 17B:
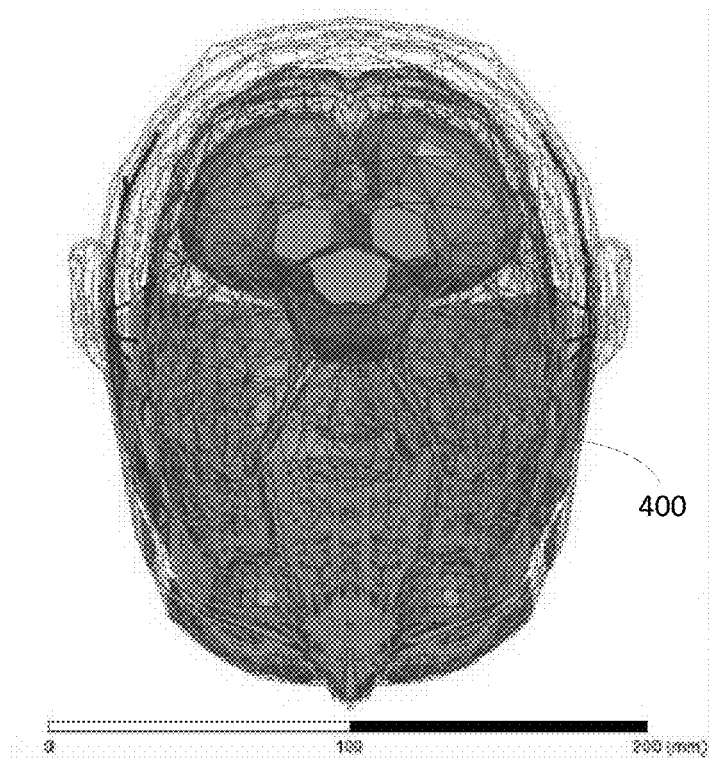
FIG. 17B illustrates a forward model of a 1 cm heated region at a side view of the subject's brain and a table of permittivity and conductivity values for several different temperatures.
Figure 18A:
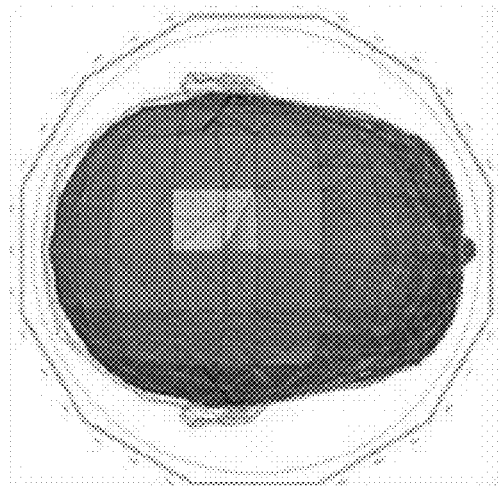
FIGS. 18A-B illustrate sample or baseline electric field levels in an unheated condition for a subject's brain (top view).
Figure 18B:
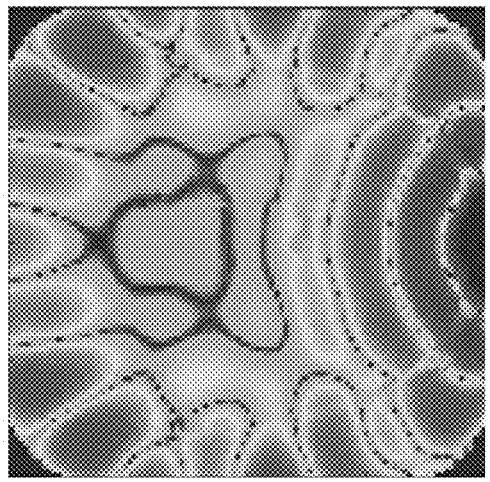
Figure 18C:
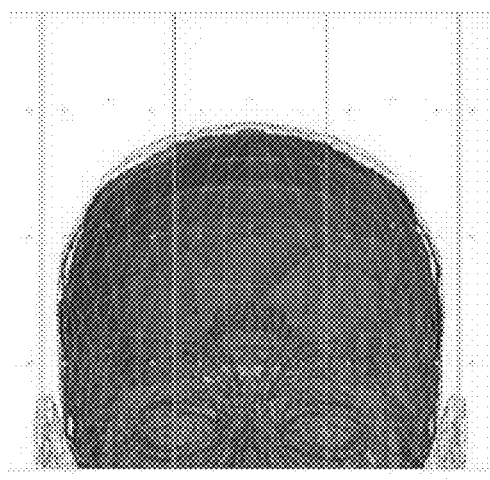
FIGS. 18C-D illustrate sample or baseline electric field levels in an unheated condition for a subject's brain (front view).
Figure 18D:
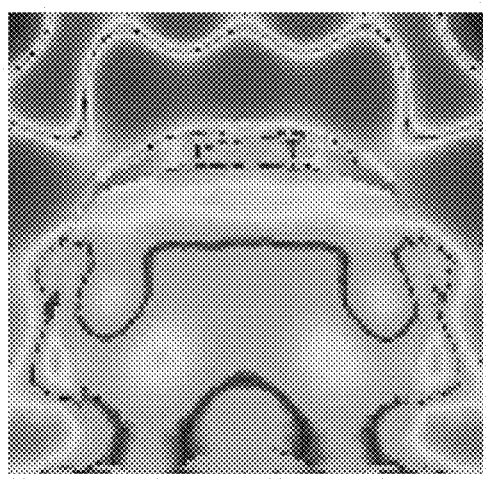
Figure 18E:
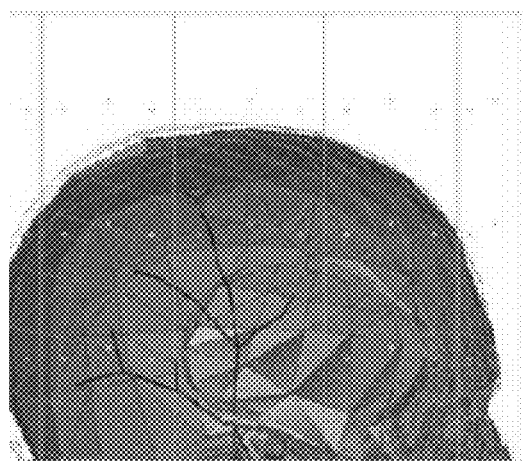
FIGS. 18E-F illustrate sample or baseline electric field levels in an unheated condition for a subject's brain (side view).
Figure 18F:
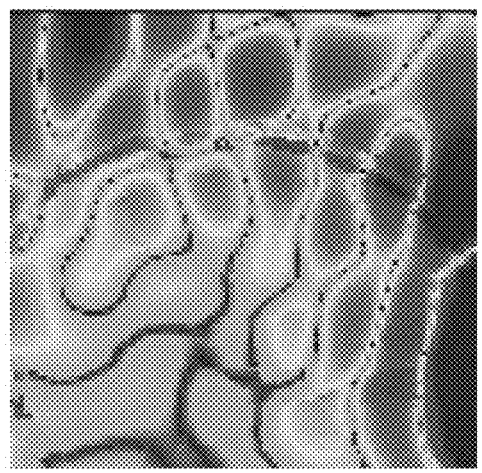

FIGS. 17A-17B illustrate a forward model of a 1 cm heated region in a head. The accompanying table lists permittivity and conductivity values at a variety of temperatures. Creating the thermal image of the treatment region relies upon the temperature dependency of the dielectric properties in the treatment region. With reference to FIGS. 18A-18F, various cross-sections illustrating sample electric fields in an unheated condition are illustrated.

Figure 19A:
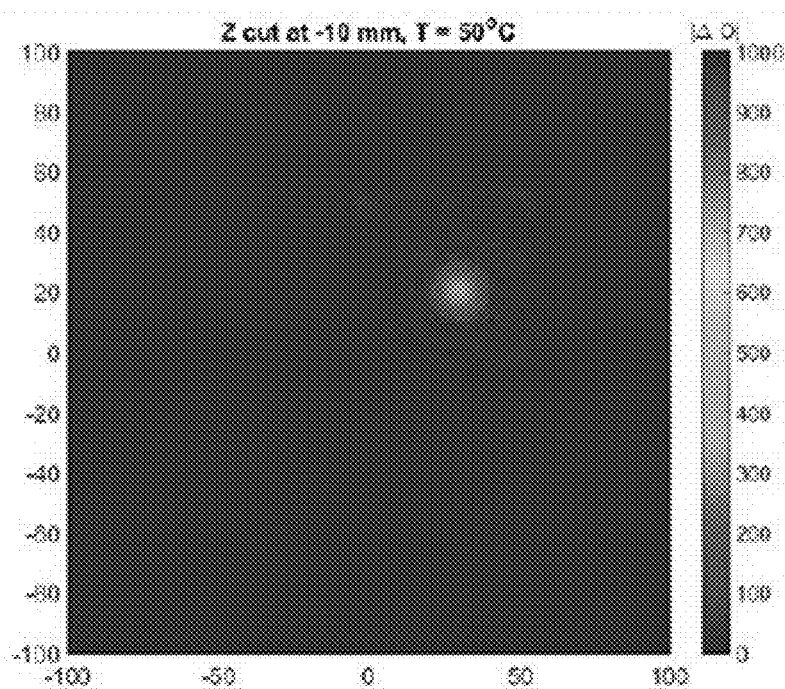
FIG. 19A illustrates an image reconstruction of dielectric scattering and the predicted temperature at a first temperature of 50° C.
Figure 19B:
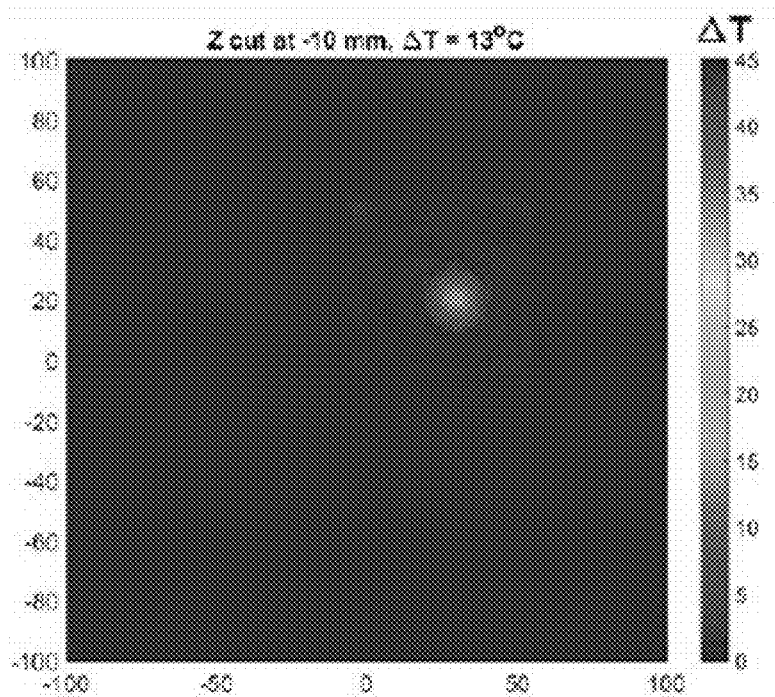
FIG. 19B illustrates an image reconstruction of dielectric scattering and the predicted temperature at a ΔT of 13° C. above body temperature.
Figure 20A:
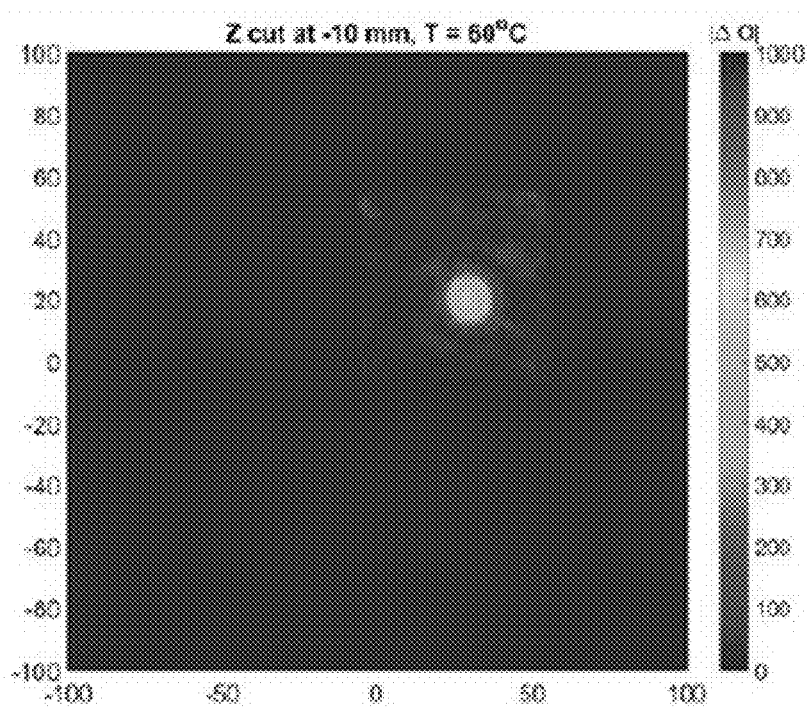
FIG. 20A illustrates an image reconstruction of dielectric scattering and the predicted temperature at a second temperature of 60° C.
Figure 20B:
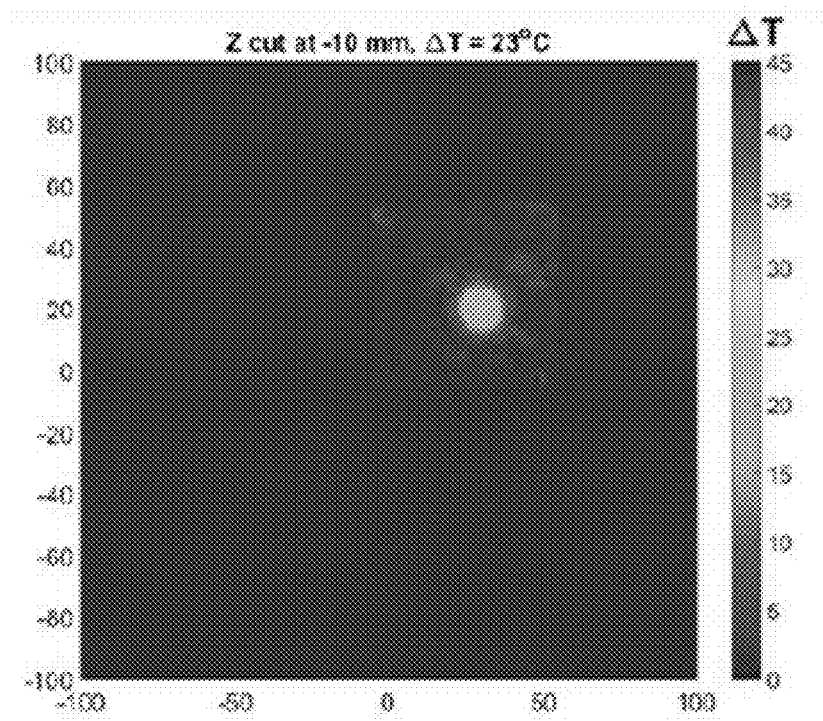
FIG. 20B illustrates an image reconstruction of dielectric scattering and the predicted temperature at a ΔT of 23° C. above body temperature.
Figure 21A:
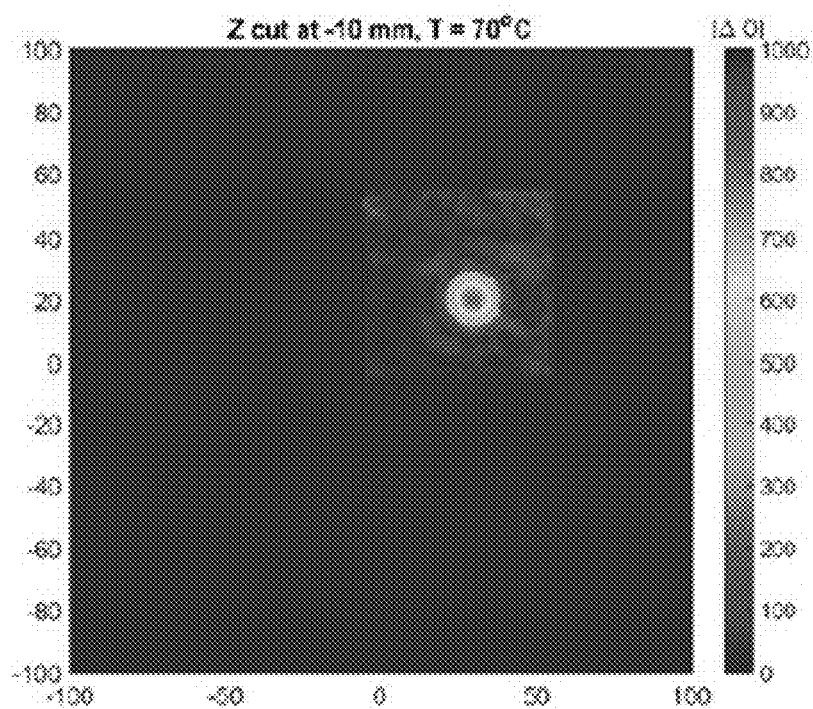
FIG. 21A illustrates an image reconstruction of dielectric scattering and the predicted temperature at a third temperature of 70° C.
Figure 21B:
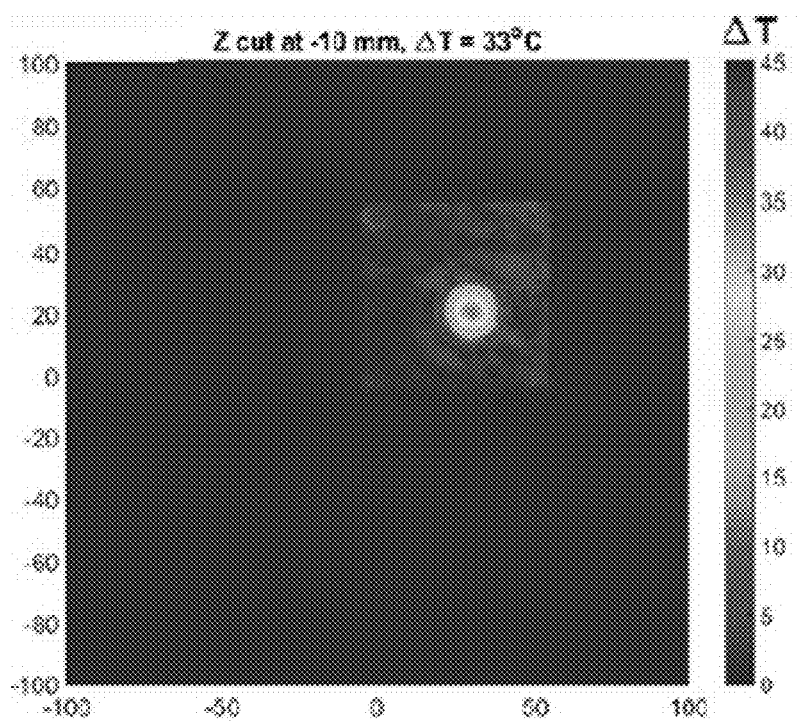
FIG. 21B illustrates an image reconstruction of dielectric scattering and the predicted temperature at a ΔT of 33° C. above body temperature.
Figure 22A:
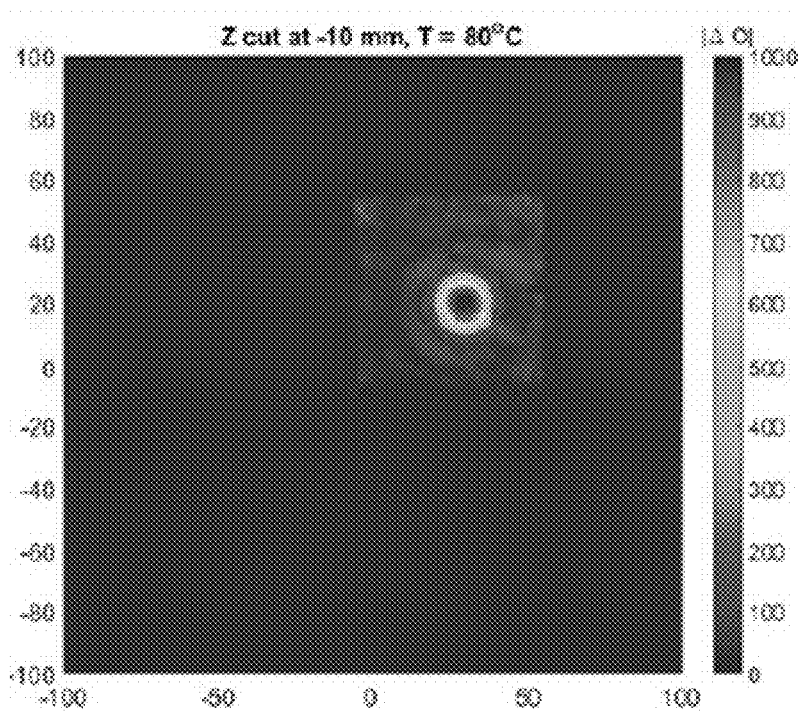
FIG. 22A illustrates an image reconstruction of dielectric scattering and the predicted temperature at a fourth temperature of 80° C.
Figure 22B:
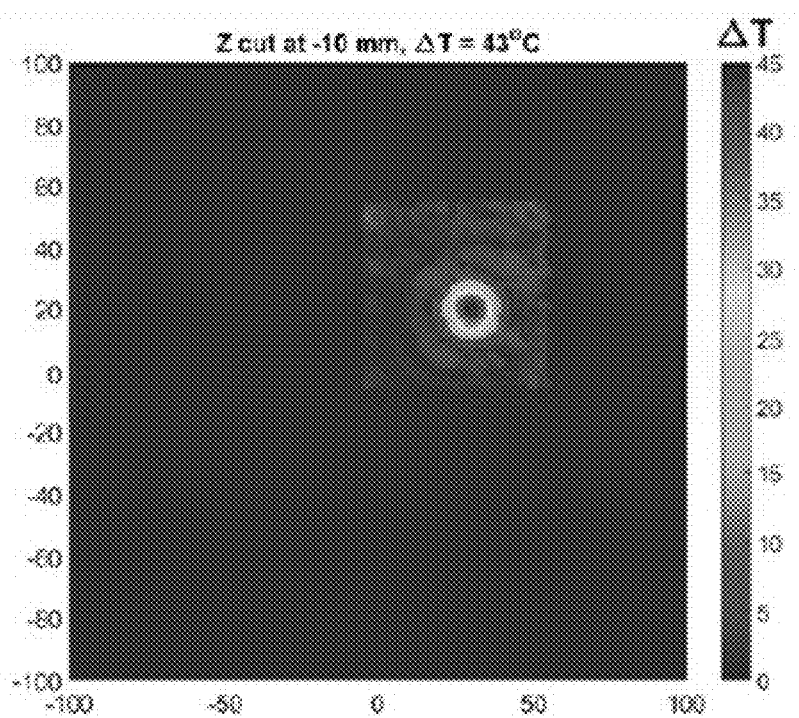
FIG. 22B illustrates an image reconstruction of dielectric scattering and the predicted temperature at a ΔT of 43° C. above body temperature.

With reference to FIGS. 19A-19B, 20A-20B, 21A-21B, and 22A-22B, using a priori knowledge of the electric fields in the unheated head (for example, operating on the assumption that this information is known from prior imaging studies), the thermal images are reconstructed in the region of interest around the treatment location. The temperature mapping is performed using estimated water content and the known relationship between the dielectric properties of water and temperature. The thermal image created using the predicted temperature is compared to the thermal image created using dielectric scattering in each of FIGS. 19A-19B, 20A-20B, 21A-21B, and 22A-22B. FIGS. 19A-19B illustrate the thermal images for T=50° C. and $\Delta T=13$° C., respectively; FIGS. 20A-20B illustrate the thermal images for T=60° C. and $\Delta T=23$° C., respectively; FIGS. 21A-21B illustrate the thermal images for T=70° C. and $\Delta T=33$° C., respectively; and FIGS. 22A-22B illustrate the thermal images for T=80° C. and $\Delta T=43$° C., respectively.

In further embodiments, the microwave system itself may obtain tissue property data directly, either in conjunction with or potentially obviating the need for prior imaging studies. Real-time acquisition methods may be utilized for the purposes of real-time suppression of artifacts.

Conclusion

Accordingly, embodiments described herein relate to a real-time microwave imaging system to image differential temperature based on change in dielectric properties of water with the goal of achieving non-invasive temperature monitoring for thermal therapy systems.

The systems and methods described herein include a cavity-like imaging structure that is fully modeled in HFSS and coupled with a precomputed linear inverse scattering solution. The solution is applied in real-time to a segmented VNA data stream that captures all pairwise scattered field measurements. VNA calibration of T/R antenna pairs is accelerated by using the cavity as an unknown thru standard. The system is tested on water targets with changing temperature. Changes in scattering contrast due to temperature were successfully imaged in cluttered environments, including a simple breast phantom.

This study has produced five findings: (1) the dielectric change of water over the hyperthermia temperature range (for example, 35° C.-60° C.) is easily detectable with the proposed noninvasive setup at 915 MHz; (2) real-time microwave imaging of differential temperature is possible within the constraints of microwave thermal therapy system parameters using a VNA; (3) the spatial resolution of thermal imaging is on the order of the thermal therapy focal spot size in this cavity; (4) 3D images of differential temperature can be formed with 1° C. sensitivity at refresh rates of 4 seconds or better; and (5) the rate of change of scattering contrast magnitude correlates 1:1 with target temperature for a variety of objects.

Section II: Real-Time Microwave Monitoring of Thermal Treatments

In one embodiment, the invention provides a real-time noninvasive thermal monitoring system based on multi-static microwave imaging. The inversion algorithm, control hardware, and measurement hardware were optimized for real-time image formation (refresh rates better than 1 frame per second), and the system was validated with heating tests in simple phantoms.

During the process of developing and experimentally validating the system, improvements in the flexibility and computational efficiency of the forward modeling would be desirable before real-time thermal imaging would be clinically viable. To address these limitations, an in-house wideband forward solver was developed that integrates (a) object modeling (b) waveport excitation, and (c) S-parameter extraction under a conformal finite difference time domain (CFDTD) framework. In particular, this CFDTD solver has enabled the implementation of a fully integrated numerical vector Green's function that addresses the task of linking the object's scattered field to the measured scattered voltage in a more general and flexible way than the waveport vector Green's function method previously used.

Methods

A. Dual Application of Microwave Imaging to Real-Time Thermal Monitoring

Figure 25:
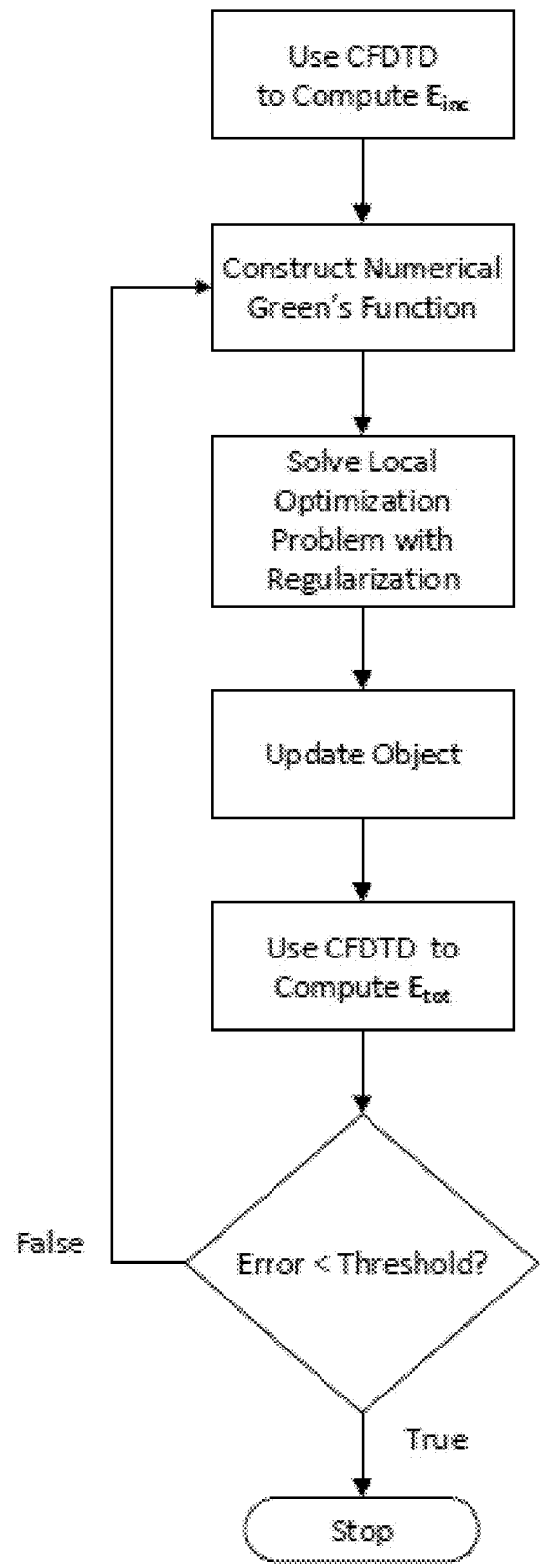
FIG. 25 illustrates an inversion flow chart with CFDTD forward Solver and Integrated numerical Green's function.
Figure 26:
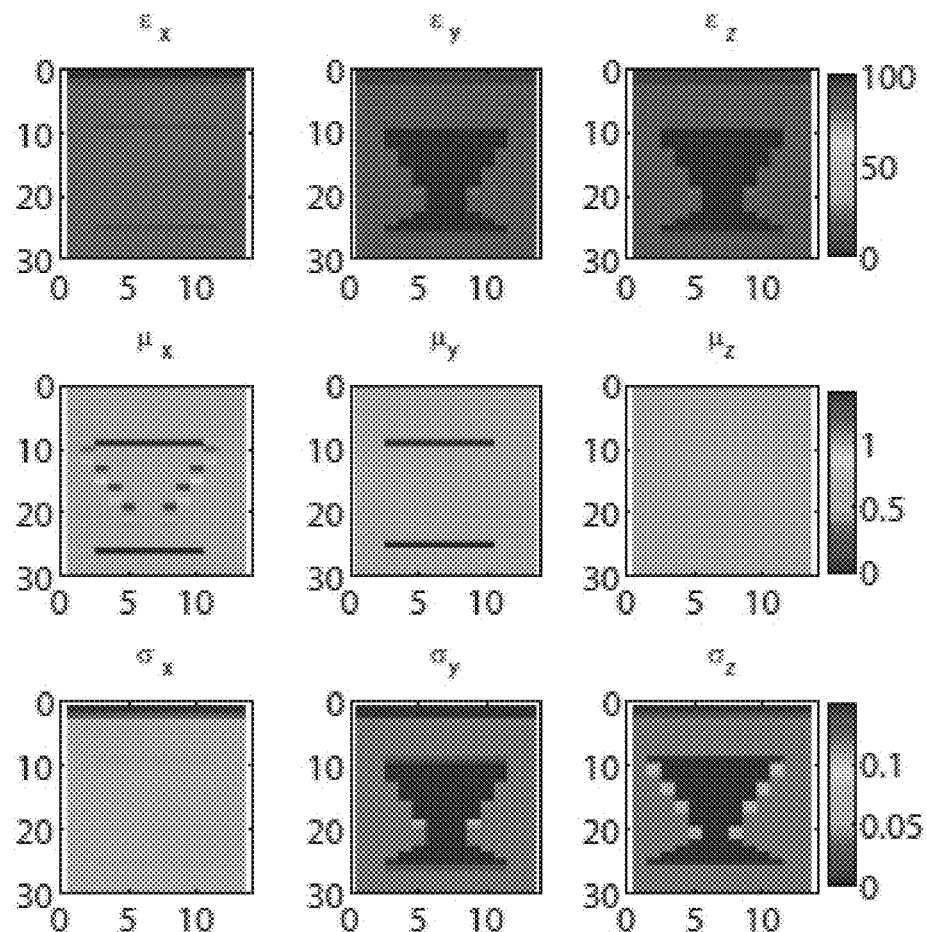
FIG. 26 illustrate effective materials (Row 1: ϵ, Row2: µ, Row3: σ) used to model antennas in imaging cavity with CFDTD.

Real-time microwave monitoring of thermal treatments is based upon two fundamental assumptions: knowledge of the complex dielectric properties of the tissue in the region of interest prior to heating and knowledge of how the dielectric properties of each tissue type will change as a function of temperature. One method of obtaining these dielectric properties is to infer them from an earlier imaging study (such as MRI). However, this has the potential to introduce error both from inaccuracies in mapping one material property (typically water content) to another (complex permittivity) and from uncertainty in coregistering the earlier imaging study with the current patient geometry during the thermal therapy procedure. Instead, it is preferable to generate a map of the dielectric properties directly at the time of the procedure using the same microwave imaging system used for real-time monitoring. It is for this task, along with the task of continuing to update the dielectric map in real-time during the procedure, that the conformal finite-difference time domain (CFDTD) forward solver has been developed and integrated into the inversion algorithm shown in flow chart form in FIG. 25. The iterative inversion algorithm outlined in FIG. 25 uses the following procedure:

1. In the absence of the object, use the conformal FDTD method to calculate the incident field inside the object region for each antenna.

2. Use the incident field due to antenna M and the total field due to antenna N to construct a numerical Greens function linking the unknown object material property to the scattered S-parameter SMN in the presence of the imaging cavity and object. (Note: in the first iteration, the incident field is substituted for the total field in the object region.)

3. Solve for the object material using the local optimization method with regularization and then use this solution to update the material properties in the object region.

4. With the updated object material, use the conformal FDTD method to calculate the total field in the object region and the scattered field in the antenna feed.

5. Compare the difference between the measured and FDTD-calculated scattered fields at the antenna feed. If the difference is smaller than the threshold, stop, and output estimated map of complex permittivity. Otherwise, return to step 2 with the updated total field in the object region.

With the volumetric map of the complex permittivity from the inversion algorithm and the corresponding electric fields from the CFDTD solver in hand, it is then possible to use the Distorted Born Approximation and precompute a linear inverse scattering solution that can be applied in real-time to the multi-static scattered S-parameter measurements that are being continuously acquired by the real-time microwave imaging hardware. This solution, combined with the aforementioned knowledge of how complex permittivity varies with temperature for a given tissue type is what enables real-time thermal monitoring via multi-static array microwave imaging.

B. Conformal FDTD Solver with Waveport Excitation and S-Parameter Extraction

The finite-difference time domain (FDTD) method has proven an increasingly useful tool in the modeling of electromagnetic problems. Along the way, researchers have made a variety of evolutionary improvements designed to address issues of computational efficiency, robustness, and accuracy. Among the most significant of these was the development of the conformal FDTD (CFDTD) method, which utilizes the fact that the E and H fields are not collocated within one cell and creates an effective material that captures the geometry of curvilinear objects without the need for the dense meshing required by the traditional staircase grid.

In order for the CFDTD method to be practically useful in the forward modeling of multi-static antenna array measurements, however, two additional modeling challenges were addressed: (1) how to model the source excitation at the antenna feed, and (2) how to determine the transmit and receive voltages in the feed to extract the S-parameters representing the actual measured signal. Toward that end, a CFDTD forward solver was developed that integrates (1) a conformal 2D finite-difference frequency domain (FDFD) solver to calculate the field distribution and propagation constant of the waveport and a total field scattered field (TFSF) based soft source to feed that solution into the waveport, and (2) an S-parameter extraction method compatible with the conformal framework.

C. Integrated Numerical Vector Green's Function

Numerical Green's functions are used in microwave imaging to account for the effects of the antenna pattern and the presence of the imaging cavity and to link the measured scattered voltage to the object's scattered field during the inversion process. A waveport vector Green's function proved highly effective in accounting for the various non-idealities of real antennas radiating into an imaging cavity, and enabled the development of an experimentally validated imaging system. However, this method relies on inputs from an external forward solver to model the electric fields. Since this requires passing the electric field data from the external solver to the vector Green's implementation in the inversion algorithm, it is inherently cumbersome and computationally inefficient. Furthermore, limitations of the forward solver, the commercial finite element solver, HFSS) also limited the vector Green's function to the background case (Born Iterative type) or to very simple objects (Distorted Born type). To address these limitations, a numerical vector Green's function was introduced that is directly integrated into the conformal FDTD forward solver discussed above.

Derivation of Numerical Vector Green's Function from the Reciprocity Principle: Using reciprocity, we have:

$$\int_V E_{scat}(r) \cdot J_s(r) dv = \int_V E_{inc}(r') \cdot J_{pol}(r') dv' \quad \text{Equation (29)}$$

where r is at the antenna feed, r' is at the object region, $E_{scat}$ is the scattered field produced by the polarization current $J_{pol}$ and $E_{inc}$ is the incident field produced by the test point current source $J_s$. The polarization current produced by the object contrast and the total fields in the object region when transmitted from antenna N can be represented as, $$J_{pol}^N(r') = j\omega\epsilon_0(\epsilon_{obj}(r') - \epsilon_b(r'))E_{obj}^N(r') \quad \text{Equation (30)}$$

If we want to use the scattered field at antenna M in $\hat{p}$ direction, then we should also excite a test point source $J_s^M(r)$ at antenna M in $\hat{p}$ direction.

$$J_s^M(r) = I\hat{p}\delta(r) \quad \text{Equation (31)}$$

Then, the numerical Green's function to link the scattered field at antenna M when transmitting from antenna N and for a given object's dielectric property is:

$$E_{scat}^{\hat{p}}(r) = \frac{j\omega\epsilon_0}{I\delta(r)} \int_{V'} (\epsilon_{obj}(r') - \epsilon_b(r'))E_{obj}^N(r')E_{inc}^M(r') dv' \quad \text{Equation (32)}$$

Figure 24:
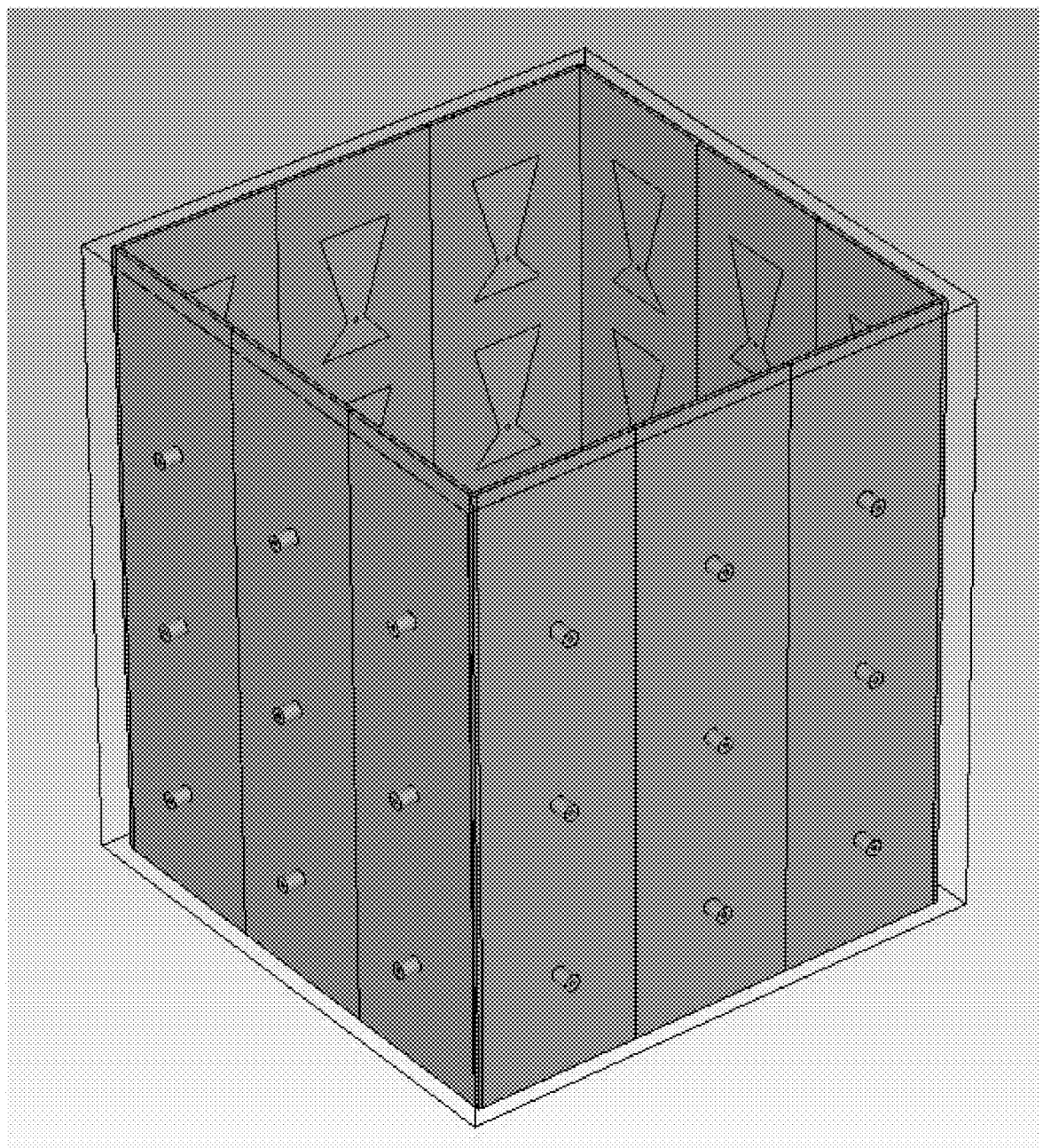
FIG. 24 is a CAD drawing of a prototype imaging cavity.
Figure 27A:
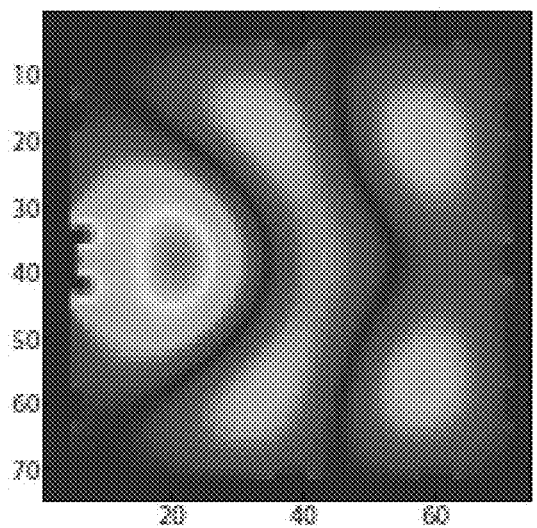
FIG. 27A illustrates |Re(Ez)| due to single transmitting antenna at resonance at a top view of horizontal cut (xy) through cavity.
Figure 27B:
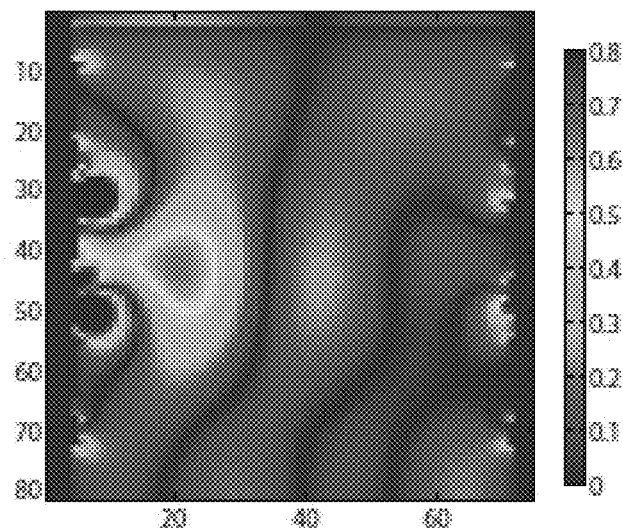
FIG. 27B illustrates |Re(Ez)| due to single transmitting antenna at resonance at a side view of vertical cut (xz) through cavity.

FIGS. 27A-27B illustrate two slices of the magnitude of the vertical component of the electric field inside the imaging cavity (shown in FIG. 24) due to a single transmit antenna at resonance. These fields are in agreement with results obtained previously from both CST Microwave Studio and Ansys HFSS, and are currently being used in tests of the inversion algorithm described above and shown in FIG. 25.

Figure 28A:
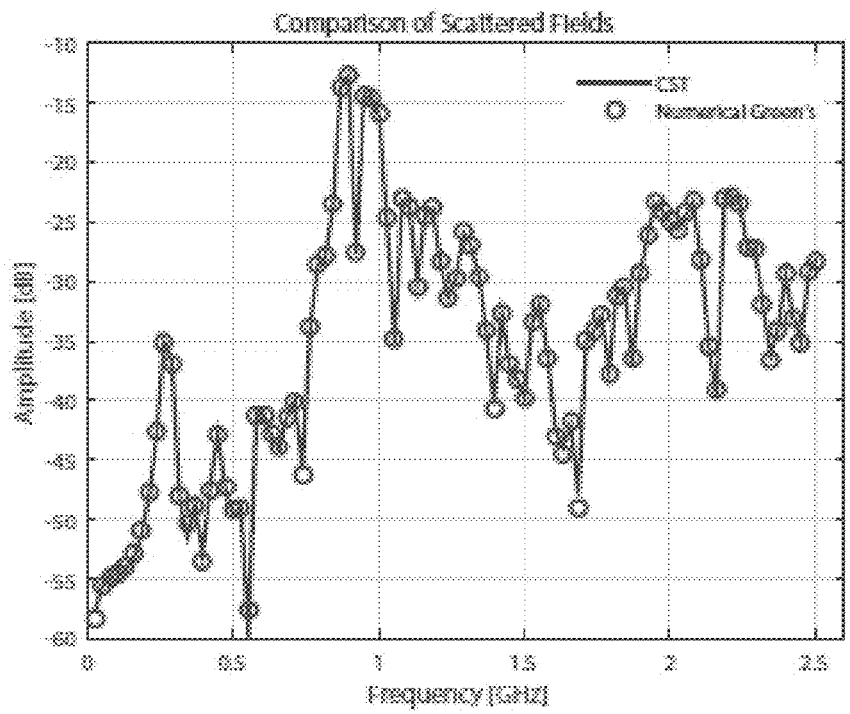
FIGS. 28A and 28B illustrate scattered fields comparison between FDTD solver and numerical Green's function estimation, magnitudes agree within a mean absolute difference of 0.2 dB and phases agree within a mean absolute difference of 2 degrees.
Figure 28B:
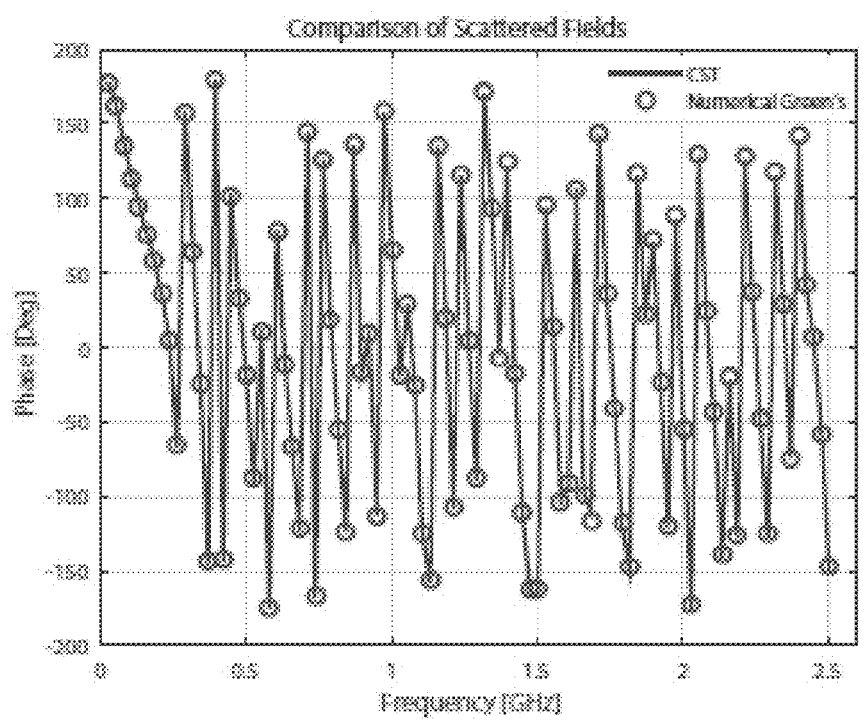

To validate the numerical Green's function, a cubic object with dielectric constant of 16 and size 4×4×4 cm³ was placed in the bottom center of the cubic imaging cavity consisting of four panels. The imaging cavity is filled with a coupling medium with a dielectric constant of 22. The transmitting antenna is located at the middle of one panel and the receiving antenna is at the bottom middle of the adjacent panel. A comparison of the scattered field S-parameters calculated by CST Microwave Studio and those estimated by the numerical Green's function method are shown in FIGS. 28A-28B. As can be seen from FIGS. 28A-28B, the scattered fields estimated by the numerical Green's function agree very well with those calculated by CST.

Section III: Conformal Finite-Difference Time Domain Technique

The finite-difference time domain (FDTD) method originally proposed by Yee has become a widely used tool in the modeling of electromagnetic problems. However, the original FDTD method with staircase mesh has difficulties accurately modeling curved objects. To overcome this problem, Dey et al. proposed a conformal FDTD (CFDTD) algorithm with a modified H field update. This method increased the modeling accuracy at the cost of reduced time-steps. To address this problem, Xiao et al. proposed the enlarged cell technique, while Zagorodnov et al. proposed the uniformly stable conformal (USC) scheme. However, both of these methods are more difficult to implement than the conventional FDTD algorithm and require additional computational steps. To address this, Benkler et al. introduced the effective material and effective electric field concept, which implements the CFDTD within the original form of the conventional FDTD algorithm. Up to this point, however, no detailed development of the CFDTD method with waveport excitation and S-parameter extraction has been found in the current literature.

In light of this, a wideband forward solver was developed that integrates (a) object modeling (b) waveport excitation, and (c) S-parameter extraction under the conformal FDTD framework. In conformal object modeling, the effective material method is presented and utilized to model a coaxial feed and a tapered patch antenna. Compared with the previous work of modeling coaxial feed with thin wire model and conformal technique, a maximally sparse mesh model for the coaxial feed using the effective material was proposed. A complementary calibration scheme is proposed to enhance the impedance modeling accuracy of the coaxial feed. In terms of waveport excitation, this problem was divided into two sub problems, (1) waveport mode calculation, (2) waveport source feeding. For waveport mode calculation, Zhao et al. introduced a compact 2D finite-difference frequency domain (FDFD) method; however, no conformal development of this method compatible with CFDTD has been found in the current literature. Therefore, a conformal 2D FDFD eigenmode solver was developed that solves for the propagation constant and the effective E and H field pattern for waveports with arbitrary shapes. For waveport source feeding, the total field scattered field (TFSF) method was utilized and modified to be compatible with the CFDTD method. For S-parameter extraction, Gwarek et al. proposed the general method to extract wideband S-parameters which can be used for inhomogeneous waveguides and different modes. Thus, a modified S-parameter extraction scheme was introduced that directly uses the effective E field in the calculation and can be fully integrated into the conformal FDTD framework. This implementation of a fully integrated CFDTD solver addresses a wide range of computational electromagnetic problems (including microwave inverse scattering and imaging applications).

Methods

While offering the advantage of simplicity, staircase meshing suffers from the necessity of using a very dense grid in order to accurately model curvilinear objects. To overcome this difficulty, conformal methods utilize the fact that the E and H fields are not collocated within one Yee cell, creating an effective material that captures the geometry of curvilinear objects without the need for dense meshing.

In the CFDTD method, the Faraday's Law equation can be discretized with the non-PEC area of H field and non-PEC length of E field. For example, the discretized updating equation of the Hz field is shown below:

$$H_z\Big|^{n+\frac{1}{2}}_{i,j,k} = H_z\Big|^{n-\frac{1}{2}}_{i,j,k} + \frac{\Delta t}{\mu \cdot \widetilde{S_z}\Big|_{i,j,k}} \cdot \left( E_x\Big|^{n}_{i,j+1,k} \cdot l_x\Big|_{i,j+1,k} - E_x\Big|^{n}_{i,j,k} \cdot l_x\Big|_{i,j,k} - E_y\Big|^{n}_{i+1,j,k} \cdot l_y\Big|_{i+1,j,k} + E_y\Big|^{n}_{i,j,k} \cdot l_y\Big|_{i,j,k} \right)$$

Equation (33)

where $\widetilde{S}$ represents the non-PEC area of the cell face for H field, l is the non-PEC edge length for the E field as shown in FIGS. 29A-29B. The non-PEC area ratio $S^{ratio}$, non-PEC length ratio $l^{ratio}$, effective E field, effective permeability, effective permittivity, and effective conductivity as follows:

$$S_z^{ratio}\Big|_{i,j,k} = \frac{\widetilde{S_z}\Big|_{i,j,k}}{\Delta x_i \Delta y_j}, L_x^{ratio}\Big|_{i,j,k} = \frac{l_x|_{i,j,k}}{\Delta x_i}$$

Equation (34)

$$\widetilde{E} = E \cdot L^{ratio}$$

Equation (35)

$$\widetilde{\mu} = \mu \cdot S^{ratio}, \widetilde{\epsilon} = \frac{\epsilon}{L^{ratio}}, \widetilde{\sigma} = \frac{\sigma}{L^{ratio}}$$

Equation (36)

Then, by replacing the E field and the material with their effective values, the Faraday's Law and Ampere's Law equations become:

$$H_z\Big|^{n+\frac{1}{2}}_{i,j,k} = H_z\Big|^{n-\frac{1}{2}}_{i,j,k} + \frac{\Delta t}{\widetilde{\mu_z}} \left( \frac{\widetilde{E_x}\Big|^{n}_{i,j+1,k} - \widetilde{E_x}\Big|^{n}_{i,j,k}}{\Delta y_j} - \frac{\widetilde{E_y}\Big|^{n}_{i+1,j,k} - \widetilde{E_y}\Big|^{n}_{i,j,k}}{\Delta x_i} \right)$$

Equation (5)

$$\widetilde{E_x}\Big|^{n+1}_{i,j,k} = \frac{2\widetilde{\epsilon_x} - \widetilde{\sigma_x}\Delta t}{2\widetilde{\epsilon_x} + \widetilde{\sigma_x}\Delta t} \cdot \widetilde{E_x}\Big|^{n}_{i,j,k} + \left( \frac{2\Delta t}{2\widetilde{\epsilon_x} + \widetilde{\sigma_x}\Delta t} \right) \cdot \left( \frac{H_z\Big|^{n+\frac{1}{2}}_{i,j,k} - H_z\Big|^{n+\frac{1}{2}}_{i,j-1,k}}{\Delta y_j} - \frac{H_y\Big|^{n+\frac{1}{2}}_{i,j,k} - H_y\Big|^{n+\frac{1}{2}}_{i,j,k-1}}{\Delta z_k} \right)$$

Equation (6)

As seen above, after substituting E, $\mu$, $\epsilon$, and $\sigma$ with their effective values, the original FDTD updating equations remain unchanged, making this method easy to implement. The application of this conformal FDTD method to object modeling and the extension of this method through the development of compatible waveport excitation and S-parameter extraction schemes is discussed.

A. Conformal Object Modeling

In conventional staircase FDTD modeling, only one type of material is allowed within a given Yee cell. This causes difficulty when modeling complex objects with many interfaces, edges, and corners, as the resolution of the objects is therefore limited by the size of the Yee cell. With the conformal FDTD technique, subcell information is utilized to increase the resolution of object modeling. Subcell information is used to create effective material for the modeling of two frequently used objects, a coaxial feed and a patch antenna, and propose an impedance calibration scheme specifically designed to improve coaxial feed modeling.

1) Coaxial feed modeling: The modeling of a Teflon coaxial feed with maximally sparse mesh using effective material is introduced. The coaxial feed extends in the z direction and its xy cross section is shown in FIGS. 30A-30B. Based on the Yee cell shown in FIGS. 29A-29B, we assign the locations of the E and H fields within each cell as shown in FIGS. 30A-30B. After using the non-PEC length ratio and non-PEC area ratio based on the sparse mesh in FIGS. 30A-30B, the effective material value is calculated and shown in FIGS. 31A-31F.

By utilizing subcell information, the coaxial feed can be modeled with only four cells containing non-PEC material. Because so few cells are used, there is a small difference between the simulated and theoretical characteristic impedance. While this can be improved with denser meshing, it comes with a higher computation cost; instead, a straightforward calibration scheme to yield a more accurate impedance was used. The calibration scheme was developed as follows: Define $Z_{th}$ and $Z_{sim}$ as the theoretical and FDTD simulated impedance of the coaxial feed. U and I are the voltage and current in the coaxial feed, while U' and I' are the partial derivative of the voltage and current along the direction of the coaxial cable.

$$Z_{th} = \frac{1}{2\pi}\sqrt{\frac{\mu}{\epsilon}}\ln\frac{D}{d}$$

Equation (39)

$$Z_{sim}(\omega) = \sqrt{\frac{U(\omega)U'(\omega)}{I(\omega)I'(\omega)}}$$

Equation (40)

$$\widetilde{\widetilde{\epsilon}} = \widetilde{\epsilon} \cdot \frac{Z_{sim}}{Z_{th}}, \widetilde{\widetilde{\mu}} = \widetilde{\mu} \cdot \frac{Z_{th}}{Z_{sim}}$$

Equation (41)

Along with the equations for the theoretical impedance (Equation (39)), Equation (40) is also used to extract the impedance of the coaxial feed from FDTD simulation. To calibrate the impedance while retaining the propagation constant, Equation (41) is used to modify the effective material property. As shown below, the accuracy of the calibrated impedance is improved to a value very close to the theoretical impedance.

2) Modeling of Tapered Patch Antenna: An experimental inverse scattering system was developed that uses an imaging cavity with tapered patch antennas. Thus, it is of interest to utilize the conformal method to model these antennas as part of an effort to fully model the entire cavity. In FIGS. 32A-32F, a tapered patch antenna is shown along with its conformal mesh representation. As seen from the figure, when the edge of the patch is not aligned with the Yee grid, the effective material can be used to accurately capture the non-aligned edges. In addition, the size of the Yee cell is no longer limited by the thickness of the metal layer, since both the substrate and the metal material can be accurately modeled with a single Yee cell and the thickness of the patch is easily controlled by the effective material value within the cell. Results and analysis comparing the simulated and measured reflection coefficient of the tapered patch antenna are shown below.

B. Waveport Excitation

In FDTD simulations, one of two types of source excitation is typically used, lumped element or waveport. While the lumped element source is easier to implement, it is difficult to excite a specific mode. For a waveport source, the distribution of the E and H fields of a chosen mode is calculated and then fed into the waveguide. Thus, implementing a waveport source involves two problems, how to accurately calculate the distribution of the E and H fields of a certain mode for an arbitrarily shaped waveguide and how to feed the calculated mode into the waveguide. Furthermore, the following problems are addressed under the conformal FDTD framework.

1) Conformal 2D FDFD solver: The calculation of the cross-sectional field distribution of a waveguide can be formulated as an eigenvalue problem, which can then be solved with the FDFD method. Starting from the method developed by Zhao et al., a non-uniform grid 2D conformal FDFD eigenmode solver is derived that solves the distribution of the effective electric field $\tilde{E}$ and magnetic field $H$ for a specific mode in a conformal modeled waveport. Then, the calculated results from this solver can be directly used in the 3D CFDTD method. Assuming the waveguide is Z-oriented, the E and H field on XY plane propagating in the waveguide can be written:

$$E=[E_x(x,y)\hat{x}+E_y(x,y)\hat{y}+E_z(x,y)\hat{z}]e^{-j\beta z} \quad \text{Equation (42a)}$$

$$H=[H_x(x,y)\hat{x}+H_y(x,y)\hat{y}+H_z(x,y)\hat{z}]e^{-j\beta z} \quad \text{Equation (42b)}$$

where $\beta$ is the propagation constant along the waveguide. Utilizing the conformal method with effective material and effective electric field, the frequency domain Maxwell equations can be written in the forms:

$$\nabla \times \tilde{E} = -jK_0\widetilde{\mu_r}\eta_0 H \quad \text{Equation (43a)}$$

$$\nabla \times H = -jK_0\widetilde{\epsilon_r}\frac{1}{\eta_0}\tilde{E} \quad \text{Equation (43b)}$$

where $K_0$ is the free space wavenumber, $\eta_0$ is the free space wave impedance. By substituting Equation (42) into Equation (43) and taking the difference form of the equations, we can get the expressions of H field in terms of $\tilde{E}$ field, and vice versa. For example, the $H_x$ field can be expressed as:

$$H_x|_{i,j} = \quad \text{Equation (44)}$$

$$\frac{j}{K_0\eta_0\widetilde{\mu_x}|_{i,j} \cdot dy_e|_{j+1}}\left[\widetilde{E_z}|_{i,j+1}-\widetilde{E_z}|_{i,j}\right] - e^{\frac{-j\beta\Delta z}{2}}\frac{\beta}{k_0\eta_0\widetilde{\mu_x}|_{i,j}}\widetilde{E_y}\bigg|_{i,j}$$

Similarly, the expressions of $H_y$, $H_z$, $\tilde{E}_x$, $\tilde{E}_y$, $\tilde{E}_z$ are acquired. Approaching $\Delta z$ to be 0, reducing the 3D Yee mesh to 2D grid, and eliminating the $\tilde{E}_z$ and $H_z$ from the derived six equations, the final formulation of the conformal 2D FDFD solver is as follows:

$$\beta K_0 H_x|_{i,j} = \alpha_1^{hx}\left(\widetilde{E_x}|_{i-1,j}-\widetilde{E_x}|_{i-1,j+1}\right) - \quad \text{Equation (45)}$$

$$\alpha_2^{hx}\left(\widetilde{E_x}|_{i,j}-\widetilde{E_x}|_{i,j+1}\right) - \alpha_3^{hx}\widetilde{E_y}|_{i-1,j}+\alpha_4^{hx}\widetilde{E_y}|_{i,j}-\alpha_5^{hx}\widetilde{E_y}|_{i+1,j}$$

-continued $$\beta K_0 H_y|_{i,j} = \alpha_1^{hy}\widetilde{E_x}|_{i,j-1} + \alpha_2^{hy}\widetilde{E_x}|_{i,j}+\alpha_3^{hy}\widetilde{E_x}|_{i,j+1} - \quad \text{Equation (46)}$$

$$\alpha_4^{hy}\left(\widetilde{E_y}|_{i,j}-\widetilde{E_y}|_{i+1,j-1}\right) - \alpha_5^{hy}\left(\widetilde{E_y}|_{i,j}-\widetilde{E_y}|_{i+1,j}\right)$$

$$\beta K_0\widetilde{E_x}|_{i,j} = \alpha_1^{ex}\left(H_x|_{i,j}-H_x|_{i,j-1}\right) + \quad \text{Equation (47)}$$

$$\alpha_2^{ex}\left(H_x|_{i+1,j-1}-H_x|_{i+1,j}\right) + \alpha_3^{ex}H_y|_{i-1,j}+\alpha_4^{ex}H_y|_{i,j}+\alpha_5^{ex}H_y|_{i+1,j}$$

$$\beta K_0\widetilde{E_y}|_{i,j} = -\alpha_1^{ey}H_x|_{i,j-1} + \alpha_2^{ey}H_x|_{i,j} \quad \text{Equation (48)}$$

$$-\alpha_3^{ey}H_x|_{i,j+1} + \alpha_4^{ey}\left(H_y|_{i-1,j}-H_y|_{i,j}\right) - \alpha_5^{ey}\left(H_y|_{i-1,j+1}-H_y|_{i,j+1}\right)$$

where, in the coefficients $\alpha$, $dx_{e|i}$ is the distance between the $(i)^{th}$ and the $(i+1)^{th}$ electric field mesh grid in x direction, $dy_{h|j}$ is the distance between the $(j-1)^{th}$ and $(j)^{th}$ magnetic field mesh grid in y direction. The expressions of $\alpha^{hx}$ are shown below (sample coefficients of the 2D FDFD solver).

$$\alpha_1^{hx} = \frac{1}{\eta_0\widetilde{\mu_z}|_{i-1,j} \cdot dx_h|_i \cdot dy_e|_{j+1}} \quad \text{Equation (49a)}$$

$$\alpha_2^{hx} = \frac{1}{\eta_0\widetilde{\mu_z}|_{i,j} \cdot dx_h|_i \cdot dy_e|_{j+1}} \quad \text{Equation (49b)}$$

$$\alpha_3^{hx} = \frac{1}{\eta_0\widetilde{\mu_z}|_{i-1,j} \cdot dx_e|_i \cdot dx_h|_i} \quad \text{Equation (49c)}$$

$$\alpha_4^{hx} = \frac{-K_0^2 \cdot \widetilde{\epsilon_y}|_{i,j}}{\eta_0} + \quad \text{Equation (49d)}$$

$$\frac{1}{\eta_0\widetilde{\mu_z}|_{i,j} \cdot dx_e|_{i+1} \cdot dx_h|_i} + \frac{1}{\eta_0\widetilde{\mu_z}|_{i-1,j} \cdot dx_e|_i \cdot dx_h|_i}$$

$$\alpha_5^{hx} = \frac{1}{\eta_0\widetilde{\mu_z}|_{i,j} \cdot dx_e|_{i+1} \cdot dx_h|_i} \quad \text{Equation (49e)}$$

Other coefficients are similar. The four equations above are used to formulate an eigenvalue problem, where the $\tilde{E}$ and H fields are the eigenvectors and $\beta K_0$ is the eigenvalue. The problem is reformulated as the generalized eigenvalue problem below:

$$[A]\cdot\{x\}=\lambda[B]\cdot\{x\} \quad \text{Equation (50)}$$

where B is a unit matrix. The zero field within the PEC region is realized in two ways. For $\tilde{E}_z$ and $H_z$ field within the PEC region, a large number is assigned to $\tilde{\epsilon}_z$ and $\tilde{\mu}_z$ to ensure the corresponding field term in the equation becomes zero. To set the $\tilde{E}_x$, $\tilde{E}_y$, $H_x$, $H_y$ within the PEC region to 0, the corresponding diagonal terms of matrix A and B are multiplied by a very large number. Usually, $10^{15}$ is sufficient. Then, the ith equation will become $10^{15}\cdot(a_{ii}-\lambda b_{ii})x_i=0$, which ensures $x_i=0$. Each solved eigenvector represents the distribution of the $\tilde{E}$ and H field of certain mode within a waveport. The total power of a specific mode within the waveport can be calculated by integrating the mode field E and H over the non-PEC area $\tilde{S}$ of the waveport. However, as shown in Equation (51), through simple transformation, it is equivalent to directly integrating the $\tilde{E}$ and H over the total area S of the waveport, which is the surface area of related Yee cells.

$$P=\frac{1}{2}\iint(E\times H^*)\cdot d\tilde{S}=\frac{1}{2}\iint(\tilde{E}\times H^*)\cdot ds \quad \text{Equation (51)}$$

2) Source Feeding: To accurately feed the mode fields into the waveport, we use a modified TFSF soft-source excitation method that can be directly used in the CFDTD algorithm and can accurately excite the desired fields with no retro-reflection and without being affected by the Courant condition number. The original TFSF method was proposed to excite plane waves and to divide the computation domain into a total field region and a scattered field region. To apply the TFSF method to waveport excitation, the electric source field is fed into the waveport during the magnetic field updating loop and vice versa. For example, the effective electric field source $\tilde{E}^s$ is fed into the waveport through:

$$H_x^{n+\frac{1}{2}} = H_x^{n-\frac{1}{2}} - \left(\frac{\Delta t}{\overline{\mu_y}}\right)\left([\nabla \times \tilde{E}]_x^n - \frac{\tilde{E}_y^s \cdot f(t)}{\Delta z}\right) \quad \text{Equation (52a)}$$

$$H_y^{n+\frac{1}{2}} = H_y^{n-\frac{1}{2}} - \left(\frac{\Delta t}{\overline{\mu_y}}\right)\left([\nabla \times \tilde{E}]_y^n + \frac{\tilde{E}_x^s \cdot f(t)}{\Delta z}\right) \quad \text{Equation (52b)}$$

where $\Delta z$ is the Yee cell length in z direction at the source point, $\tilde{E}_x^s$, $\tilde{E}_y^s$ are the source field coefficients calculated by the conformal 2D FDFD solver and f(t) is the time domain function of the signal. Here, the effective material and effective E field are used to make this formulation compatible with the conformal FDTD technique. The magnetic field source $H^s$ can also be fed into the waveport using similar schemes. Feeding either $\tilde{E}^s$ or $H^s$ will excite a bi-directional propagating wave, which can be used to accurately extract S-parameters of various waveport modes with the method described below. In the TEM mode case, one can excite a unidirectional propagating wave by feeding both $\tilde{E}^s$ and $H^s$ simultaneously into the waveport with the TFSF method.

C. S-parameter Extraction

Figure 33:
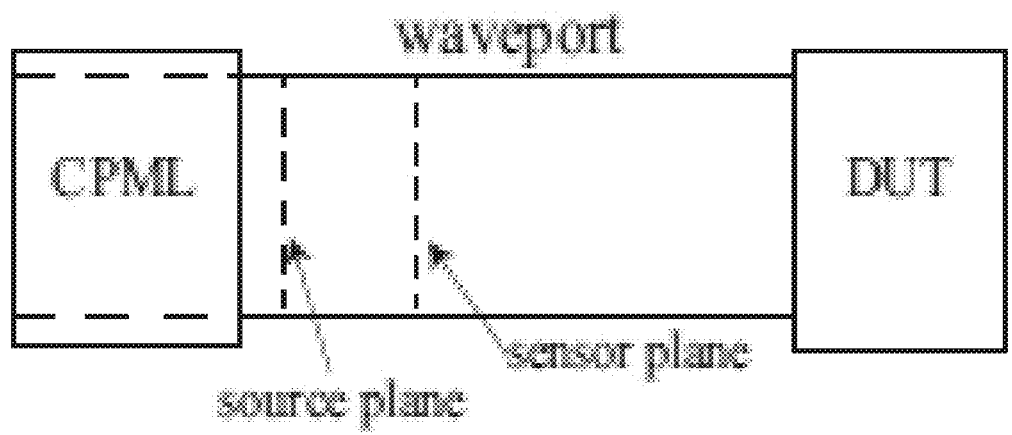
FIG. 33 illustrates a waveport for S-parameter extraction.

For S-parameter extraction, the method starts with Gwarek et al. and is modified to be compatible with the conformal technique. As shown in FIG. 33, the waveport with the complex frequency-shifted perfect matched layer (CPML) absorbing boundary condition is terminated. Either the incident $\tilde{E}$ or the H source is fed on the source plane which excites a bi-directional propagating wave. The total $\tilde{E}$ and H field are recorded in the sensor plane. The sensor plane is placed between the source plane and the device under test (DUT). To extract the S-parameters from waveport, the voltage and current of a particular mode within the waveport need to be defined. The definition of waveport voltage and current from Gwarek et al. is used, and with the same simple transformation as Equation (51), they are modifed to be compatible with the CFDTD method as follows:

$$U(t) = \iint_S \tilde{E}(i,j,k,t) \times h(i,j,\omega) \cdot dS \quad \text{Equation (53a)}$$

$$I(t) = \iint_S \tilde{e}(i,j,\omega) \times H(i,j,k,t) \cdot dS \quad \text{Equation (53b)}$$

where $\tilde{e}$ and $h$ are normalized mode fields calculated by the 2D conformal FDFD solver, and $\tilde{E}$ and H are the fields computed by the CFDTD at the sensor plane. S is the total area of the waveport including the PEC area. In this way, the $\tilde{e}$ and $\tilde{E}$ field from the conformal solvers can be directly used. Meanwhile, in contrast to integrating over the non-PEC area, integrating over the total area S allows us to directly use the surface area of related Yee cell which is readily available. From Gwarek et al., the incident wave $a(\omega)$ and reflected wave $b(\omega)$ are defined as:

$$a(\omega) = \frac{U(\omega) + Z(\omega)I(\omega)}{2\sqrt{Z(\omega)}} \quad \text{Equation (54a)}$$

$$b(\omega) = \frac{U(\omega) - Z(\omega)I(\omega)}{2\sqrt{Z(\omega)}} \quad \text{Equation (54b)}$$

where $Z(\omega)$ is the impedance of the waveport calculated with Equation (40). S-parameter of the device under test can then be extracted when dividing b(w) by the corresponding $a(\omega)$.

Results

In this section, the conformal object modeling is validated, the modified TFSF feeding method, and the simple coaxial calibration scheme with a Teflon coaxial cable. Then, the conformal 2D FDFD solver with a rectangular waveguide and a coaxial feed is validated. Finally, the conformal modeling, waveport excitation and S-parameter extraction with a tapered patch antenna and a waveguide with two coaxial probes are collectively validated.

A. Coaxial feed modeling validation

Figure 34A:
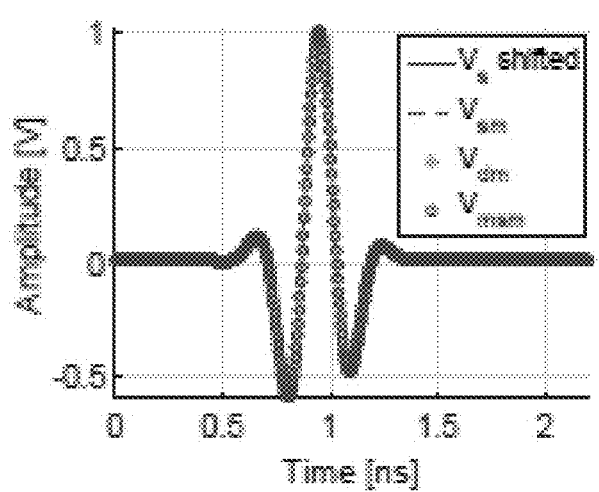
FIGS. 34A and 34B illustrate wave propagation and modeled impedance of coaxial cable.
Figure 34B:
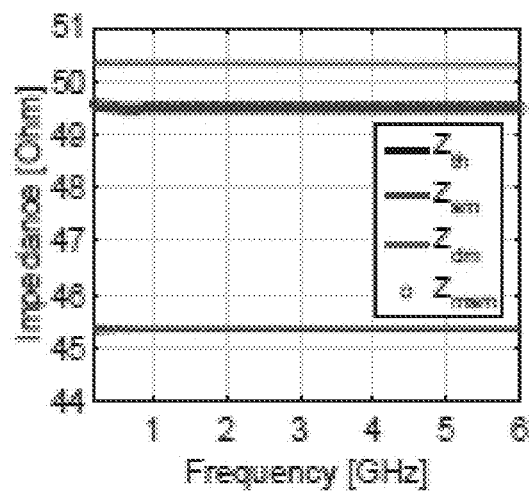

In this example, the conformal FDTD modeling and simulation results of a Teflon filled coaxial feed using effective material with (1) a sparse mesh, (2) a dense mesh and (3) a modified sparse mesh with calibration is demonstrated. The coaxial feed has the same dimension as in FIGS. 30A-30B. A modulated Gaussian pulse with a bandwidth of 200 MHz to 6 GHz is fed into the coaxial cable with the modified TFSF method. The timestep used in the simulation is 2 ps, and the voltage waveform in time is recorded at both the source plane and the observation plane 8 cm away. In all three meshing cases, simulation results indicated a shift of 192 timesteps (0.384 ns) between the source signal and the signal in the observation plane. Thus, the wave propagation speed in the simulated cable is $2.08 \times 10^8$ m/s—very close to the theoretical speed of $2.07 \times 10^8$ m/s. Also, FIGS. 34A-34B shows that the observed voltage waveform is well preserved for all three cases. Finally, the impedance of the cable is calculated with Equation (40). As shown in FIGS. 34A-34B, with increased mesh density, the simulated impedance approaches the theoretical value. However, with calibration, the modified sparse mesh yields the most accurate impedance.

B. Conformal 2D FDFD Mode Solver Validation

In this section, the 2D conformal FDFD mode solver will be evaluated with the calculation of the mode and field distribution of a rectangular waveguide and a Teflon filled coaxial feed.

1) Rectangular waveguide: The dimensions of the air-filled rectangular waveguide are $19.05 \times 9.525$ mm$^2$. As shown in FIG. 35, the calculated propagation constant (first five modes shown) are in good agreement with their theoretical value.

2) Coaxial feed: The 2D conformal FDFD solver can also be used to solve for the coaxial feed in FIGS. 30A-30B with curved edges. The calculated propagation constant matches very well with the theoretical value across the band. The field distribution of the TEM mode shown in FIGS. 36A-36D also matches very well with theory. Thus, we have validated that this conformal FDFD solver is very accurate when solving waveports with curvilinear edges.

C. End-to-End Validation with Patch Antenna Reflection Coefficient Modeling

In this example, we model the reflection coefficient of a probe fed, tapered patch antenna (FIGS. 32A-32F), developed for medical applications. This was selected as a practical example that collectively tests each of the methods developed herein: conformal object modeling (sparse mesh coax feed modeling with impedance calibration), waveport excitation, and S-parameter extraction. A comparison with experimental results in FIGS. 37A-37B show good agreement in both the magnitude and phase of $S_{11}$, and serves as an end-to-end validation of all of the conformal methods developed above working in concert.

D. End-to-End Validation with Transmission Coefficient Modeling in a Waveguide

Lastly, the modeling of the transmission Sparameter between two arbitrarily placed coaxial probes in a WR-187 waveguide (as shown in FIGS. 38A-38B) is validated. The waveguide is hollow brass with outer dimensions of 2.54× 5.08×15.2 $cm^3$ and open on either end. One probe is located 1.91 cm inward from one corner along both axes and the other is located 2.54 cm and 1.27 cm from the other corner. A dense mesh is used to model the coaxial probes, and the TEM field distribution from FIGS. 36A-36D is used to excite the coaxial feed. The forward transmission S-parameters extracted from the simulation and measured with the network analyzer presented below indicate good agreement (as shown in FIGS. 39A-39B) and serve as final validation of the methods developed herein.

Conclusion

Integrated object modeling, waveport excitation, and S-parameter extraction under the conformal FDTD framework was investigated. First, conformal modeling with effective material method is discussed, and then is utilized to model the coaxial feed with a minimum number of Yee cells. A complementary calibration scheme is proposed to increase the impedance modeling accuracy of the coaxial feed, while keeping the propagation constant unchanged. Second, a conformal 2D FDFD solver is developed which is capable of accurately computing the propagation constant and mode field distribution of a waveport with curved edges. In addition, the solver directly computes the $\tilde{E}$ field which can then be naturally fed into the CFDTD algorithm. A modified TFSF soft source excitation method compatible with the CFDTD algorithm is also developed, and its accuracy is validated by comparing the source signal and excited signal within a coax feed. Third, a modified S-parameter extraction scheme is introduced which directly utilizes the $\tilde{E}$ field. This modified method allows integrating over the total area of the waveport when computing mode voltage and current without the need to distinguish between PEC areas and non-PEC areas. Last, all of the methods above are fully integrated into a complete forward solver and validated by several simulations and experiments.

Section IV: Numerical Vector Green'S Function for S-Parameter Measurement with Waveport Excitation In solving microwave inverse scattering problems, the unknown object material property is often related to the scattered electric field through the volume integral equation (VIE). In the case of a homogeneous background, the kernel of the VIE is a dyadic Green's function, that can be obtained analytically. However, in inverse scattering experiment, antennas or probes are always present in the background, making the background inhomogeneous. In this case, there is no analytical form of the Green's function, and the kernel of the VIE can only be obtained numerically with reciprocity principle. Moreover, the measurement of choice in microwave inverse scattering experiment is always a set of scattered S-parameter with the vector network analyzer (VNA). The S-parameter, defined as the voltage ratio, is a scalar instead of a vector. Thus, a new vector Green's function kernel within the VIE is needed which relates the total field within the object domain to the scattered S-parameter (scalar) instead of scattered field (vector). In addition, to calculate the vector Green's function numerically, we need to excite antenna feeds. Instead of using a dipole or lumped element source, a more accurate waveport source, which could excite the desired modes of the feed, is used here. A numerically calculated vector Green's function under waveport excitation is described that serves as a new kernel in the VIE to link the object material property to the measured scattered S-parameter.

Previously, for inverse scattering with a homogeneous background, an analytical dyadic Green's function is used as the kernel of the VIE. With an inhomogeneous background, dipole source, plane wave source, or antenna gain patterns are used to in the inverse scattering experiment, which is not sufficiently accurate to model the antennas and link the fields at the antenna feed to the voltage. Hagness et al. uses a resistive voltage source which could not account for the different modes in the antenna feed. Yuan et al. uses a waveport source to formulate the Green's function, however, the output is in the form of scattered voltage and it did not account for the case that transmitting and receiving waveports have different characteristics and impedance. A source scattering matrix approach is used to model the antenna, formulate the Green's function and links the object property to the S-parameter. However, this approach is not fully numerical which have difficulties accounting for the inhomogeneous background other than the antennas. The full numerical vector Green's function could directly links the object property to the S-parameter in an inhomogeneous background with waveport excitation, where transmitting and receiving waveports could have different characteristics, impedance and modes.

The general form of the new vector Green's function for S-parameter measurement with waveport source is derived. To compute the vector Green's function, the incident field and total field within the object domain are obtained numerically with the FDTD method under waveport excitation. Note, this general form of the new vector Green's function is not tied with the FDTD method, other numerical methods (e.g. FEM, FDFD) can also be used. The rest of the paper is organized as follows: In section II, the detailed derivation of the new vector Green's function is given and the validation steps are presented. Below, three examples are given to validate the vector Green's function. The first example validates the vector Green's function in simulation, when the transmitting and receiving waveports have different geometry and characteristic impedance. The second and third example validate the vector Green's function with measurements, where the coaxial feed waveport is used. The third example using the imaging cavity serves as a precursor for our inverse scattering experiment with this vector Green's kernel in the VIE.

Derivation

In this section, the volume integral equation is introduced to formulate the inverse scattering problem. Then, the Green's function to link the object property to the scattered field for homogeneous background and inhomogeneous background is presented. Next, the waveport source and S-parameter extraction will be introduced under the FDTD framework, and numerical vector Green's function for S-parameter measurement with waveport excitation is demonstrated and derived. Last, the validation steps for the new numerical vector Green's function are presented.

A. Volume Integral Equation

In inverse scattering problems, the volume integral equation is often used to relate the unknown objects' dielectric property to the measured scattered fields.

$$E(r) = E_{inc}(r) + k_b^2 \int \int \int \overline{G}(r, r') \cdot \left(\Delta\epsilon(r') + \frac{\Delta\sigma(r')}{j\omega\epsilon_b}\right) E(r') dV' \quad \text{Equation (55)}$$

where r is the observation position vector, r' is the object domain position vector. E is the total field and $E_{inc}$ is the incident field. $k_b$ is the lossless background wavenumber with $k_b^2 = \omega^2\mu_0\epsilon_b$. $\epsilon_b$ is the background permittivity with $\epsilon_b = \epsilon_0\epsilon_{rb}$, where $\epsilon_{rb}$ is the background relative permittivity. The object's material contrast function is defined as $$\Delta\epsilon(r) = \frac{\epsilon(r) - \epsilon_b}{\epsilon_b} \quad \text{Equation (56a)}$$

$$\Delta\sigma(r) = \sigma(r) - \sigma_b \quad \text{Equation (56b)}$$

where $\epsilon(r)$ and $\sigma(r)$ are the permittivity and conductivity of the object. $\Delta\epsilon(r)$ is the normalized permittivity contrast function which is unitless. $\Delta\sigma(r)$ is the conductivity contrast function which has the unit of Siemens per meter. $\overline{G}(r, r')$ is the dyadic Green's function. In a homogeneous background medium, the dyadic Green's function can be computed analytically as $$\overline{G}(r, r') = \left[\overline{I} + \frac{\nabla'\nabla'}{k^2}\right] g(r, r') \quad \text{Equation (57)}$$

where $$g(r, r') = \frac{e^{-jk|r-r'|}}{4\pi|r-r'|} \quad \text{Equation (58)}$$

with k as the background wavenumber given by $$k^2 = k_b^2 \left(1 + \frac{\sigma_b}{j\omega\epsilon_b}\right) \quad \text{Equation (59)}$$

The scattered field can be written as the difference between the total field and the incident field $$E_{scat}(r) = E(r) - E_{inc}(r) \quad \text{Equation (60)}$$

and if the object function O(r') is defined as $$O(r') = \Delta\epsilon(r') + \frac{\Delta\sigma(r')}{j\omega\epsilon_b} \quad \text{Equation (61)}$$

the volume integral equation then becomes $$E_{scat}(r) = k_b^2 \int\int\int O(r')\overline{G}(r,r') \cdot E(r') dV' \quad \text{Equation (62)}$$

B. Green's Function for Inhomogeneous Background with Dipole Source

When the background medium is inhomogeneous, there is often no analytical form of the Green's function. This is often the case in microwave imaging experiments with the presence of antennas and the imaging cavity in the background. When illuminating an object at location r', the total electric field within the object region produces a polarization current which can be written as $$J_{pol}(r') = j\omega\epsilon_b \left(\Delta\epsilon(r') + \frac{\Delta\sigma(r')}{j\omega\epsilon_b}\right) E(r') \quad \text{Equation (63)}$$

Using reciprocity, if the scattered field produced by the polarization current at the receiver's location r is defined as $E_{scat}(r)$, remove the object from the scenario and excite a current source $J_s$ at the receiver's location r, and record the incident field $E_{inc}(r')$ within the objects' region r', the result is $$\int\int\int E_{scat}(r) \cdot J_s(r) dV = \int\int\int E_{inc}(r') \cdot J_{pol}(r') dV \quad \text{Equation (64)}$$

If $J_s$ is a dipole source pointing at $\hat{p}$ direction $$J_s(r) = Idl\delta(r - r_p)\hat{p} \quad \text{Equation (65)}$$

then the scattered field can be written as $$E_{scat}(r) \cdot \hat{p} = \frac{\int\int\int E_{inc}(r') \cdot J_{pol}(r') dV'}{Idl} = k_b^2 \int\int\int \frac{O(r')E_{inc}(r') \cdot E(r') dV'}{-j\omega\mu_0 Idl} \quad \text{Equation (66)}$$

Thus, the vector numerical Green's function for the inhomogeneous background with a dipole source is $$G(r, r') = \frac{E_{inc}(r')}{-j\omega\mu_0 Idl} \quad \text{Equation (67)}$$

This function is termed a numerical vector Green's function, because: (1) $E_{inc}$ is computed numerically, and (2) the Green's function is no longer a dyad but a vector. The Green's function here can be computed with various numerical electromagnetic methods (for example, FEM, FDFD, and FDTD). Below, the FDTD method is utilized; however, the formulation of the numerical vector Green's function for S-parameter measurement with waveport excitation is not specific to any numerical methods.

C. Waveport Excitation and S-parameter Extraction

In the simulation of realistic microwave systems, the waveport source is often used to excite the feed rather than a simple dipole source, as waveport source could accurately excite various waveguides with the desired modes. To implement the waveport source with FDTD method, calculate first the field distribution of E and H field of the desired mode with the 2D FDFD solver on the waveport surface. The solved field mode template for electric and magnetic field are $e^t(r)$ and $h^t(r)$, which are then normalized to produce unit power.

$$\frac{1}{2}\int\int_A e^t(r) \times h^t(r) \cdot dA = 1 \quad \text{Equation (68)}$$

where A is the non-PEC surface area of the waveport. If the source signal waveform is f(t), the waveport is excited in FDTD simulation with the TFSF method shown below $$H_x^{n+\frac{1}{2}} = H_x^{n-\frac{1}{2}} - \left(\frac{\Delta t}{\mu_x}\right)\left([\nabla + E]_x^n - \frac{e_y^t \cdot f^n}{\Delta z}\right) \quad \text{Equation (69a)}$$

$$H_y^{n+\frac{1}{2}} = H_y^{n-\frac{1}{2}} - \left(\frac{\Delta t}{\mu_y}\right)\left([\nabla + E]_y^n + \frac{e_x^t \cdot f^n}{\Delta z}\right) \quad \text{Equation (69b)}$$

$$E_x^{n+1} = E_x^n + \left(\frac{\Delta t}{\epsilon_x}\right)\left([\nabla + H]_x^{n+\frac{1}{2}} + \frac{h_y^t \cdot f^{n+\frac{1}{2}}}{\Delta z}\right) \quad \text{Equation (69c)}$$

-continued $$E_y^{n+1} = E_y^n + \left(\frac{\Delta t}{\epsilon_y}\right)\left([\nabla + H]_y^{n+\frac{1}{2}} - \frac{h_x^t \cdot f^{n+\frac{1}{2}}}{\Delta z}\right)$$ Equation (69d)

Note, both E and H source field are excited at the waveport to create the unidirectional propagation of the wave from the waveport. With the TFSF method, it is known explicitly that the incident electric field at the waveport will be exactly e(r)f(t).

In microwave measurement with VNA, the S-parameter between waveport m with the $i^{th}$ mode and waveport n with the $j^{th}$ mode can be defined as $$S_{m,n}^{i,j}(\omega) = \frac{V_m^{i-}(\omega)\sqrt{Z_n^j(\omega)}}{V_n^{j+}(\omega)\sqrt{Z_m^i(\omega)}}$$ Equation (70)

where $V_m^{i-}$ is the received voltage of the $i^{th}$ mode for waveport m, $V_n^{j+}$ is the incident voltage of the $j^{th}$ mode for waveport n. $Z_m^i$ and $Z_n^j$ are the $i^{th}$ and $j^{th}$ mode impedance for waveport m and n. The voltage and current of the $i^{th}$ mode for waveport m can be defined as $$V_m^i(\omega) = \iint_{A_m} E(r,\omega) \times \bar{h}_m^{ti}(r) \cdot dA$$ Equation (71a)

$$I_m^i(\omega) = \iint_{A_m} H(r,\omega) \times \bar{e}_m^{ti}(r) \cdot dA$$ Equation (71b)

where E and H are the electric and magnetic field at waveport m. $A_m$ is the non-PEC surface area for waveport m. $\bar{e}_m^{ti}$ and $\bar{h}_m^{ti}$ are the normalized $i^{th}$ mode template of the electric and magnetic field for waveport m, which shall satisfy $$\iint_{A_m} \bar{e}_m^{ti}(r) \cdot \bar{e}_m^{ti}(r) dA = 1$$ Equation (72a)

$$\iint_{A_m} \bar{h}_m^{ti}(r) \cdot \bar{h}_m^{ti}(r) dA = 1$$ Equation (72b)

The waveport mode voltage and current defined here represent the amplitudes of the electric and the magnetic field, and is only analogous to the traditional voltage and current concept for the transmission line with TEM mode. The impedance of the waveport is also computed numerically with the differential method in Gwarek et al. The impedance of the $i^{th}$ mode for waveport m can be written as $$Z_m(\omega) = \sqrt{\frac{V_m^i(\omega) V_m^{i'}(\omega)}{I_m^i(\omega) I_m^{i'}(\omega)}}$$ Equation (73)

D. Numerical Green's kernel for S-parameter Measurement with Waveport Source

In microwave imaging experiments, the scattered S-parameter is not measured directly. Instead, the S-parameter with and without the presence of the object are measured. The difference between the two is the scattered S-parameter:

$$S_{m,n}^{scat}(\omega) = S_{m,n}^{obj}(\omega) - S_{m,n}^{inc}(\omega)$$ Equation (74)

Using this definition of the scattered S-parameter, we are interested in building a new volume integral equation that directly links unknown object material property to the measurement, which can be written as $$S_{m,n}^{scat}(\omega) = k_b^2 \iiint O(r') G_{m,n}(r',\omega) \cdot E_n(r',\omega) dV'$$ Equation (75)

where $E_n(r', \omega)$ is the total field inside the object region due to the excitation of waveport n, and $G_{m,n}(r', \omega)$ is the new numerical vector Green's function which links the object material property to the scattered S-parameter between waveport m and n.

To derive the new form of the Green's function, start from reciprocity $$\iiint_{V_m} E_{scat}(r,\omega) \cdot J_s(r,\omega) dV = \iiint_{V_{obj}} E_{inc}(r',\omega) \cdot J_{pol}(r',\omega) dV'$$ Equation (76)

where $V_{obj}$ is the volume of the object region, and $V_m$ is the volume of the waveport which equals to $A_m\Delta_z$, the non-PEC surface area of the waveport times the mesh size in the propagation direction. In order to link to the S-parameter, $E_{scat}$ on the LHS of the equation to the scattered voltage is transformed. In FDTD, the current source $J_s$ on the LHS of the Equation (76) is fed into the waveport through $$E_x^{n+1} = E_x^n + \left(\frac{\Delta t}{\epsilon_x}\right)\left([\nabla \times H]_x^{n+\frac{1}{2}} - J_y^{n+\frac{1}{2}}\right)$$ Equation (77a)

$$E_y^{n+1} = E_y^n + \left(\frac{\Delta t}{\epsilon_y}\right)\left([\nabla \times H]_y^{n+\frac{1}{2}} - J_x^{n+\frac{1}{2}}\right)$$ Equation (77b)

If $J_s$ takes the form $$J_s(r,t) = \frac{\hat{n} \times \bar{h}_m^{ti}(r) f(t)}{\Delta z}$$ Equation (78)

take the Fourier transform of $J_s$ and substitute it into the LHS of Equation (76). Then Equation (76) becomes $$\iint_{A_m} E_{scat}(r,\omega) \times \bar{h}_m^{ti}(r) f(\omega) \cdot dA = \iiint_{V_{obj}} E_{inc}(r',\omega) \cdot J_{pol}(r',\omega) dV'$$ Equation (79)

where the LHS of the equation collapses to a surface integral. As shown above, with the proper choice of the current source $J_s$ the LHS of the equation becomes the scattered voltage.

Assume the polarization current is due to the waveport excitation at waveport n. If waveport n is excited with the $i^{th}$ mode field template $e_n^{tj}(r)$ and $h_n^{tj}(r)$ using the TFSF method. The same signal waveform f(t) as Equation (78) is used. Then the incident electric field at waveport n can be written as $$E_n^j(r,t) = e_n^{tj}(r) f(t)$$ Equation (80)

Take the Fourier transform of the incident the electric field and normalize the magnetic field mode template. The incident voltage of the $j^{th}$ mode at waveport n can be written as $$V_n^j(\omega) = \iint_{A_n} e_n^{tj}(r) \times \bar{h}_n^{tj}(r) f(\omega) \cdot dA$$ Equation (81)

Divide both sides of Equation (79) by Equation (81) and the square root of the impedance ratio between waveport m and n, the following results $$\frac{\iint_{A_m} E_{scat}(r,\omega) \times \bar{h}_m^{ti}(r) f(\omega) \cdot dA}{\iint_{A_n} e_n^{tj}(r) \times \bar{h}_n^{tj}(r) f(\omega) \cdot dA} \cdot \frac{\sqrt{Z_n^j(\omega)}}{\sqrt{Z_m^i(\omega)}} =$$

$$\frac{\iiint_{V_{obj}} E_{inc}(r',\omega) \cdot J_{pol}(r',\omega) dV'}{\iint_{A_n} e_n^{tj}(r) \times \bar{h}_n^{tj}(r) f(\omega) \cdot dA} \cdot \frac{\sqrt{Z_n^j(\omega)}}{\sqrt{Z_m^i(\omega)}}$$

Equation (82)

Then the LHS of Equation (82) is the scattered S-parameter between waveport m and n. Substitute Equation (63) the expression of polarization current into the RHS of Equation (82), the result is $$S_{m,n}^{scat}(\omega) = \frac{\iiint_{V_{obj}} j\omega\epsilon_b O(r') E_{inc}(r',\omega) \cdot E_n(r',\omega) dV'}{\iint_{A_n} e_n^{tj}(r) \times \bar{h}_n^{tj}(r) f(\omega) \cdot dA} \cdot \frac{\sqrt{Z_n^j(\omega)}}{\sqrt{Z_m^i(\omega)}}$$

Equation (83)

In order to acquire the form of Equation (75) and extract the numerical vector Green's function, Equation (83) is reorganized and the final form of the numerical vector Green's function for S-parameter measurement with waveport excitation is written as $$G_{m,n}(r',\omega) = \frac{jE_{inc}(r',\omega)\sqrt{Z_n^j(\omega)}}{\omega\mu_0 \iint_{A_n} e_n^{tj}(r) \times \bar{h}_n^{tj}(r) f(\omega) \cdot dA \sqrt{Z_m^i(\omega)}}$$

Equation (84)

The numerical vector Green's function above serves to link the object material contrast function O(r) to the scattered S-parameter between the $i^{th}$ mode of waveport m and $j^{th}$ mode of waveport n. Herein, the quantity $E_{inc}$, $Z_m^i$ and $Z_n^j$ are obtained numerically with the 3D FDTD solver, while the quantity $e_n^{tj}$ and $\bar{h}_n^{tj}(r)$ are calculated with the 2D FDFD solver. The key point of constructing this numerical vector Green's function is the choice of $J_s(r, t)$ in Equation (78). The signal waveform f(t) selected to excite waveport m in Equation (78) should be the same as the one that excites waveport n in Equation (80).

E. Validating the Numerical Vector Green's Function

In this section, the steps to validate this numerical vector Green's function with the scattered S-parameter are outlined. First, the scattered S-parameter $S_{scat}^{m,n}$ with either measurement or simulation is acquired. Then, the predicted scattered S-parameter using numerical vector Green's function with Equation (83) is computed. The two scattered S-parameters to validate the numerical vector Green's function are compared. The detailed steps are listed below.

(1) Obtain the measured scattered S-parameter using Equation (74) with either measurement or simulation.

(2) Use the 2D FDFD solver to calculate the field mode template for waveport m and n of the desired modes. The calculated electric and magnetic field mode template are normalized together with Equation (68) to e'(r) and h'(r), which produce the unit power. Meanwhile, the electric and magnetic field mode template are normalized individually with Equation (72) to $\bar{e}'(r)$ and $\bar{h}'(r)$, which are used to generate the waveport voltage and current. Calculate the waveport impedance with the differential method in Equation (73).

(3) With the presence of the object, we use Equation (69) to excite the $j^{th}$ mode of waveport n with the field mode template $e_n^{tj}(r)$, $h_n^{tj}(r)$ and signal waveform f(t). The total field $E_n(r', t)$ in the object region is computed and recorded with FDTD.

(4) Without the presence of the object, Equation (77) is used to feed a current source $J_s(r, t)$ to waveport m. The current source should take the form of Equation (78) and the signal waveform f(t) used here should be the same as the one in step (3). Then, the incident field $E_{inc}(r', t)$ within the object region is numerically computed and recorded with FDTD.

(5) With the quantities calculated from step (2) to step (4), Equation (84) is used to construct the numerical vector Green's function and plug it into Equation (75) to predict the scattered S-parameter. Then the estimated scattered S-parameter is compared with the measured scattered S-parameter from step (1) to validate the numerical vector Green's function.

EXAMPLES AND RESULTS

In this section, the numerical vector Green's function is validated with three examples. Throughout the examples, the terms measured S-parameter is used to represent the scattered S-parameter acquired with the VNA, simulated S-parameter to mean the scattered S-parameter calculated by the FDTD simulation, and predicted S-parameter to mean the scattered S-parameter calculated by the numerical Green's function. The validation steps were described in detail above.

A. Example 1

Figure 41:
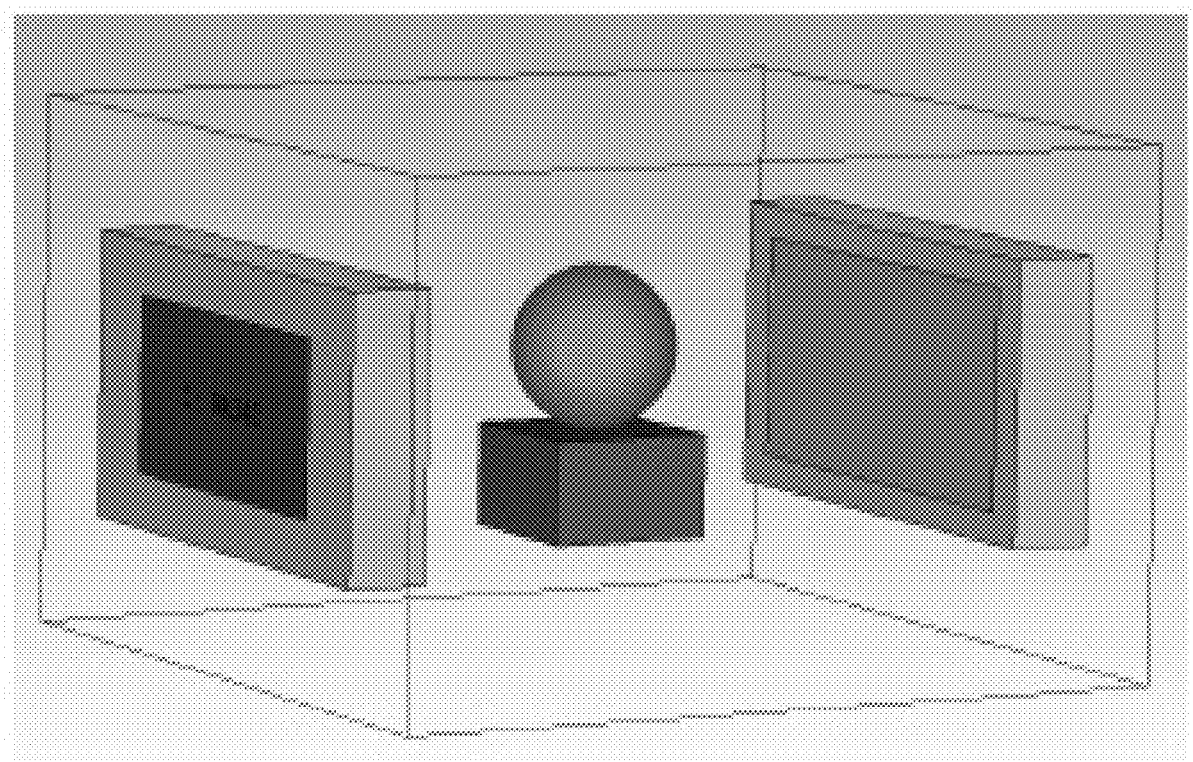
FIG. 41 illustrates a CAD model for simulation region of Example 1 where the two rectangular air-filled aperture of the size of WR-340 (left) and WR-430 (right) are embedded into the PEC wall.

First, the numerical vector Green's function is validated in simulation by comparing the simulated S-parameter and the predicted S-parameter from two dielectric objects under waveport source excitation. The simulation domain is shown in FIG. 41. In the simulation region, there are two PEC walls of size 130×70×20 mm³ facing each other 160 mm apart. Within the PEC walls, there are two rectangular apertures. One aperture on the left of FIG. 41 is waveport 1, which has the size of WR-340 waveguide and serves as the transmitter. Another aperture on the right of FIG. 41 is waveport 2, which has the size of WR-430 waveguide and serves as the receiver. Two dielectric objects, which are used to generate the scattered S-parameter, are placed in the middle of the two waveports. One is a rectangular box with dimension 40×40 mm² and a dielectric constant of 2. On top of the rectangular box, there is a dielectric ball with radius of 20 mm and dielectric constant of 4. The remaining region in the simulation domain is filled with air. The whole simulation domain is discretized with the hexahedral mesh.

Waveport 1 is excited with its TE10 mode and the TE10 mode scattered field in waveport 2 is calculated from 2 GHz to 3 GHz with a frequency step of 20 MHz. The field mode template for waveport 1 (WR-340) and waveport 2 (WR-430) are calculated by the 2D FDFD solver at 2.5 GHz. The simulated scattered S-parameter is calculated with FDTD using Equation (74) and the S-parameter extraction method described in Navarro et al. The predicted scattered S-parameter is computed with the numerical vector Green's function described herein. First, without the presence of the two dielectric objects, the waveport 2 is excited using the TE10 mode normalized magnetic field template with the signal waveform, and the incident field within the object region is computed with FDTD. Then, with the presence of the two dielectric objects, waveport 1 is excited using the TE10 mode template of both electric field and magnetic field with the signal waveform, and the total field within the object region is computed with FDTD. With Equation (83), the predicted scattered S21 is obtained.

Figure 42A:
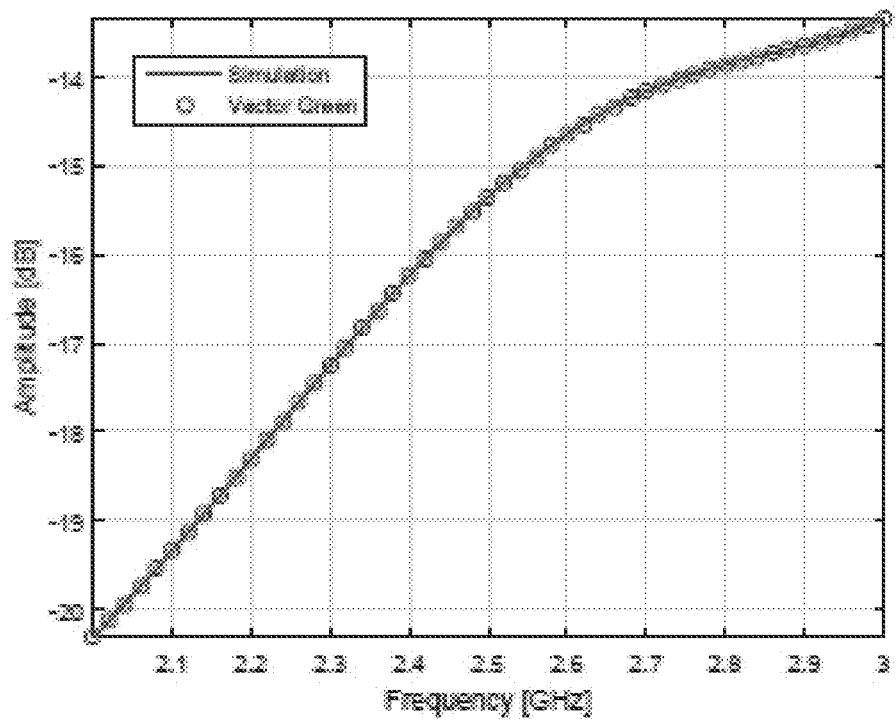
FIGS. 42A and 42B illustrate a comparison of scattered S21 simulated by FDTD and predicted by numerical vector Green's function; the amplitude agrees within 0.5 dB and phase agrees within 3 degrees.
Figure 42B:
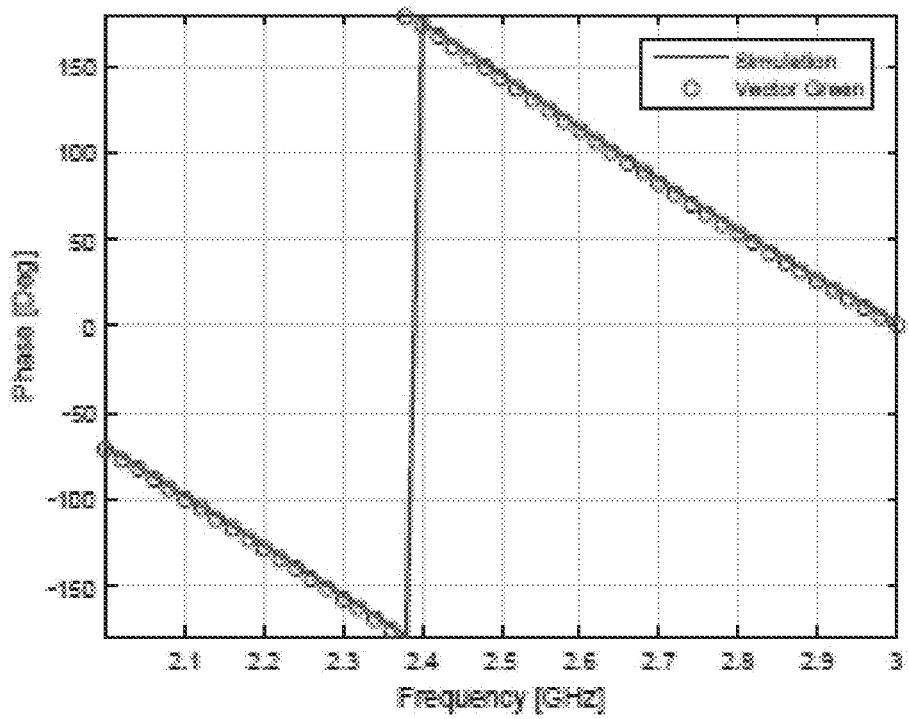

As can be seen from FIGS. 42A-42B, the predicted scattered S21 matches very well with the simulated scattered S21. The amplitude agrees within 0.5 dB and the phase agrees within 3 degrees.

B. Example 2

Figure 43A:
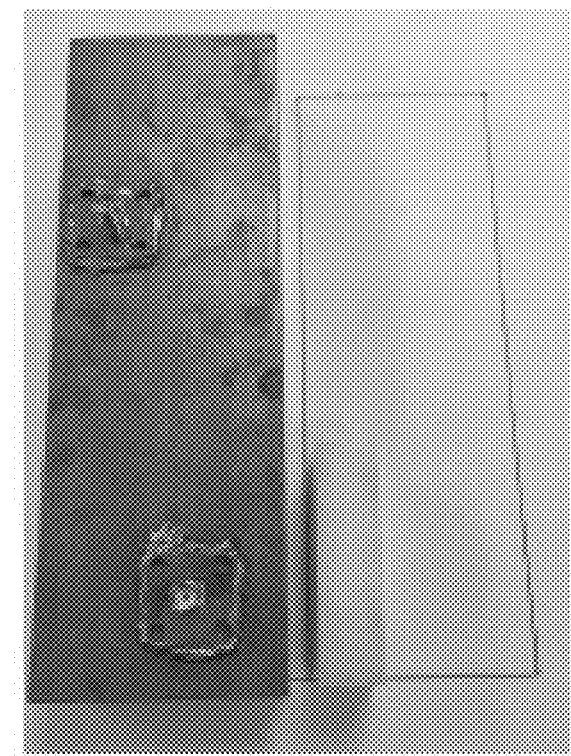
FIG. 43A illustrates a dielectric loaded two-probe fed waveguide at a top view of the waveguide and the relative location of the nylon block within the waveguide.
Figure 43B:
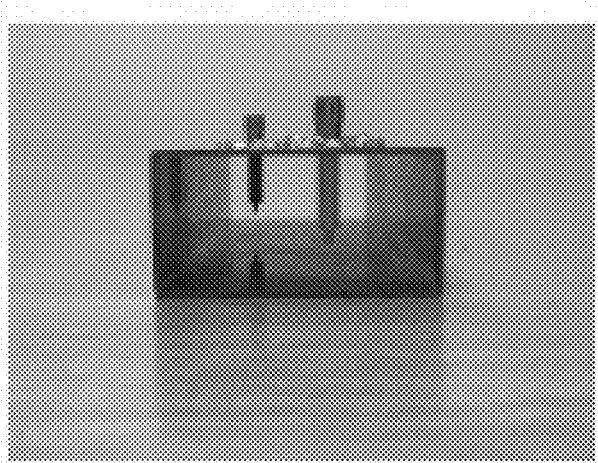
FIG. 43B illustrates a dielectric loaded two-probe fed waveguide at a side view of the waveguide.
Figure 44:
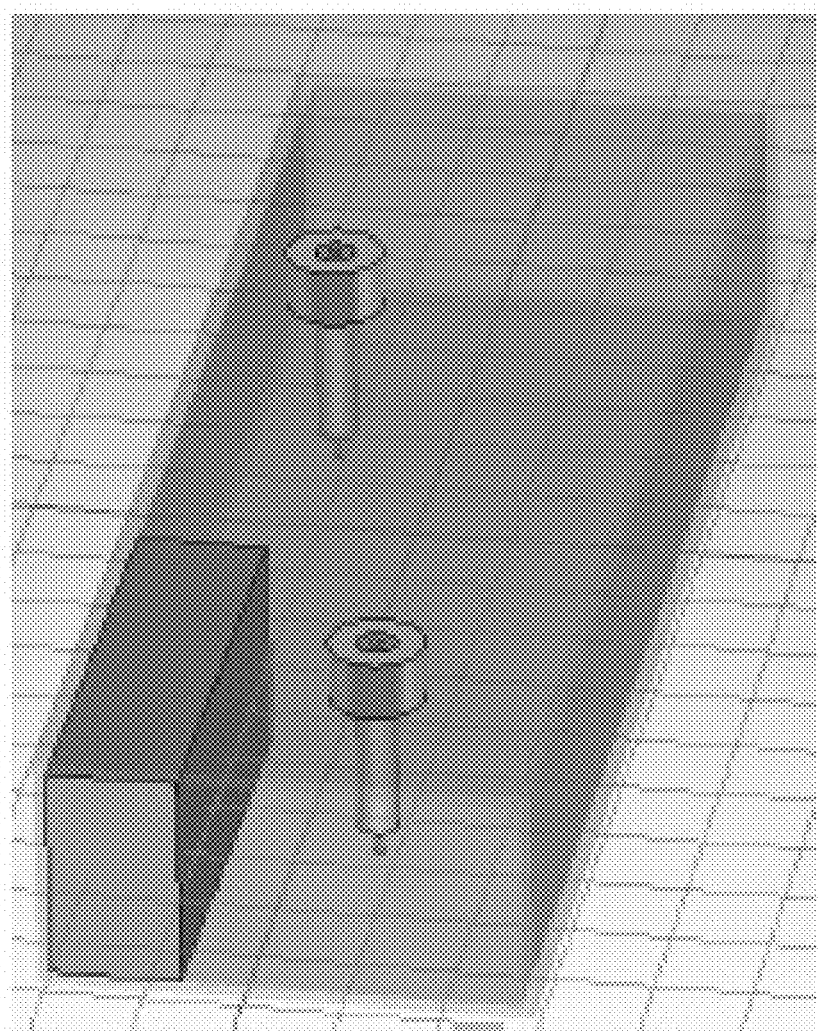
FIG. 44 illustrates a CAD model of the dielectric loaded waveguide where a waveport source is used to excite the coaxial feed.

In this example, the numerical vector Green's function in measurement with a dielectrically loaded two-probe fed rectangular waveguide is validated. The waveguide is hollow brass with WR-187 specifications and an outer dimension of 2.54×5.08×15.2 cm³. The two probes are coaxial SMA extended Teflon flange mount connectors. As shown in FIGS. 43A-43B, probe 1 is located 1.91 cm inward from one corner along both axes and probe 2 is located 2.54 cm and 1.27 cm from the other corner. Here the coaxial feed of probe 1 is waveport 1, and the coaxial feed of probe 2 is waveport 2. Both the excited source at waveport 1 and the received field in waveport 2 are in the TEM mode. The nylon block, which produces the scattered S-parameter has a dimension of 2.40×1.45×5.05 cm³ and a dielectric constant of 3.1.

The measurement is performed with the vector network analyzer from 3 to 6 GHz with a frequency step of 50 MHz. The whole waveguide is surrounded by microwave absorber. To measure the scattered S-parameter, the nylon block is inserted into the bottom left corner of the waveguide as indicated in FIGS. 43A-43B and the S21 is measured with the presence of the object. Then, the nylon block is removed and the incident S21 is measured. The difference between the two is the scattered S21. The simulated scattered S21 is obtained as before with FDTD simulation.

Figure 45A:
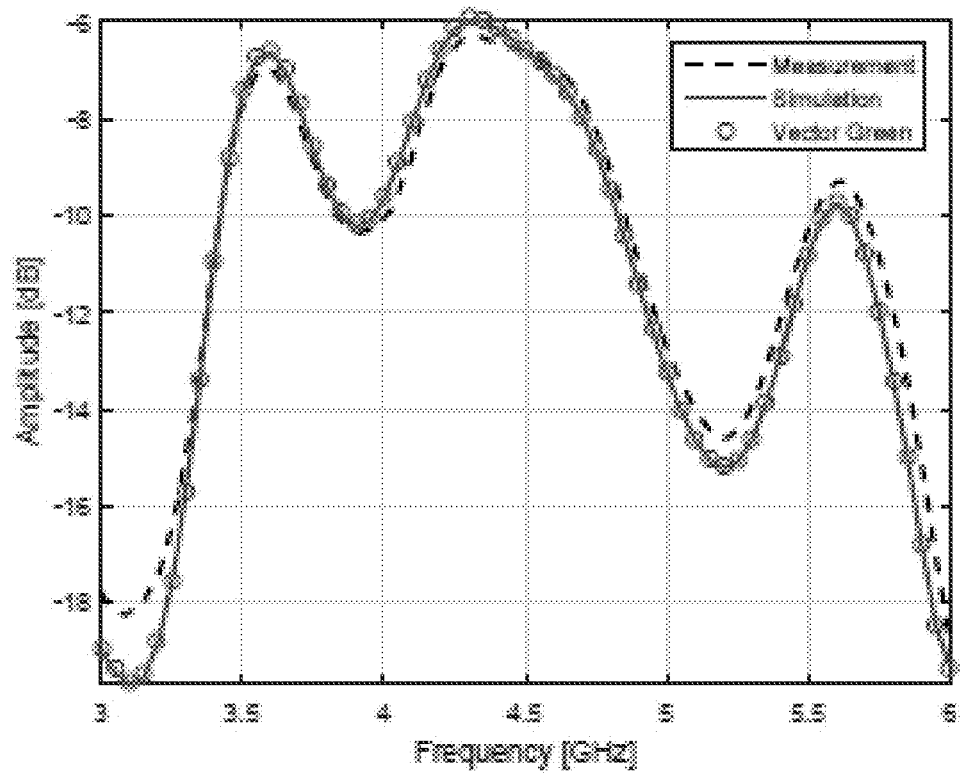
FIGS. 45A and 45B illustrate a comparison of scattered S21 measured with VNA, simulated by FDTD and predicted by numerical vector Green's function. Compare the simulated and predicted S21, the amplitude agrees within 0.5 dB and the phase agrees within 2 degrees. Compare the measured and predicted S21, the amplitude agrees within 2 dB and the phase agrees within 10 degrees.
Figure 45B:
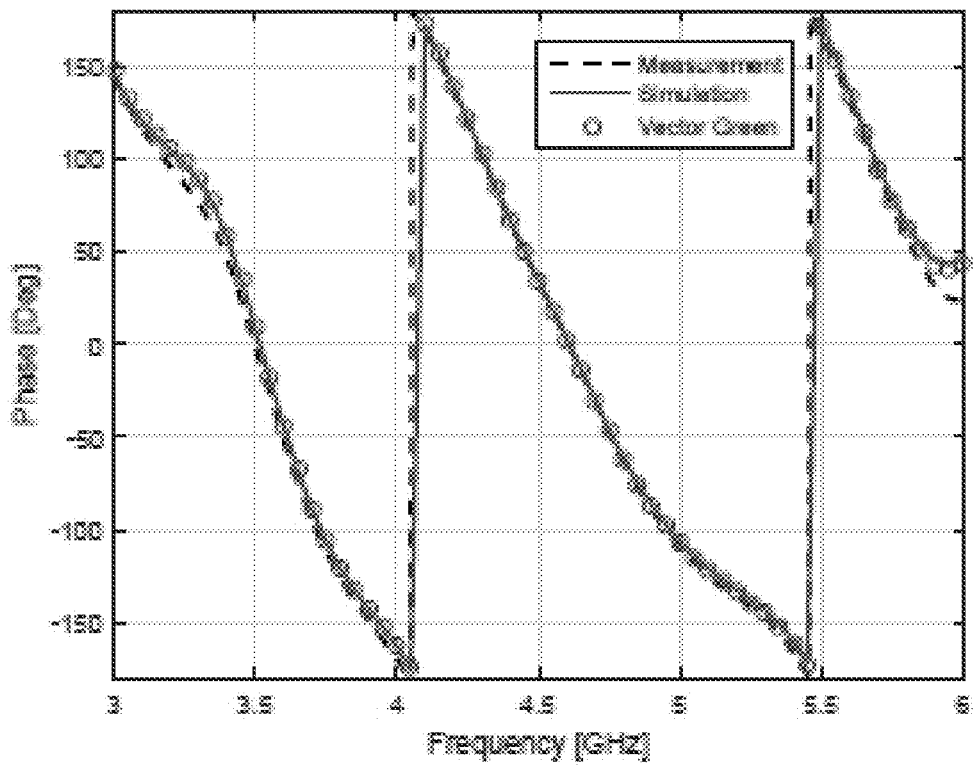

To compute the numerical vector Green's function, the incident and total electric field within the object region are computed with the FDTD method. The predicted scattered S21 is obtained with the same steps described above. Note that TEM mode template for both coaxial feed is used, that is the only mode that exists in the measurement frequency range. As can be seen in FIGS. 45A-45B, the amplitude of simulated and predicted scattered S21 agrees within 0.5 dB, and the phase agrees within 2 degrees. The amplitude of the measured and predicted S21 agrees within 2 dB, and the phase agrees within 10 degrees.

C. Example 3

Figure 46A:
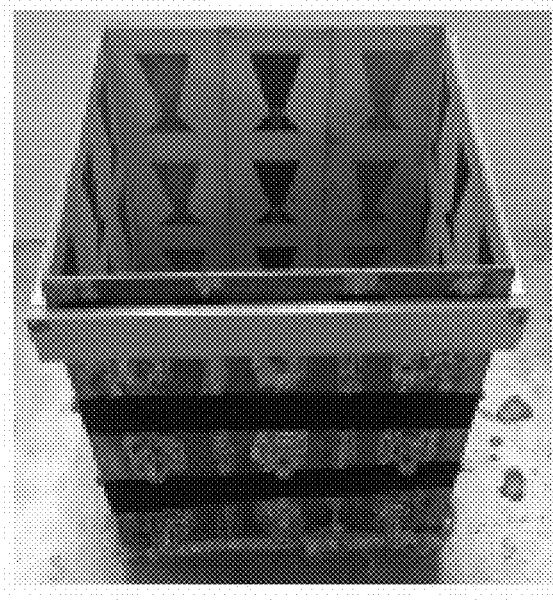
FIGS. 46A and 46B illustrate an imaging cavity and dimensions of a tapered patch antenna.
Figure 46B:
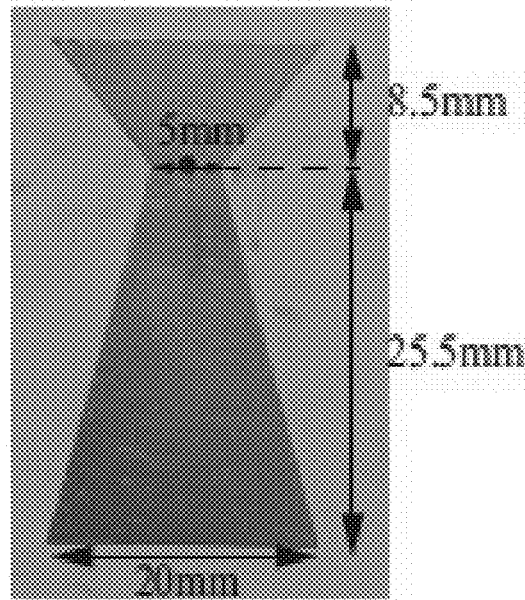
Figure 47A:
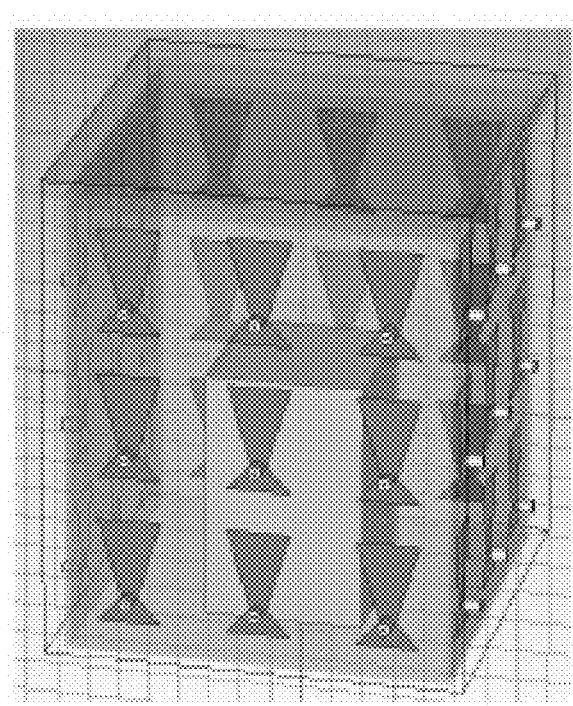
FIG. 47A illustrates a CAD of the imaging cavity with the nylon block, where waveport 1, 2 and 3 are located in the middle ring of antenna feed and waveport 4 is located in the bottom ring of antenna feed.
Figure 47B:
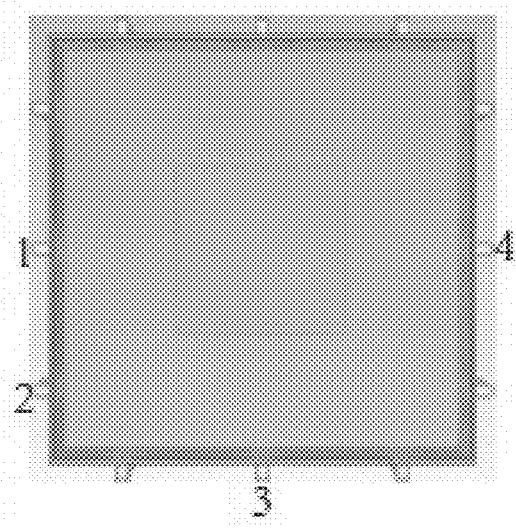
FIG. 47B illustrates a CAD of the imaging cavity with the nylon block at a top view of the cavity with the location of the 4 coaxial feed waveports, where waveport 1, 2, and 3 are located in the middle ring of antenna feed and waveport 4 is located in the bottom ring of antenna feed.
Figure 48A:
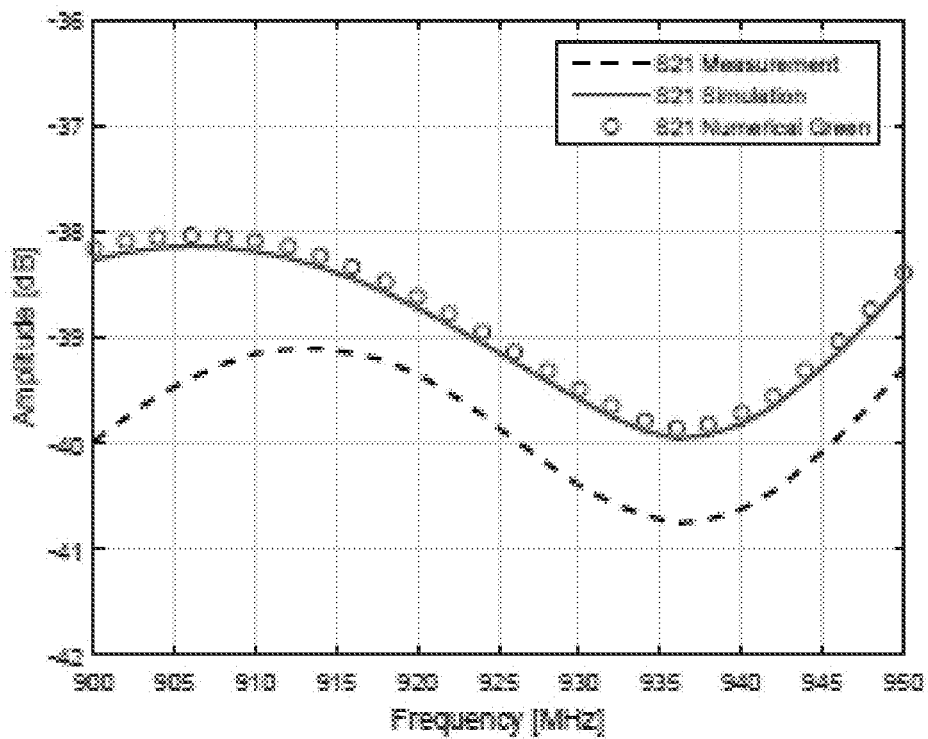
FIGS. 48A and 48B illustrate a comparison of scattered S21; the amplitude and phase of the simulated and predicted S21 agrees within 0.2 dB and 2 degrees and the amplitude and phase of the measured and predicted S21 agrees within 2 dB and 8 degrees.
Figure 48B:
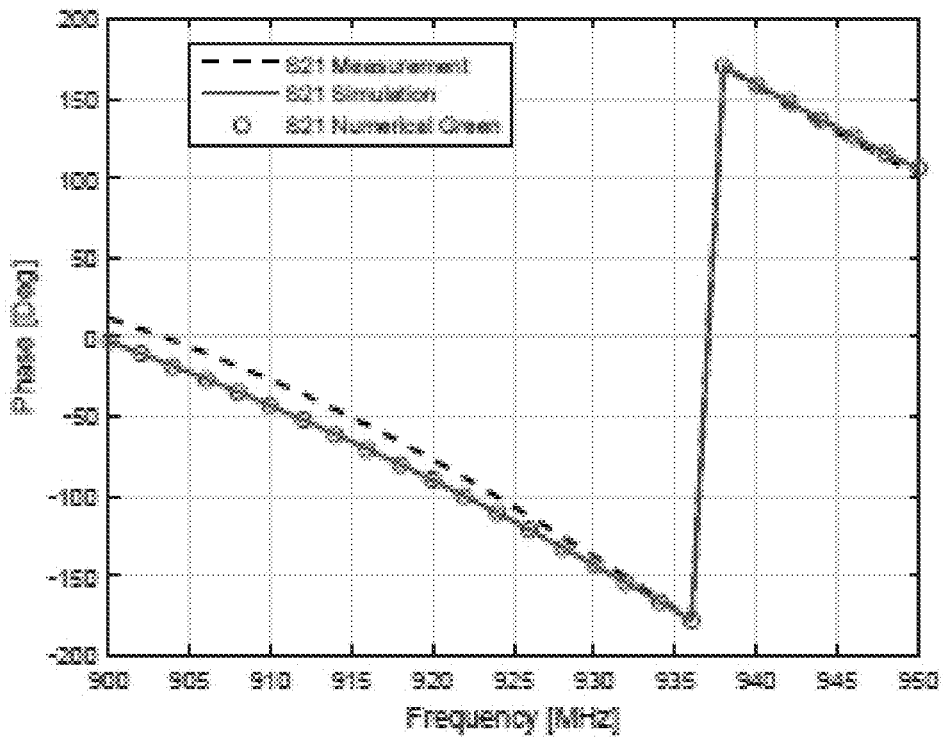
Figure 49A:
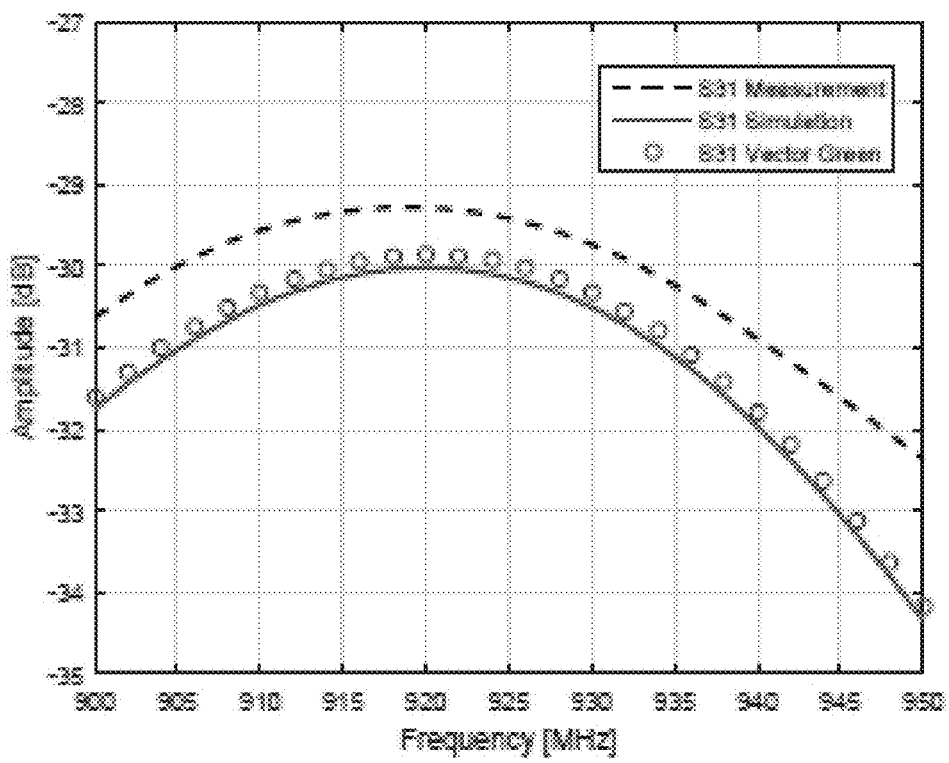
FIGS. 49A and 49B illustrate a comparison of scattered S31; the amplitude and phase of the simulated and predicted S31 agrees within 0.2 dB and 2 degrees and the amplitude and phase of the measured and predicted S31 agrees within 2 dB and 10 degrees.
Figure 49B:
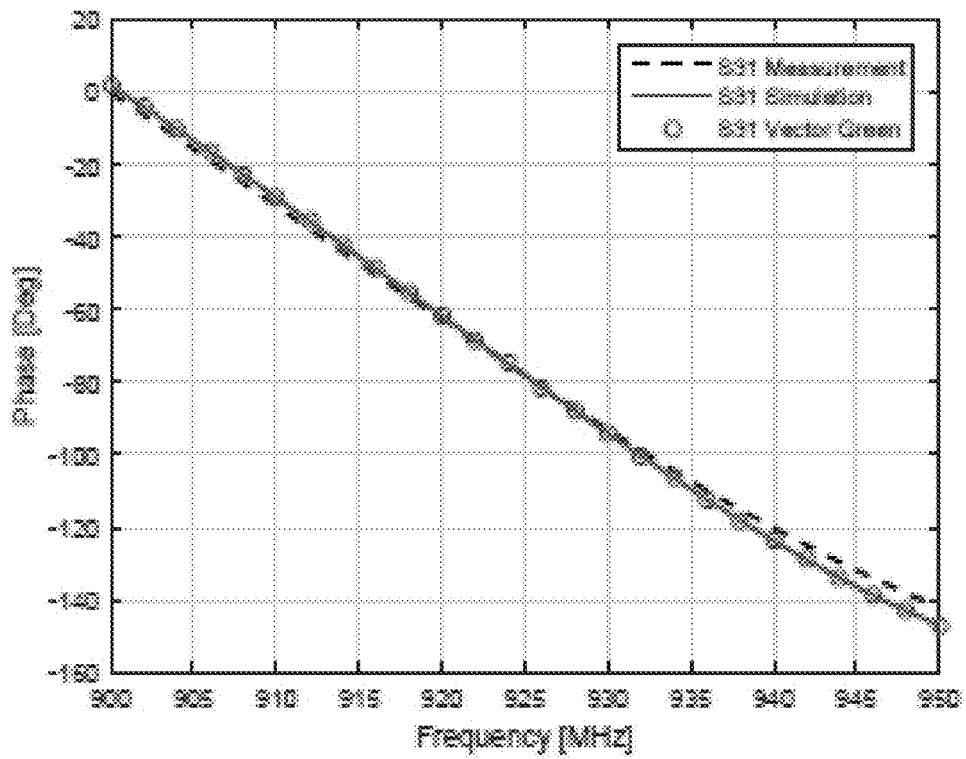
Figure 50A:
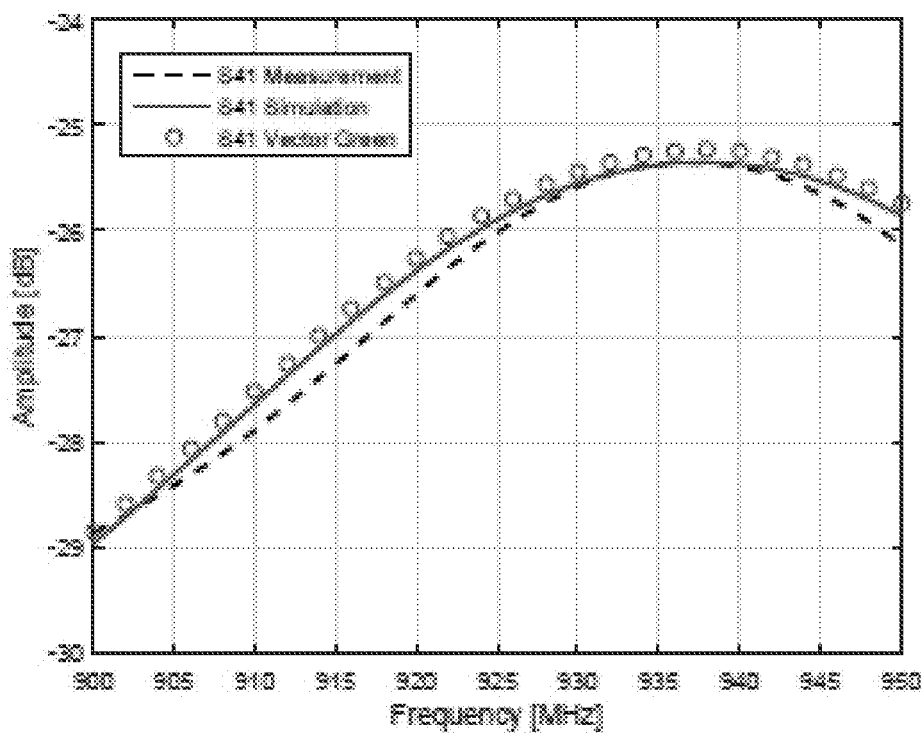
FIGS. 50A and 50B illustrate a comparison of scattered S41; the amplitude and phase of the simulated and predicted S41 agrees within 0.2 dB and 2 degrees and the amplitude and phase of the measured and predicted S41 agrees within 0.5 dB and 10 degrees.
Figure 50B:
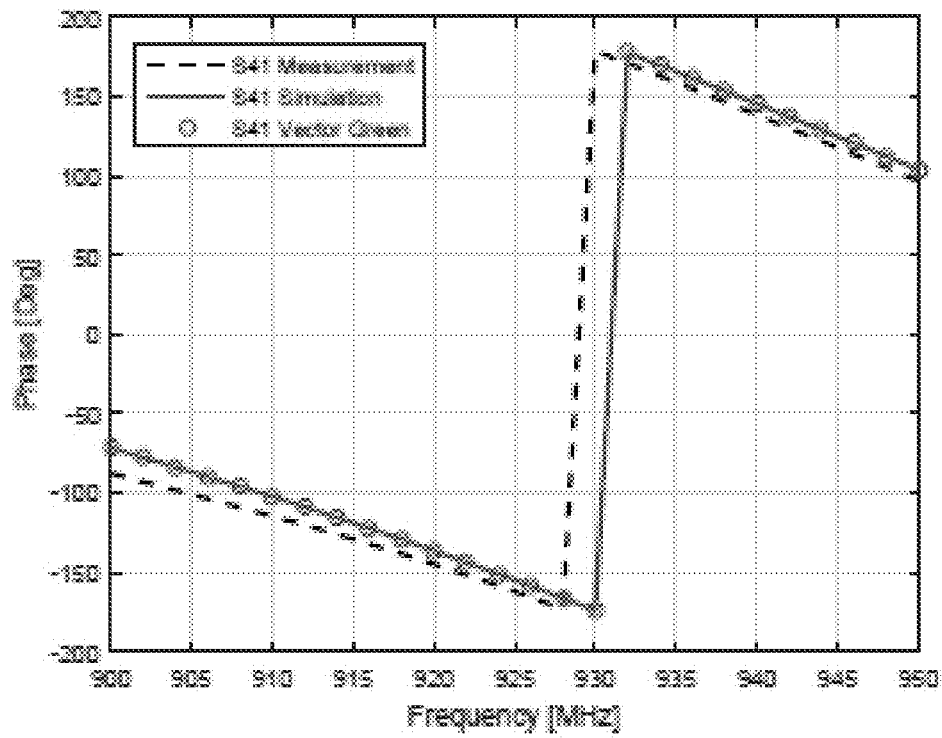

In this example, the numerical vector Green's function in measurement with a square imaging cavity is validated. The imaging cavity is built for inverse scattering experiments and has an outer dimension of 12.2×12.2×15.2 cm³. The four panels of the square cavity are made of Roger 3010 substrate with a thickness of 50 mil and dielectric constant of 10.2. There are 36 tapered patch antennas printed on the inside of the 4 panels, and their dimensions are shown in FIGS. 46A-46B. The antennas are designed to radiate into an emulsion fluid coupling material and their resonance frequency is 920 MHz. The measurement is performed near the resonance frequency of the antenna from 900 to 950 MHz with a 2 MHz frequency step. Within this frequency range, the emulsion fluid is measured to have a dielectric constant $\epsilon_r$ of 19.5 and a conductivity $\sigma$ of 0.075 s/m. A Nylon block with a dimension of 5.1×5.1×7.9 cm³ and a dielectric constant of 3.1 is placed in the center of the imaging cavity as shown in FIGS. 47A-47B. Thus in this experiment, the scattered S-parameter is produced by both the permittivity and conductivity contrast.

In the measurement, the scattered S-parameter was sampled from 3 pairs of antennas, where antenna 1 is used as the transmitter and antennas 2, 3, 4 are used as the receivers as shown in FIGS. 47A-47B. Antennas 1, 2, 3 are located in the middle ring, while antenna 4 is located in the bottom ring. Four waveports are assigned to the four SMA feeds in simulation. Within the measurement frequency, only TEM mode exists in the coaxial feed, and thus TEM mode template is used for the waveports. The measured and simulated scattered S-parameters are obtained with Equation (74) and the predicted scattered S-parameter is obtained as discussed above.

As can be seen from FIGS. 48A-48B, 49A-49B, and 50A-50B, the amplitude and phase of the simulated and predicted scattered S-parameter agrees within 0.2 dB and 2 degrees. Meanwhile, the amplitude and phase of the measured and predicted scattered S-parameter agrees within 2 dB and 10 degrees.

Various features and advantages of the invention are set forth in the following claims.

What is claimed is:

1. A system of monitoring in real-time a thermal therapy, the system comprising:
    an imaging cavity including a plurality of antennas arranged in a three-dimensional array around the imaging cavity; and
    a controller operatively connected to the imaging cavity, the controller configured to:
        determine an incident electric field inside the imaging cavity for each of the plurality of antennas without an object of interest positioned inside the imaging cavity, wherein determining the incident electric field includes collecting a first plurality of pairwise measurements from the plurality of antennas to determine a plurality of incident S-parameters when the object of interest is not positioned inside the imaging cavity
        collect, with an electronic processor, a second plurality of pairwise measurements from the plurality of antennas when the object of interest is positioned inside the imaging cavity to determine a plurality of total S-parameters,
        calculate a plurality of measured differential S-parameters by subtracting the incident S-parameters from the total S-parameters
        generate a numerical function directly linking a material property of the object of interest to the plurality of measured differential S-parameters, wherein the material property is indicative of a permittivity of the object of interest,
        determine a solution of the numerical function for the material property of the object of interest using local optimization,
        generate an estimated map of complex permittivity of the object of interest in the imaging cavity using the solution of the numerical function for the material property,
        calculate a total electric field inside the imaging cavity and a plurality of calculated differential S-parameters based on the estimated map of the complex permittivity using a conformal finite-difference time domain (CFDTD) forward solver,
        compare the calculated differential S-parameters and a measured differential S-parameter,
        generate an updated numerical function based at least in part on the measured total electric field in response to determining that a difference between the calculated differential S-parameter and the measured differential S-parameter is greater than a threshold difference, and
        output the estimated map of complex permittivity for the object of interest in response to determining that a difference between the calculated differential S-parameter and the measured differential S-parameter is less than a threshold difference.

2. The system of claim 1, wherein the controller is configured to generate the numerical function based on the determined incident electric field inside the imaging cavity.

3. The system of claim 1, wherein the controller is further configured to
determine a linear inverse scattering solution, and
apply the linear inverse scattering solution in real-time to real-time measurement values, the real-time measurement values being continuously received by imaging hardware.

4. The system of claim 3, wherein the controller is configured to determine the linear inverse scattering solution using a distorted born approximation.

5. The system of claim 1, wherein the numerical function is a numerical vector Green's function.

6. The system of claim 1, wherein the controller is configured to determine the incident electric field inside the imaging cavity for each of the plurality of antennas without the object of interest positioned inside the imaging cavity by using the conformal finite-difference time domain (CFDTD) forward solver to determine the incident electric field.

7. The system of claim 1, wherein the controller is further configured to:
collect subsequent pairwise measurements from the plurality of antennas;
determine a plurality of subsequent S-parameter measurements based on the collected subsequent pairwise measurements; and
update the estimated map of complex permittivity for the object of interest based on the plurality of subsequent S-parameter measurements in real time.

8. The system of claim 7, wherein the controller is further configured to quantify thermal changes of the object of interest based at least in part on the updated estimated map of complex permittivity.

9. The system of claim 1, wherein the controller is further configured to quantify thermal changes of the object of interest based at least in part on the estimated map of complex permittivity.

10. The system of claim 1, further comprising a switching system configured to selectively electrically couple a transmitting antenna of the plurality of antennas directly to a receiving antenna of the plurality of antennas between each successive antenna pair measurement in a continuous data stream of antenna pair measurements,
wherein the controller is configured to collect the plurality of pairwise measurements from the antennas by
receiving the continuous data stream of antenna pair measurements, and
segmenting the continuous data stream of antenna pair measurements into a plurality of individual antenna pair measurements by using magnitude thresholding to detect a signal magnitude in the continuous data stream indicative of the direct electrical coupling between the transmitting antenna and the receiving antenna.

* * * * *

UNITED STATES PATENT AND TRADEMARK OFFICE
CERTIFICATE OF CORRECTION

| | |
|---|---|
| PATENT NO. | : 11,426,080 B2 |
| APPLICATION NO. | : 15/658305 |
| DATED | : August 30, 2022 |
| INVENTOR(S) | : John P. Stang et al. |

It is certified that error appears in the above-identified patent and that said Letters Patent is hereby corrected as shown below:

In the Specification

Column 1, Line 13, please delete the following:
"STATEMENT REGARDING FEDERALLY SPONSORED RESEARCH OR DEVELOPMENT
This invention was made with government support under No. 53-4502-6382 awarded by the U.S. Department of Defense and under No. W81XWH-10-1-0514 awarded by the Army Medical Research and Materiel Command. The government has certain rights in the invention."

Please insert the following:
--STATEMENT REGARDING FEDERALLY SPONSORED RESEARCH OR DEVELOPMENT
This invention was made with government support under W81XWH-10-1-0514 awarded by the Medical Research and Development Command. The government has certain rights in the invention.--

Signed and Sealed this
Nineteenth Day of March, 2024

Katherine Kelly Vidal
*Director of the United States Patent and Trademark Office*